(12) United States Patent
Wang et al.

(10) Patent No.: US 9,371,322 B2
(45) Date of Patent: Jun. 21, 2016

(54) BICYCLIC AZA-AMIDES FOR TREATMENT OF PSYCHIATRIC DISORDERS

(71) Applicant: MAX-PLANCK-GESELLSCHAFT ZUR FÖRDERUNG DER WISSENSCHAFTEN E.V., München (DE)

(72) Inventors: Yansong Wang, Sichuan (CN); Felix Hausch, Munich (DE)

(73) Assignee: Max-Planck-Gesellschaft zur Förderung der Wissenschaften e.V., München (DE)

(*) Notice: Subject to any disclaimer, the term of this patent is extended or adjusted under 35 U.S.C. 154(b) by 0 days.

(21) Appl. No.: 14/416,604

(22) PCT Filed: Jul. 24, 2013

(86) PCT No.: PCT/EP2013/002247
§ 371 (c)(1),
(2) Date: Jan. 22, 2015

(87) PCT Pub. No.: WO2014/015993
PCT Pub. Date: Jan. 30, 2014

(65) Prior Publication Data
US 2015/0183786 A1 Jul. 2, 2015

(30) Foreign Application Priority Data

Jul. 24, 2012 (EP) .................................... 12177733

(51) Int. Cl.
C07D 471/08 (2006.01)
A61K 31/4995 (2006.01)
A61K 8/49 (2006.01)
A61K 45/06 (2006.01)
A61Q 7/00 (2006.01)

(52) U.S. Cl.
CPC .............. *C07D 471/08* (2013.01); *A61K 8/494* (2013.01); *A61K 31/4995* (2013.01); *A61K 45/06* (2013.01); *A61Q 7/00* (2013.01); *A61K 2800/10* (2013.01)

(58) Field of Classification Search
CPC .......................... C07D 471/08; A61K 31/4995
USPC .......................................... 540/500; 514/221
See application file for complete search history.

(56) References Cited

FOREIGN PATENT DOCUMENTS

| WO | WO 01/42245 | 6/2001 |
| WO | WO 02/089806 | 11/2002 |
| WO | WO 2007/024651 | 3/2007 |

OTHER PUBLICATIONS

Bundgaard, Design of Prodrugs, p. 1, 1985.*
Silverman, Chapter 8: Prodrugs and Drug Delivery Systems, The Organic Chemistry of Drug Design and Drug Action, pp. 352-400 (1992).*
Banker et al., Prodrugs, Modern Pharmaceutics, Third Edition, Revised and Expanded, pp. 451 and 596 (1996).*
Wolff, Some consideration for prodrug design, Burgers Medicinal Chemistry and Drug Discovery, 5th Edition, vol. I: Principles and Practice, pp. 975-977, 1995.*
Gura et al., Systems for identifying new drugs are often faulty, Science, 278:1041-1042, 1997.*
Johnson et al., Relationships between drug activity in NCI preclinical in vitro and in vivo models and early clinical trials, British Journal of Cancer, 84(10):1424-1431,2001.*
Pearce et al., Failure modes in anticancer drug discovery and development, Cancer Drug Design and Discovery Edited by Stephen Neidle, Chapter 18, pp. 424-435 (2008).*
Simone, Oncology: Introduction, 20th Edition, vol. 1, pp. 1004-1101 O, 1996.*
Layzer, Degenerative Diseases of the Nervous System, Cecil Textbook of Medicine, 20th Edition, vol. 2, pp. 2050-2057 (1996).*
Damasio, Alzheimer's Disease and Related Dementias, Cecil Textbook of Medicine, 20th Edition, vol. 2, pp. 1992-1996 (1996).*
Blackburn et al., Targeting FKBP isoforms with small-molecule ligands, Current Opinion in Pharmacology, 11, pp. 365-371 (2011).*
Sun et al., Design and Structure-Based Study of New Potential FKBP12 Inhibitors, Biophysical Journal, vol. 85, pp. 3194-3201, Nov. 2003.*
Hudack, R. A., et al., "Design, Synthesis, and Biological Activity of Novel Polycyclic Aza-Amides FKBP12 Ligands" J. Med. Chem. (2006) 49(3):1201-1206.
International Search Report and Written Opinion dated Aug. 26, 2013 for PCT Application No. PCT/EP2013/002247 filed Jul. 24, 2013.
Ni et al., "FKBP51 Promotes Assembly of the Hsp90 Chaperone Complex and Regulates Androgen Receptor Signaling in the Prostate Cancer Cells" *Molecular and Cellular Biology* (2010) 30(5):1243-1253.
Binder, E.B., "The role of FKBP5, a co-chaperone of the glucocorticoid receptor in the pathogenesis and therapy of affective and anxiety disorders" *Psychoneuroendocrinology* (2009) 34:186-195.

(Continued)

*Primary Examiner* — Deepak Rao
(74) *Attorney, Agent, or Firm* — Knobbe, Martens, Olson & Bear, LLP

(57) ABSTRACT

The present invention relates to compounds of formula (I) having a bicyclic aza-amides scaffold, pharmaceutically acceptable salts of these compounds and pharmaceutical compositions containing at least one of these compounds together with pharmaceutically acceptable carrier, excipient and/or diluents. Said bicyclic aza-amides compounds can be used for prophylaxis and/or treatment of psychiatric disorders and neurodegenerative diseases, disorders and conditions.

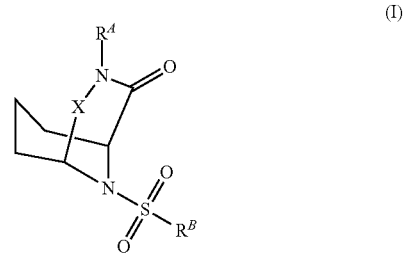

15 Claims, No Drawings

(56) References Cited

OTHER PUBLICATIONS

Galigniana et al., "Regulation of the glucocorticoid response to stress-related disorders by the HSP90-binding immunophilin FKBP51" *Journal of Neurochemistry* (2010) 122:4-18.

Romano et al., "Role of FK506-binding protein in 51 in the control of apoptosis of irradiated melanoma cells" *Cell Death Differentiation* (2010) 17:145-157.

Sanchez, E.R., et al., "Chaperoning steroidal physiology: Lessons from mouse genetic models of Hsp90 and its cochaperones" *Biochimica Biophysica Acta* (2012) 1823:722-729.

Warrier, Manya, Role of FKBP51 and FKBP52 in Glucocorticoid Receptor Regulated Metabolism (Jul. 23, 2008) (Ph.D. Dissertation, The University of Toledo).

* cited by examiner

BICYCLIC AZA-AMIDES FOR TREATMENT OF PSYCHIATRIC DISORDERS

The present invention relates to bicyclic aza-amides derivatives and stereoisomeric forms, solvates, hydrates and/or pharmaceutically acceptable salts of these compounds as well as pharmaceutical compositions containing at least one of these bicyclic aza-amides derivatives together with pharmaceutically acceptable carrier, excipient and/or diluents. Said bicyclic aza-amides derivatives have been identified as specific inhibitors of the FK506 binding proteins (FKBP's), especially FKBP-51 and FKBP-52, and are useful for the treatment of psychiatric disorders and neurodegenerative diseases, disorders and conditions, for treating vision disorders and/or improving vision; for treating memory impairment and/or enhancing memory performance and for treating alopecia and promoting hair growth.

BACKGROUND OF THE INVENTION

The FK506-binding protein (FKBP) family of immunophilins consists of proteins with a variety of protein-protein interaction domains and versatile cellular functions. This highly conserved protein family binds with immunosuppressive drugs, such as FK506 and rapamycin. This protein family displays peptidyl propyl isomerase (PPIase) activity as seen with cyclophilins and parvulins. FKBP12, a 12 kD protein is the most widely studied member of this family.

The immunosuppressant drugs FK506, rapamycin, and cyclosporin are well known as potent T-cell specific immunosuppressants, and are effective against autoimmunity, transplant or graft rejection, inflammation, allergic responses, other autoimmune or immune-mediated diseases, and infectious diseases. FK506 and rapamycin apart from binding to FKBP12 also interact and inhibit calcineurin (CaN) and mTOR respectively thereby mediating their immunosuppressive action.

The high molecular weight multidomain homologs of FKBP12 (FKBP51/52) act as co chaperons for the heat shock protein (Hsp90) and modulate the signal transduction of the glucocorticoid receptor by participating in the Heat shock protein 90 (Hsp90) steroid receptor complex.

In this complex, FKBP 51 and 52 modulate the binding competence and signalling of steroid hormone receptors and thereby regulate the cellular responsiveness to circulating hormone levels. This is supported by a natural animal model (squirrel monkey) and by knockout mice, where the essential role of FKPB 51 and 52 on the Glucocorticoid Receptor (GR) activity have been clearly demonstrated. Moreover, polymorphisms in the FKBP51-encoding gene of psychiatric patients have been associated with a faster response to antidepressants, with a higher incidence in depressive episodes and with a higher susceptibility for peritraumatic dissociation.

The immunosuppressive compounds, like FK506, disclosed in the prior art suppress the immune system, by definition, and also exhibit other toxic side effects. Accordingly, there is a need for non-immunosuppressant, small molecule compounds, and compositions and methods for use of such compounds, that are useful in treating psychiatric disorders and neurodegenerative diseases, disorders and conditions.

Further studies led to α-ketoamide analogs of FK506 devoid of immunosuppressive activity. So far there has been only few investigations on the activity of monocyclic, pipecolate or proline-based compounds concerning the larger FKBP's (FKBP51 and 52).

Also, the main physiological role of FKBP51 is believed to be the inhibition of glucocorticoid receptor signaling, especially in stressful situations. However, the FKBP51-GR interplay (glucocorticoid receptor interplay) has been difficult to assess pharmacologically, largely due to lack of appropriate chemical probes. The best synthetic FKBP51 inhibitors so far were highly hydrophobic and suffered form a limiting aqueous solubility.

It is the object of the present invention to provide compounds and/or pharmaceutically acceptable salts thereof which inhibit FKBP 51 and FKBP 52 but which show no immunosuppressive activity and are non toxic.

A further aspect of the invention is to provide compounds and/or pharmaceutically acceptable salts thereof which can be used as pharmaceutically active agents, especially for the treatment of psychiatric disorders and neurodegenerative diseases, disorders and conditions, for treating vision disorders and/or improving vision; for treating memory impairment and/or enhancing memory performance and for treating alopecia, as well as compositions comprising at least one of those compounds and/or pharmaceutically acceptable salts thereof as pharmaceutically active ingredients.

The objective of the present invention is solved by the teaching of the independent claims. Further advantageous features, aspects and details of the invention are evident from the dependent claims, the description, and the examples of the present application.

DESCRIPTION OF THE INVENTION

Thus the present invention relates to the compounds of general formula (I):

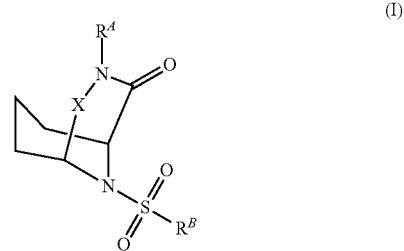

wherein
X represents —$CH_2$—, —$CH_2$—$CH_2$—, —CH(CH=$CH_2$)— or —CH(CH=$CH_2$)—$CH_2$—;
$R^A$ represents —H, —$CH_3$, —$C_2H_5$, —$C_3H_7$, —CH($CH_3$)$_2$, —$CH_2$—CH($CH_3$)$_2$, —CH($CH_3$)—$C_2H_5$, —C($CH_3$)$_3$, —$C_6H_{11}$, —CH($CH_3$)—$C_3H_7$, —$CH_2$—CH($CH_3$)—$C_2H_5$, —CH($CH_3$)—CH($CH_3$)$_2$, —C($CH_3$)$_2$—$C_2H_5$, —$CH_2$—C($CH_3$)$_3$, —CH($C_2H_5$)$_2$, —$C_2H_4$—CH($CH_3$)$_2$, —$C_6H_{13}$, —$C_7H_5$, —$C_8H_{17}$, —$C_3H_6$—CH($CH_3$)$_2$, —$C_2H_4$—CH($CH_3$)—$C_2H_5$, —CH($CH_3$)—$C_4H_9$, —$CH_2$—CH($CH_3$)—$C_3H_7$, —CH($CH_3$)—$CH_2$—CH($CH_3$)$_2$, —CH($CH_3$)—CH($CH_3$)—$C_2H_5$, —$CH_2$—CH($CH_3$)—CH($CH_3$)$_2$, —$CH_2$—C($CH_3$)$_2$—$C_2H_5$, —C($CH_3$)$_2$—$C_3H_7$, —C($CH_3$)$_2$—CH($CH_3$)$_2$, —$C_2H_4$—C($CH_3$)$_3$, —CH($CH_3$)—C($CH_3$)$_3$, —$CH_2$OH, —$C_2H_4$OH, —$C_3H_6$OH, —$C_4H_8$OH, —CH($CH_3$)—$C_2H_4$OH, —$C_5H_{10}$OH, —$CH_2$OCH$_3$, —$C_2H_4$OCH$_3$, —$C_3H_6$OCH$_3$, —$C_4H_8$OCH$_3$, —CH($CH_3$)—$C_2H_4$OCH$_3$, —$C_5H_{10}$OCH$_3$, —$CH_2NH_2$, —$C_2H_4NH_2$, —$C_3H_6NH_2$, —$C_4H_8NH_2$, —CH($CH_3$)—$C_2H_4NH_2$, —$C_6H_{10}NH_2$, —CH=$CH_2$, —$CH_2$—CH=$CH_2$, —C($CH_3$)=$CH_2$, —CH=CH—$CH_3$, —$C_2H_4$—CH=$CH_2$, —$CH_2$—CH=CH—$CH_3$, —CH=CH—$C_2H_5$, —$CH_2$—C($CH_3$)=$CH_2$, —CH($CH_3$)—CH=CH, —CH=C($CH_3$)$_2$, —C(CH₃)=CH—CH₃, —CH=CH—CH=CH₂, —C₃H₆—CH=CH₂, —C₂H₄—CH=CH—CH₃, —CH₂—CH=CH—C₂H₅, —CH=CH—C₃H₇, —CH₂—CH=CH—CH=CH₂, —CH=CH—CH=CH—CH₃, —CH=CH—CH₂—CH=CH₂, —C(CH₃)=CH—CH=CH₂, —CH=C(CH₃)—CH=CH₂, —CH=CH—C(CH₃)=CH₂, —C₂H₄—C(CH₃)=CH₂, —CH₂—CH(CH₃)—CH=CH₂, —CH(CH₃)—CH₂—CH=CH₂, —CH₂—CH=C(CH₃)₂, —CH₂—C(CH₃)=CH—CH₃, —CH(CH₃)—CH=CH—CH₃, —CH=CH—CH(CH₃)₂, —CH=C(CH₃)—C₂H₅, —C(CH₃)=CH—C₂H₅, —C(CH₃)=C(CH₃)₂, —C(CH₃)₂—CH=CH₂, —CH(CH₃)—C(CH₃)=CH₂, —C(CH₃)=CH—CH=CH₂, —CH=C(CH₃)—CH=CH₂, —CH=CH—C(CH₃)=CH₂, —C₄H₈—CH=CH₂, —C₃H₆—CH=CH—CH₃, —C₂H₄—CH=CH—C₂H₅, —CH₂—CH=CH—C₃H₇, —CH=CH—C₄H₉, —C₃H₆—C(CH₃)=CH₂, —C₂H₄—CH(CH₃)—CH=CH₂, —CH₂—CH(CH₃)—CH₂—CH=CH₂, —C₂H₄—CH=C(CH₃)₂, —CH(CH₃)—C₂H₄—CH=CH₂, —C₂H₄—C(CH₃)=CH—CH₃, —CH₂—CH(CH₃)—CH=CH—CH₃, —CH(CH₃)—CH₂—CH=CH—CH₃, —CH₂—CH=CH—CH(CH₃)₂, —CH₂—CH=C(CH₃)—C₂H₅, —CH₂—C(CH₃)=CH—C₂H₅, —CH=CH—CH(CH₃)—C₂H₅, —CH=CH—CH(CH₃)—C₂H₅, —CH=C(CH₃)—C₃H₇, —C(CH₃)=CH—C₃H₇, —CH₂—CH(CH₃)—C(CH₃)=CH₂, —C[C(CH₃)₃]=CH₂, —CH(CH₃)—CH₂—C(CH₃)=CH₂, —CH(CH₃)—CH(CH₃)—CH=CH₂, —CH=CH—C₂H₄—CH=CH₂, —CH₂—C(CH₃)₂—CH=CH₂, —C(CH₃)₂—CH₂—CH=CH₂, —CH₂—C(CH₃)=C(CH₃)₂, —CH(CH₃)—CH=C(CH₃)₂, —C(CH₃)₂—CH=CH—CH₃, —CH=CH—CH₂—CH=CH—CH₃, —CH(CH₃)—C(CH₃)=CH—CH₃, —CH=C(CH₃)—CH(CH₃)₂, —C(CH₃)=CH—CH(CH₃)₂, —C(CH₃)=C(CH₃)—C₂H₅, —CH=CH—C(CH₃)₃, —C(CH₃)₂—C(CH₃)=CH₂, —CH(C₂H₅)—C(CH₃)=CH₂, —C(CH₃)(C₂H₅)—CH=CH₂, —CH(CH₃)—C(C₂H₅)=CH₂, —CH₂—C(C₃H₇)=CH₂, —CH₂—C(C₂H₅)=CH—CH₃, —CH(C₂H₅)—CH=CH—CH₃, —C(C₄H₉)=CH₂, —C(C₃H₇)=CH—CH₃, —C(C₂H₅)=CH—C₂H₅, —C(C₂H₅)=C(CH₃)₂, —C[CH(CH₃)(C₂H₅)]=CH₂, —C[CH₂—CH(CH₃)₂]=CH₂, —C₂H₄—CH=CH—CH=CH₂, —CH₂—CH=CH—CH₂—CH=CH₂, —C₃H₆—C≡C—CH₃, —CH₂—CH=CH—CH=CH—CH₃, —CH=CH—CH=CH—C₂H₅, —CH₂—CH=CH—C(CH₃)=CH₂, —CH₂—C(CH₃)=CH—CH=CH₂, —CH₂—C(CH₃)=CH—CH=CH₂, —CH(CH₃)—CH₂—C≡CH, —CH(CH₃)—CH=CH—CH=CH₂, —CH=CH—CH₂—C(CH₃)=CH₂, —CH(CH₃)—C≡C—CH₃, —CH=CH—CH(CH₃)—CH=CH₂, —CH=C(CH₃)—CH₂—CH=CH₂, —C₂H₄—CH(CH₃)—C≡CH, —C(CH₃)=CH—CH₂—CH=CH₂, —CH=CH—CH=C(CH₃)₂, —CH₂—CH(CH₃)—CH₂—C≡CH, —CH=CH—C(CH₃)=CH—CH₃, —CH=C(CH₃)—CH=CH—CH₃, —CH₂—CH(CH₃)—C≡CH, —C(CH₃)=CH—CH=CH—CH₃, —CH=C(CH₃)—C(CH₃)=CH₂, —C(CH₃)=CH—C(CH₃)=CH₂, —C(CH₃)=C(CH₃)—CH=CH₂, —CH=CH—CH=CH—CH₂, —C≡CH, —C≡C—CH₃, —CH₂—C≡CH, —C₂H₄—C≡CH, —CH₂—C≡C—CH₃, —C≡C—C₂H₅, —C₃H₆—C≡CH, —C₂H₄—C≡C—CH₃, —CH₂—C≡C—C₂H₅, —C≡C—C₃H₇, —CH(CH₃)—C≡CH, —C₄H₈—C≡CH, —C₂H₄—C≡C—C₂H₅, —CH₂—C≡C—C₃H₇, —C≡C—C₄H₉, —C≡C—C(CH₃)₃, —CH(CH₃)—C₂H₄—C≡CH, —CH(CH₃)—CH=CH, —CH(CH₃)—CH₂—C≡C—CH₃, —C≡C—CH(CH₃)—C₂H₅, —CH₂C≡C—CH(CH₃)₂, —C≡C—CH(CH₃)—C₂H₅, —C≡C—CH₂CH(CH₃)₂, —CH(C₂H₅)—C≡C—CH₃, —C(CH₃)₂C≡C—CH₃, CH(C₂H₅)CH₂C≡CH, —CH₂CH(C₂H₅)—C≡CH, —C(CH₃)₂CH₂C≡CH, CH₂C(CH₃)₂—C≡CH, —CH(CH₃)CH(CH₃)—C≡CH, —CH(C₃H₇)—C≡CH, —C(CH₃)(C₂H₅)—C≡CH, —CH₂-Ph,

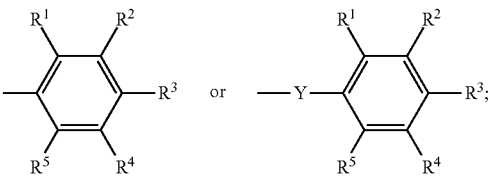

Y represents —CH₂—, —CH₂—CH₂—, —CH₂—CH₂—CH₂—, —CH=CH—, —CH=CH—CH₂—, —CH₂CH=CH—, —CHCH₃—, —CH—CH₃—CH₂—, —CH₂—CHCH₃—, —CH₂—CHCH₃—CH₂—, or —CH₂—O—CH₂—;

R^B represents

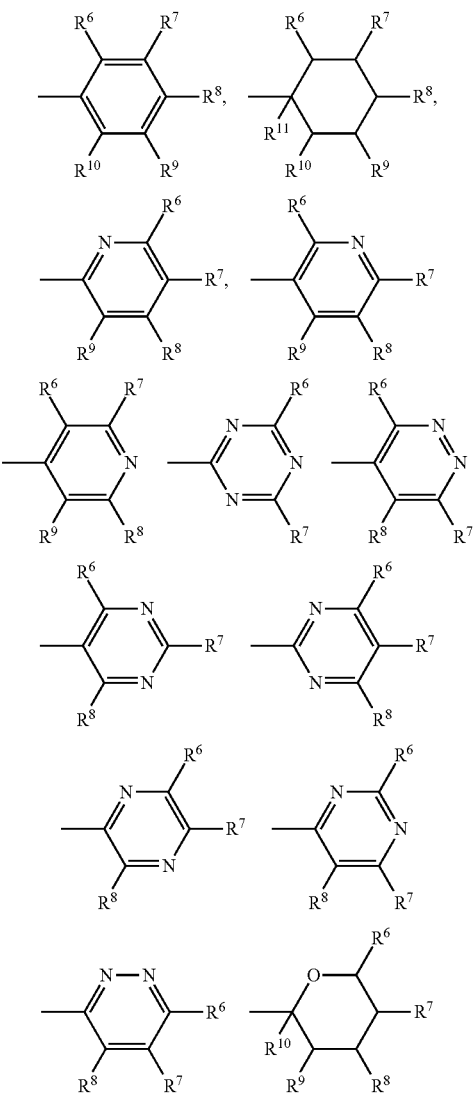

-continued
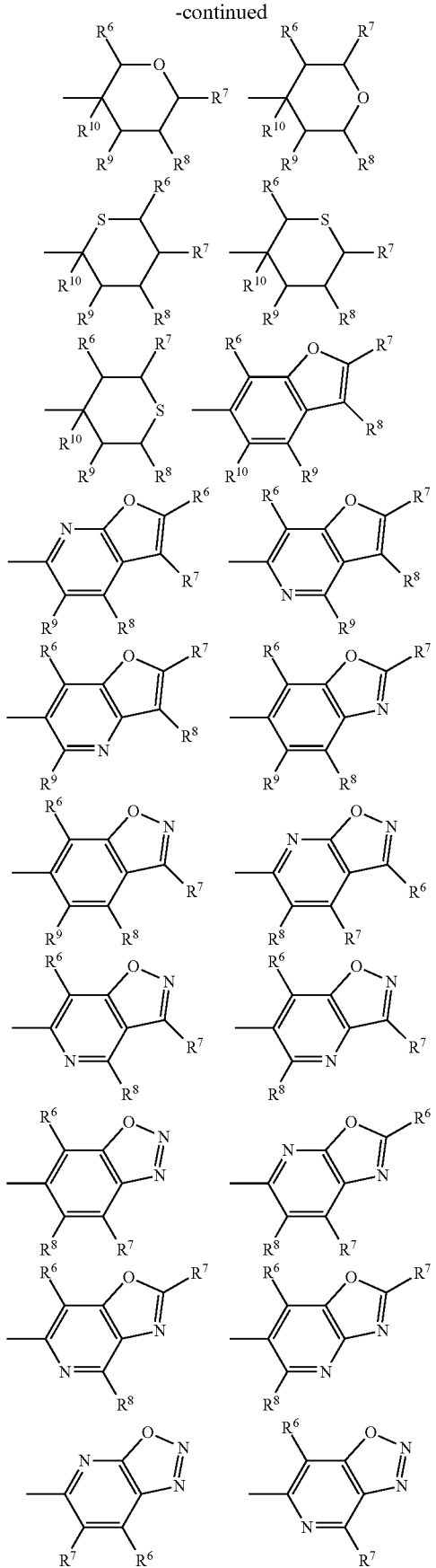
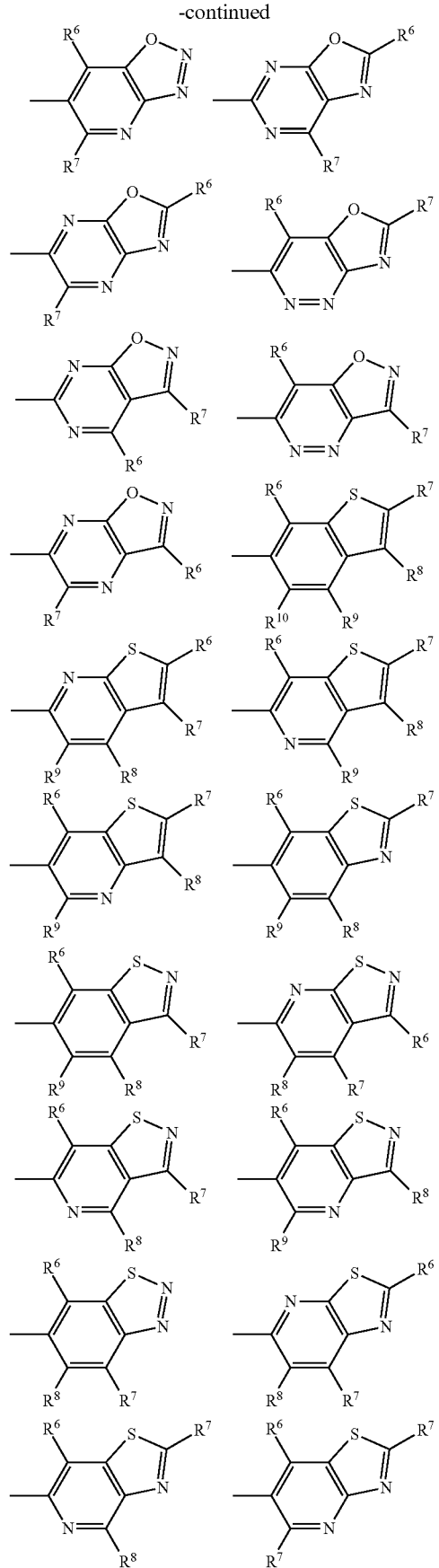

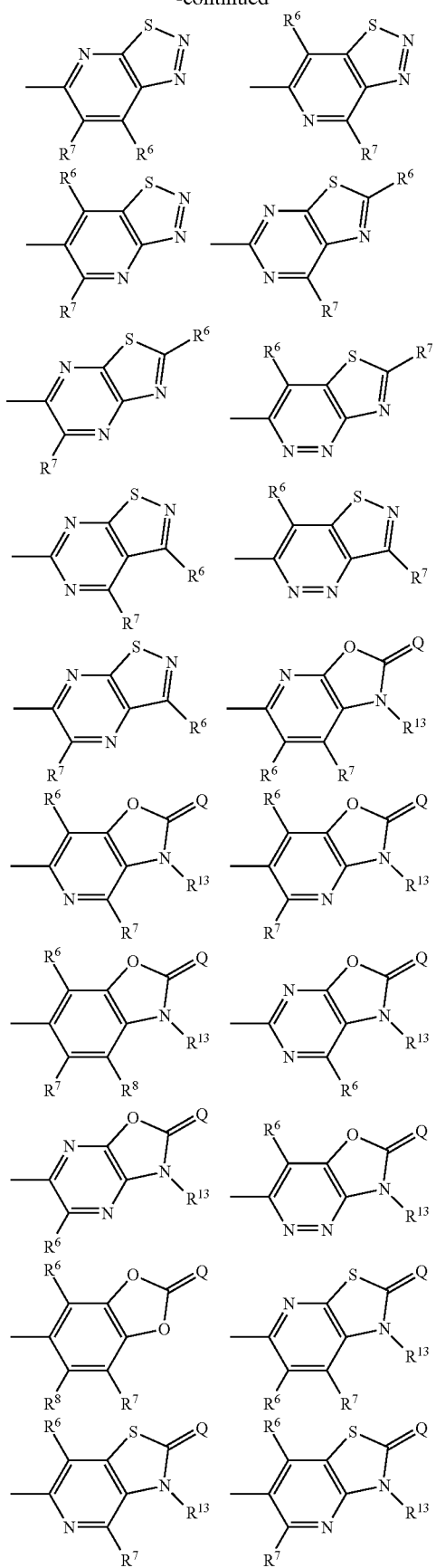
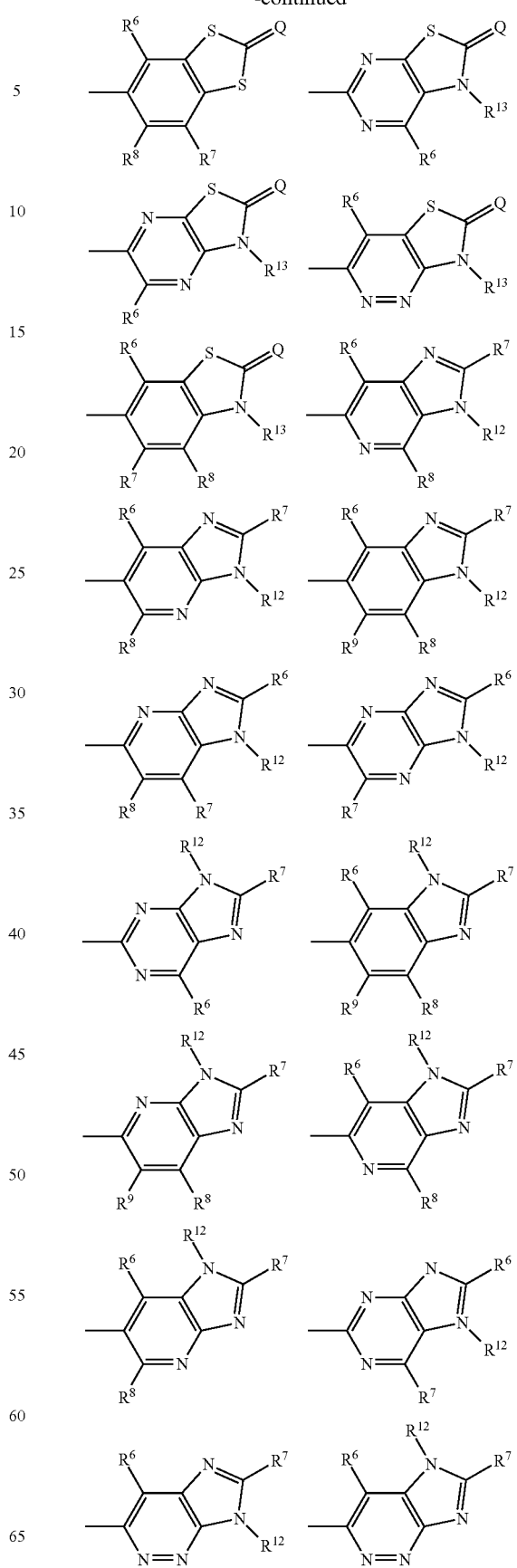

-continued
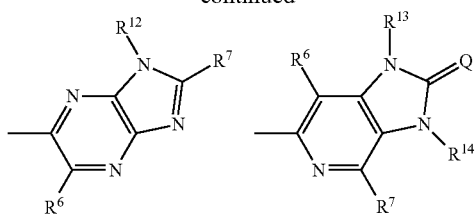
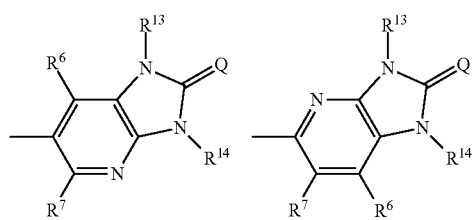
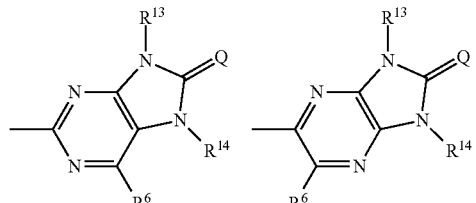
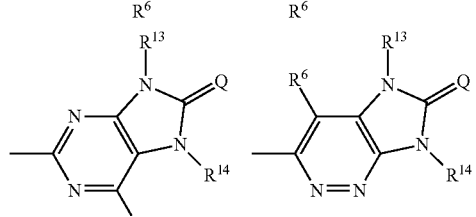
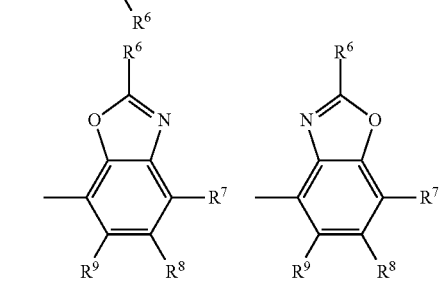
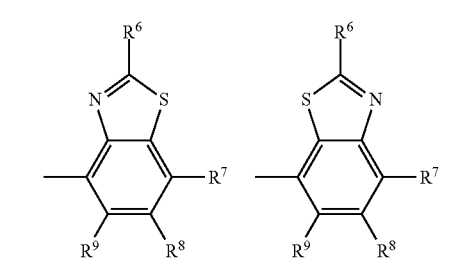
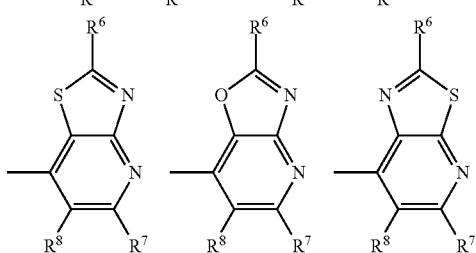
-continued
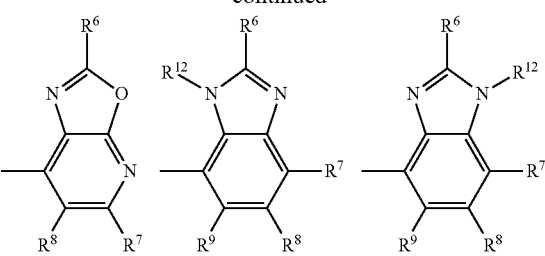
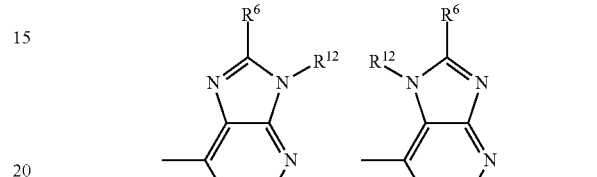
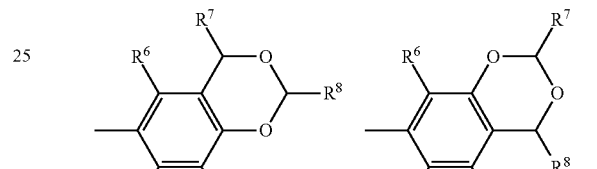
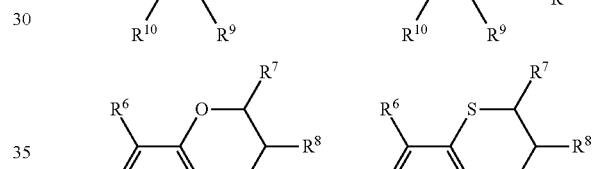
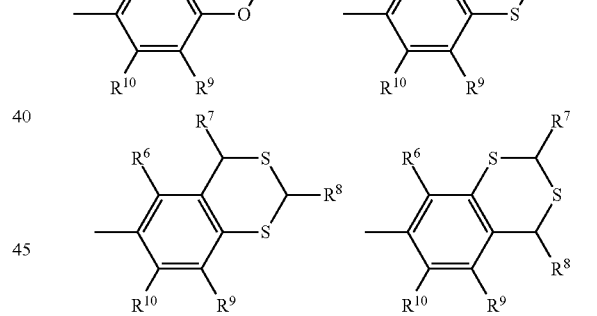
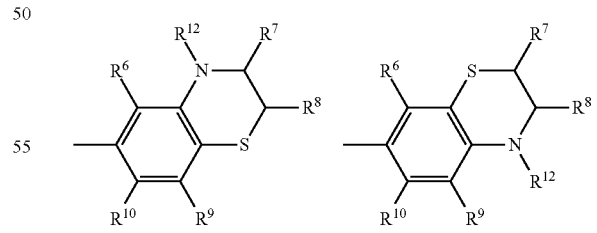
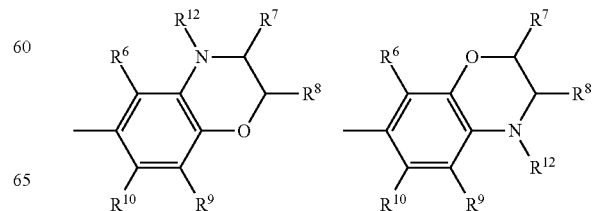

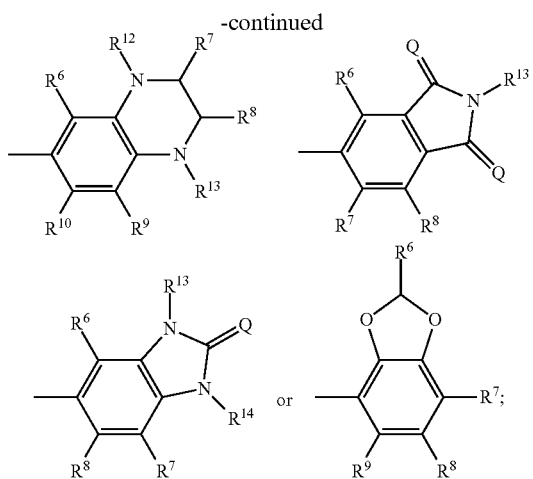

Q represents =O, =S, =N—R[12] or two hydrogen atoms forming a —CH$_2$— moiety together with the carbon atom to which Q is attached;

R[1]-R[11] represent independently of each other —H, —OH, —OCH$_3$, —OC$_2$H$_5$, —OC$_3$H$_7$, —O-cyclo-C$_3$H$_5$, —OCH(CH$_3$)$_2$, —OC(CH$_3$)$_3$, —OC$_4$H$_9$, —OCH$_2$—COOH, —OPh, —OCH$_2$-Ph, —OCPh$_3$, —CH$_2$—OCH$_3$, —CH$_2$—OH, —C$_2$H$_4$—OCH$_3$, —C$_3$H$_6$—OCH$_3$, —CH$_2$—OC$_2$H$_5$, —C$_2$H$_4$—OC$_2$H$_5$, —C$_3$H$_6$—OC$_2$H$_5$, —CH$_2$—OC$_3$H$_7$, —C$_2$H$_4$—OC$_3$H$_7$, —C$_3$H$_6$—OC$_3$H$_7$, —CH$_2$—O-cyclo-C$_3$H$_5$, —C$_2$H$_4$—O-cyclo-C$_3$H$_5$, —C$_3$H$_6$—O-cyclo-C$_3$H$_5$, —CH$_2$—OCH(CH$_3$)$_2$, —C$_2$H$_4$—OCH(CH$_3$)$_2$, —C$_3$H$_6$—OCH(CH$_3$)$_2$, —CH$_2$—OC(CH$_3$)$_3$, —C$_2$H$_4$—OC(CH$_3$)$_3$, —C$_3$H$_6$—OC(CH$_3$)$_3$, —CH$_2$—OC$_4$H$_9$, —C$_2$H$_4$—OC$_4$H$_9$, —C$_3$H$_6$—OC$_4$H$_9$, —CH$_2$—OPh, —C$_2$H$_4$—OPh, —C$_3$H$_6$—OPh, —CH$_2$—OCH$_2$-Ph, —C$_2$H$_4$—OCH$_2$-Ph, —C$_3$H$_6$—OCH$_2$-Ph, —SH, —SCH$_3$, —SC$_2$H$_5$, —SC$_3$H$_7$, —S-cyclo-C$_3$H$_5$, —SCH(CH$_3$)$_2$, —SC(CH$_3$)$_3$, —NO$_2$, —F, —Cl, —Br, —I, —P(O)(OH)$_2$, —P(O)(OCH$_3$)$_2$, —P(O)(OC$_2$H$_5$)$_2$, —P(O)(OCH(CH$_3$)$_2$)$_2$, —C(OH)[P(O)(OH)$_2$]$_2$, —Si(CH$_3$)$_2$(C(CH$_3$)$_3$), —Si(C$_2$H$_5$)$_3$, —Si(CH$_3$)$_3$, —N$_3$, —CN, —OCN, —NCO, —SCN, —NCS, —CHO, —COCH$_3$, —COC$_2$H$_5$, —COC$_3$H$_7$, —CO-cyclo-C$_3$H$_5$, —COCH(CH$_3$)$_2$, —COC(CH$_3$)$_3$, —COOH, —COCN, —COOCH$_3$, —COOC$_2$H$_5$, —COOC$_3$H$_7$, —COO-cyclo-C$_3$H$_5$, —COOCH(CH$_3$)$_2$, —COOC(CH$_3$)$_3$, —OOC—CH$_3$, —OOC—C$_2$H$_5$, —OOC—C$_3$H$_7$, —OOC-cyclo-C$_3$H$_5$, —OOC—CH(CH$_3$)$_2$, —OOC—C(CH$_3$)$_3$, —CONH$_2$, —CONHCH$_3$, —CONHC$_2$H$_5$, —CONHC$_3$H$_7$, —CONH-cyclo-C$_3$H$_5$, —CONH[CH(CH$_3$)$_2$], —CONH[C(CH$_3$)$_3$], —CON(CH$_3$)$_2$, —CON(C$_2$H$_5$)$_2$, —CON(C$_3$H$_7$)$_2$, —CON(cyclo-C$_3$H$_5$)$_2$, —CON[CH(CH$_3$)$_2$]$_2$, —CON[C(CH$_3$)$_3$]$_2$, —NHCOCH$_3$, —NHCOC$_2$H$_5$, —NHCOC$_3$H$_7$, —NHCO-cyclo-C$_3$H$_5$, —NHCO—CH(CH$_3$)$_2$, —NHCO—C(CH$_3$)$_3$, —NHCO—OCH$_3$, —NHCO—OC$_2$H$_5$, —NHCO—OC$_3$H$_7$, —NHCO—O-cyclo-C$_3$H$_5$, —NHCO—OCH(CH$_3$)$_2$, —NHCO—OC(CH$_3$)$_3$, —NH$_2$, —NHCH$_3$, —NHC$_2$H$_5$, —NHC$_3$H$_7$, —NH-cyclo-C$_3$H$_5$, —NHCH(CH$_3$)$_2$, —NHC(CH$_3$)$_3$, —N(CH$_3$)$_2$, —N(C$_2$H$_5$)$_2$, —N(C$_3$H$_7$)$_2$, —N(cyclo-C$_3$H$_5$)$_2$, —N[CH(CH$_3$)$_2$]$_2$, —N[C(CH$_3$)$_3$]$_2$, —SOCH$_3$, —SOC$_2$H$_5$, —SOC$_3$H$_7$, —SO-cyclo-C$_3$H$_5$, —SOCH(CH$_3$)$_2$, —SOC(CH$_3$)$_3$, —SO$_2$CH$_3$, —SO$_2$C$_2$H$_5$, —SO$_2$C$_3$H$_7$, —SO$_2$-cyclo-C$_3$H$_5$, —SO$_2$CH(CH$_3$)$_2$, —SO$_2$C(CH$_3$)$_3$, —SO$_3$H, —SO$_3$CH$_3$, —SO$_3$C$_2$H$_5$, —SO$_3$C$_3$H$_7$, —SO$_3$-cyclo-C$_3$H$_5$, —SO$_3$CH(CH$_3$)$_2$, —SO$_3$C(CH$_3$)$_3$, —SO$_2$NH$_2$, —SO$_2$NHCH$_3$, —SO$_2$NHC$_2$H$_5$, —SO$_2$NHC$_3$H$_7$, —SO$_2$NH-cyclo-C$_3$H$_5$, —SO$_2$NHCH(CH$_3$)$_2$, —SO$_2$NHC(CH$_3$)$_3$, —SO$_2$N(CH$_3$)$_2$, —SO$_2$N(C$_2$H$_5$)$_2$, —SO$_2$N(C$_3$H$_7$)$_2$, —SO$_2$N(cyclo-C$_3$H$_5$)$_2$, —SO$_2$N[CH(CH$_3$)$_2$]$_2$, —SO$_2$N[C(CH$_3$)$_3$]$_2$, —O—S(=O)CH$_3$, —O—S(=O)C$_2$H$_5$, —O—S(=O)C$_3$H$_7$, —O—S(=O)-cyclo-C$_3$H$_5$, —O—S(=O)CH(CH$_3$)$_2$, —O—S(=O)C(CH$_3$)$_3$, —S(=O)(=NH)CH$_3$, —S(=O)(=NH)C$_2$H$_5$, —S(=O)(=NH)C$_3$H$_7$, —S(=O)(=NH)-cyclo-C$_3$H$_5$, —S(=O)(=NH)CH(CH$_3$)$_2$, —S(=O)(=NH)C(CH$_3$)$_3$, —NH—SO$_2$—CH$_3$, —NH—SO$_2$—C$_2$H$_5$, —NH—SO$_2$—C$_3$H$_7$, —NH—SO$_2$-cyclo-C$_3$H$_5$, —NH—SO$_2$—CH(CH$_3$)$_2$, —NH—SO$_2$—C(CH$_3$)$_3$, —O—SO$_2$—CH$_3$, —O—SO$_2$—C$_2$H$_5$, —O—SO$_2$—C$_3$H$_7$, —O—SO$_2$-cyclo-C$_3$H$_5$, —O—SO$_2$—CH(CH$_3$)$_2$, —O—SO$_2$—C(CH$_3$)$_3$, —OCF$_3$, —CH$_2$—OCF$_3$, —C$_2$H$_4$—OCF$_3$, —C$_3$H$_6$—OCF$_3$, —OC$_2$F$_5$, —CH$_2$—OC$_2$F$_5$, —C$_2$H$_4$—OC$_2$F$_5$, —C$_3$H$_6$—OC$_2$F$_5$, —O—COOCH$_3$, —O—COOC$_2$H$_5$, —O—COOC$_3$H$_7$, —O—COO-cyclo-C$_3$H$_5$, —O—COOCH(CH$_3$)$_2$, —O—COOC(CH$_3$)$_3$, —NH—CO—NH$_2$, —NH—CO—NHCH$_3$, —NH—CO—NHC$_2$H$_5$, —NH—CS—N(C$_3$H$_7$)$_2$, —NH—CO—NHC$_3$H$_7$, —NH—CO—N(C$_3$H$_7$)$_2$, —NH—CO—NH[CH(CH$_3$)$_2$], —NH—CO—NH[C(CH$_3$)$_3$], —NH—CO—N(CH$_3$)$_2$, —NH—CO—N(C$_2$H$_5$)$_2$, —NH—CO—NH-cyclo-C$_3$H$_5$, —NH—CO—N(cyclo-C$_3$H$_5$)$_2$, —NH—CO—N[CH(CH$_3$)$_2$]$_2$, —NH—CS—N(C$_2$H$_5$)$_2$, —NH—CO—N[C(CH$_3$)$_3$]$_2$, —NH—CS—NHCH$_3$, —NH—CS—N(CH$_3$)$_2$, —NH—CS—NHC$_2$H$_5$, —NH—CS—NHC$_3$H$_7$, —NH—CS—NH-cyclo-C$_3$H$_5$, —NH—CS—NH[CH(CH$_3$)$_2$], —NH—CS—NH[C(CH$_3$)$_3$], —NH—CS—N(cyclo-C$_3$H$_5$)$_2$, —NH—CS—N[CH(CH$_3$)$_2$]$_2$, —NH—CS—N[C(CH$_3$)$_3$]$_2$, —NH—C(=NH)—NH$_2$, —NH—C(=NH)—NHCH$_3$, —NH—C(=NH)—NHC$_2$H$_5$, —NH—C(=NH)—NHC$_3$H$_7$, —O—CO—NH-cyclo-C$_3$H$_5$, —NH—C(=NH)—NH-cyclo-C$_3$H$_5$, —NH—C(=NH)—NH[CH(CH$_3$)$_2$], —O—CO—NH[CH(CH$_3$)$_2$], —NH—C(=NH)—NH[C(CH$_3$)$_3$], —NH—C(=NH)—N(CH$_3$)$_2$, —NH—C(=NH)—N(C$_2$H$_5$)$_2$, —NH—C(=NH)—N(C$_3$H$_7$)$_2$, —NH—C(=NH)—N(cyclo-C$_3$H$_5$)$_2$, —O—CO—NHC$_3$H$_7$, —NH—C(=NH)—N[CH(CH$_3$)$_2$]$_2$, —NH—C(=NH)—N[C(CH$_3$)$_3$]$_2$, —O—CO—NH$_2$, —O—CO—NHCH$_3$, —O—CO—NHC$_2$H$_5$, —O—CO—NH[C(CH$_3$)$_3$], —O—CO—N(CH$_3$)$_2$, —O—CO—N(C$_2$H$_5$)$_2$, —O—CO—N(C$_3$H$_7$)$_2$, —O—CO—N(cyclo-C$_3$H$_5$)$_2$, —O—CO—N[CH(CH$_3$)$_2$]$_2$, —O—CO—N[C(CH$_3$)$_3$]$_2$, —O—CO—OCH$_3$, —O—CO—OC$_2$H$_5$, —O—CO—OC$_3$H$_7$, —O—CO—O-cyclo-C$_3$H$_5$, —O—CO—OCH(CH$_3$)$_2$, —O—CO—OC(CH$_3$)$_3$, —CH$_2$F, —CHF$_2$, —CF$_3$, —CH$_2$Cl, —CH$_2$Br, —CH$_2$I, —CH$_2$—CH$_2$F, —CH$_2$—CHF$_2$, —CH$_2$—CF$_3$, —CH$_2$—CH$_2$Cl, —CH$_2$—CH$_2$Br, —CH$_2$—CH$_2$I, -cyclo-C$_3$H$_5$, -cyclo-C$_4$H$_7$, -cyclo-C$_5$H$_9$, -cyclo-C$_6$H$_{11}$, -cyclo-C$_7$H$_{13}$, -cyclo-C$_8$H$_{15}$, -Ph, —CH$_2$-Ph, —CH$_2$—CH$_2$-Ph, —CH=CH-Ph, —CPh$_3$, —CH$_3$, —C$_2$H$_5$, —C$_3$H$_7$, —CH(CH$_3$)$_2$, —C$_4$H$_9$, —CH$_2$—CH(CH$_3$)$_2$, —CH(CH$_3$)—C$_2$H$_5$, —C(CH$_3$)$_3$, —O$_5$H$_{11}$, —CH(CH$_3$)—C$_3$H$_7$, —CH$_2$—CH(CH$_3$)—C$_2$H$_5$, —CH(CH$_3$)—CH(CH$_3$)$_2$, —C(CH$_3$)$_2$—C$_2$H$_5$, —CH$_2$—C(CH$_3$)$_3$, —CH(C$_2$H$_5$)$_2$, —C$_2$H$_4$—CH(CH$_3$)$_2$, —C$_6$H$_{13}$, —C$_7$H$_{15}$, —O$_5$H$_{17}$, —C$_3$H$_6$—CH(CH$_3$)$_2$, —C$_2$H$_4$—CH(CH$_3$)—C$_2$H$_5$, —CH(CH$_3$)—C$_4$H$_9$, —CH$_2$—CH(CH$_3$)—C$_3$H$_7$, —CH(CH$_3$)—CH$_2$—CH(CH$_3$)$_2$, —CH(CH$_3$)—CH(CH$_3$)—C$_2$H$_5$, —CH$_2$—CH(CH$_3$)—CH(CH$_3$)$_2$, —CH$_2$—C(CH$_3$)$_2$—C$_2$H$_5$, —C(CH$_3$)$_2$—C$_3$H$_7$, —C(CH$_3$)$_2$—CH(CH$_3$)$_2$, —C$_2$H$_4$—C(CH$_3$)$_3$, —CH(CH$_3$)—C(CH$_3$)$_3$, —CH=CH$_2$, —CH$_2$—CH=CH$_2$, —C(CH$_3$)=CH$_2$, —CH=CH—CH$_3$, —C$_2$H$_4$—CH=CH$_2$, —CH$_2$—CH=CH—CH$_3$, —CH=CH—C$_2$H$_5$, —CH$_2$—C(CH$_3$)=CH$_2$, —CH(CH$_3$)—CH=CH, —CH=C(CH$_3$)$_2$, —C(CH$_3$)=CH—CH$_3$, —CH=CH—CH=CH$_2$, —C$_3$H$_6$—CH=CH$_2$, —C$_2$H$_4$—CH=CH—CH$_3$, —CH$_2$—CH=CH—C$_2$H$_5$, —CH=CH—C$_3$H$_7$, —CH$_2$—CH=CH—CH$_2$, —CH=CH—CH=CH$_3$, —CH=CH—CH$_2$—CH=CH$_2$, —C(CH$_3$)=CH—CH=CH$_2$, —CH=C(CH$_3$)—CH=CH$_2$, —CH=CH—C(CH$_3$)=CH$_2$, —C$_2$H$_4$—C(CH$_3$)=CH$_2$, —CH$_2$—CH(CH$_3$)—CH=CH$_2$, —CH(CH$_3$)—CH$_2$—CH=CH$_2$, —CH$_2$—CH=C(CH$_3$)$_2$, —CH$_2$—C(CH$_3$)=CH—CH$_3$, —CH(CH$_3$)—CH=CH—CH$_3$, —CH=CH—CH(CH$_3$)$_2$, —CH=C(CH$_3$)—C$_2$H$_5$, —C(CH$_3$)=CH—C$_2$H$_5$, —C(CH$_3$)=C(CH$_3$)$_2$, —C(CH$_3$)$_2$—CH=CH$_2$, —CH(CH$_3$)—C(CH$_3$)=CH$_2$, —C(CH$_3$)=CH—CH=CH$_2$, —CH=C(CH$_3$)—CH=CH$_2$, —CH=CH—C(CH$_3$)=CH$_2$, —C$_4$H$_8$—CH=CH$_2$, —C$_3$H$_6$—CH=CH—CH$_3$, —C$_2$H$_4$—CH=CH—C$_2$H$_5$, —CH$_2$—CH=CH—C$_3$H$_7$, —CH=CH—C$_4$H$_9$, —C$_3$H$_6$—C(CH$_3$)=CH$_2$, —C$_2$H$_4$—CH(CH$_3$)—CH=CH$_2$, —CH$_2$—CH(CH$_3$)—CH=CH$_2$, —C$_2$H$_4$—CH=C(CH$_3$)$_2$, —CH(CH$_3$)—C$_2$H$_4$—CH=CH$_2$, —C$_2$H$_4$—C(CH$_3$)=CH—CH$_3$, —CH$_2$—CH(CH$_3$)—CH=CH—CH$_3$, —CH(CH$_3$)—CH$_2$—CH=CH—CH$_3$, —CH$_2$—CH=CH—CH(CH$_3$)$_2$, —CH$_2$—CH=C(CH$_3$)—C$_2$H$_5$, —CH$_2$—C(CH$_3$)=CH—C$_2$H$_5$, —CH(CH$_3$)—CH=CH—C$_2$H$_5$, —CH=CH—CH$_2$—CH(CH$_3$)$_2$, —CH=CH—CH(CH$_3$)—C$_2$H$_5$, —CH=C(CH$_3$)—C$_3$H$_7$, —C(CH$_3$)=CH—C$_3$H$_7$, —CH$_2$—CH(CH$_3$)—C(CH$_3$)=CH$_2$, —C[C(CH$_3$)$_3$]=CH$_2$, —CH(CH$_3$)—CH$_2$—C(CH$_3$)=CH$_2$, —CH(CH$_3$)—CH(CH$_3$)—CH=CH$_2$, —CH$_2$—C(CH$_3$)$_2$—CH=CH$_2$, —C(CH$_3$)$_2$—CH$_2$—CH=CH$_2$, —CH$_2$—C(CH$_3$)=C(CH$_3$)$_2$, —CH(CH$_3$)—CH=C(CH$_3$)$_2$, —C(CH$_3$)$_2$—CH=CH—CH$_3$, —CH(CH$_3$)—C(CH$_3$)=CH—CH$_3$, —CH=C(CH$_3$)—CH(CH$_3$)$_2$, —C(CH$_3$)=CH—CH(CH$_3$)$_2$, —C(CH$_3$)=C(CH$_3$)—C$_2$H$_5$, —CH=CH—C(CH$_3$)$_3$, —C(CH$_3$)$_2$—C(CH$_3$)=CH$_2$, —CH(C$_2$H$_5$)—C(CH$_3$)=CH$_2$, —C(CH$_3$)(C$_2$H$_5$)—CH=CH$_2$, —CH(CH$_3$)—C(C$_2$H$_5$)=CH$_2$, —CH$_2$—C(C$_3$H$_7$)=CH$_2$, —CH$_2$—C(C$_2$H$_5$)=CH—CH$_3$, —CH(C$_2$H$_5$)—CH=CH—CH$_3$, —C(C$_4$H$_9$)=CH$_2$, —C(C$_3$H$_7$)=CH—CH$_3$, —C(C$_2$H$_5$)=CH—C$_2$H$_5$, —C(C$_2$H$_5$)=C(CH$_3$)$_2$, —C[CH(CH$_3$)(C$_2$H$_5$)]=CH$_2$, —C[CH$_2$—CH(CH$_3$)$_2$]=CH$_2$, —C$_3$H$_6$—C≡C—CH$_3$, —CH(CH$_3$)—CH$_2$—C≡CH, —CH(CH$_3$)—C≡C—CH$_3$, —C$_2$H$_4$—CH(CH$_3$)—C≡CH, —CH$_2$—CH(CH$_3$)—CH$_2$—C≡CH, —CH$_2$—CH(CH$_3$)—C≡CH, —C≡CH, —C≡C—CH$_3$, —CH$_2$—C≡CH, —C$_2$H$_4$—C≡CH, —CH$_2$—C≡C—CH$_3$, —C≡C—C$_2$H$_5$, —C$_3$H$_6$—C≡CH, —C$_2$H$_4$—C≡C—CH$_3$, —CH$_2$—C≡C—C$_2$H$_5$, —C≡C—C$_3$H$_7$, —CH(CH$_3$)—C≡CH, —C$_4$H$_5$—C≡CH, —C$_2$H$_4$—C≡C—C$_2$H$_5$, —CH$_2$—C≡C—C$_3$H$_7$, —C≡C—C$_4$H$_9$, —C≡C—C(CH$_3$)$_3$, —CH(CH$_3$)—C$_2$H$_4$—C≡CH, —CH$_2$—CH(CH$_3$)—C≡C—CH$_3$, —CH(CH$_3$)—CH$_2$—C≡C—CH$_3$, —CH(CH$_3$)—C≡C—C$_2$H$_5$, —CH$_2$—C≡C—CH(CH$_3$)$_2$, —C≡C—CH(CH$_3$)$_2$, —C≡C—CH$_2$—CH(CH$_3$)$_2$, —CH(C$_2$H$_5$)—C≡C—CH$_3$, —C(CH$_3$)$_2$—C≡C—CH$_3$, —CH(C$_2$H$_5$)—CH$_2$—C≡CH, —CH$_2$—CH(C$_2$H$_5$)—C≡CH, —C(CH$_3$)$_2$—CH$_2$—C≡CH, —CH$_2$—C(CH$_3$)$_2$—C≡CH, —CH(CH$_3$)—CH(CH$_3$)—C≡CH, —CH(C$_3$H$_7$)—C≡CH, —C(CH$_3$)(C$_2$H$_5$)—C≡CH, or —CH$_2$—CH(C≡CH)$_2$;

R$^{12}$-R$^{14}$ represent independently of each other —H, —CH$_2$F, —CHF$_2$, —CH$_2$—OCH$_3$, —CH$_2$—OH, —C$_2$H$_4$—OCH$_3$, —C$_3$H$_6$—OCH$_3$, —CH$_2$—OC$_2$H$_5$, —C$_2$H$_4$—OC$_2$H$_5$, —C$_3$H$_6$—OC$_2$H$_5$, —CH$_2$—OC$_3$H$_7$, —C$_2$H$_4$—OC$_3$H$_7$, —C$_3$H$_6$—OC$_3$H$_7$, —CH$_2$—O-cyclo-C$_3$H$_5$, —C$_2$H$_4$—O-cyclo-C$_3$H$_5$, —C$_3$H$_6$—O-cyclo-C$_3$H$_5$, —CH$_2$—OCH(CH$_3$)$_2$, —C$_2$H$_4$—OCH(CH$_3$)$_2$, —C$_3$H$_6$—OCH(CH$_3$)$_2$, —CH$_2$—OC(CH$_3$)$_3$, —C$_2$H$_4$—OC(CH$_3$)$_3$, —C$_3$H$_6$—OC(CH$_3$)$_3$, —CH$_2$—OC$_4$H$_9$, —C$_2$H$_4$—OC$_4$H$_9$, —C$_3$H$_6$—OC$_4$H$_9$, —CH$_2$—OPh, —C$_2$H$_4$—OPh, —C$_3$H$_6$—OPh, —CH$_2$—OCH$_2$-Ph, —C$_2$H$_4$—OCH$_2$-Ph, —C$_3$H$_6$—OCH$_2$-Ph, —CF$_3$, —CH$_2$Cl, —CH$_2$Br, —CH$_2$I, —CH$_2$—CH$_2$F, —CH$_2$—CHF$_2$, —CH$_2$—CF$_3$, —CH$_2$—CH$_2$Cl, —CH$_2$—CH$_2$Br, —CH$_2$—CH$_2$I, -cyclo-C$_3$H$_5$, -cyclo-C$_4$H$_7$, -cyclo-C$_5$H$_9$, -cyclo-C$_6$H$_{11}$, -cyclo-C$_7$H$_{13}$, -cyclo-C$_8$H$_{15}$, -Ph, —CH$_2$-Ph, —CH$_2$—CH$_2$-Ph, —CH=CH-Ph, —CPh$_3$, —CH$_3$, —C$_2$H$_5$, —C$_3$H$_7$, —CH(CH$_3$)$_2$, —C$_4$H$_9$, —CH$_2$—CH(CH$_3$)$_2$, —CH(CH$_3$)—C$_2$H$_5$, —C(CH$_3$)$_3$, —C$_5$H$_{11}$, —CH(CH$_3$)—C$_3$H$_7$, —CH$_2$—CH(CH$_3$)—C$_2$H$_5$, —CH(CH$_3$)—CH(CH$_3$)$_2$, —C(CH$_3$)$_2$—C$_2$H$_5$, —CH$_2$—C(CH$_3$)$_3$, —CH(C$_2$H$_5$)$_2$, —C$_2$H$_4$—CH(CH$_3$)$_2$, —C$_6$H$_{13}$, —C$_7$H$_{15}$, —C$_8$H$_{17}$, —C$_3$H$_6$—CH(CH$_3$)$_2$, —C$_2$H$_4$—CH(CH$_3$)—C$_2$H$_5$, —CH(CH$_3$)—C$_4$H$_9$, —CH$_2$—CH(CH$_3$)—C$_3$H$_7$, —CH(CH$_3$)—CH$_2$—CH(CH$_3$)$_2$, —CH(CH$_3$)—CH(CH$_3$)—C$_2$H$_5$, —CH$_2$—CH(CH$_3$)—CH(CH$_3$)$_2$, —CH$_2$—C(CH$_3$)$_2$—C$_2$H$_5$, —C(CH$_3$)$_2$—C$_3$H$_7$, —C(CH$_3$)$_2$—CH(CH$_3$)$_2$, —C$_2$H$_4$—C(CH$_3$)$_3$, —CH(CH$_3$)—C(CH$_3$)$_3$, —CH=CH$_2$, —CH$_2$—CH=CH$_2$, —C(CH$_3$)=CH$_2$, —CH=CH—CH$_3$, —C$_2$H$_4$—CH=CH$_2$, —CH$_2$—CH=CH—CH$_3$, —CH=CH—C$_2$H$_5$, —CH$_2$—C(CH$_3$)=CH$_2$, —CH(CH$_3$)—CH=CH, —CH=C(CH$_3$)$_2$, —C(CH$_3$)=CH—CH$_3$, —CH=CH—CH=CH$_2$, —C$_3$H$_6$—CH=CH$_2$, —C$_2$H$_4$—CH=CH—CH$_3$, —CH$_2$—CH=CH—C$_2$H$_5$, —CH=CH—C$_3$H$_7$, —CH=CH—CH—CH$_3$, —CH=CH—CH$_2$—CH=CH$_2$, —C(CH$_3$)=CH—CH=CH$_2$, —CH=C(CH$_3$)—CH=CH$_2$, —CH=CH—C(CH$_3$)=CH$_2$, —C$_2$H$_4$—C(CH$_3$)=CH$_2$, —CH$_2$—CH(CH$_3$)—CH=CH$_2$, —CH(CH$_3$)—CH$_2$—CH=CH$_2$, —CH$_2$—CH=C(CH$_3$)$_2$, —CH$_2$—C(CH$_3$)=CH—CH$_3$, —CH(CH$_3$)—CH=CH—CH$_3$, —CH=CH—CH(CH$_3$)$_2$, —CH=C(CH$_3$)—C$_2$H$_5$, —C(CH$_3$)=CH—C$_2$H$_5$, —C(CH$_3$)=C(CH$_3$)$_2$, —C(CH$_3$)$_2$—CH=CH$_2$, —CH(CH$_3$)—C(CH$_3$)=CH$_2$, —C(CH$_3$)=CH—CH=CH$_2$, —CH=C(CH$_3$)—CH=CH$_2$, —CH=CH—C(CH$_3$)=CH$_2$, —C$_4$H$_8$—CH=CH$_2$, —C$_3$H$_6$—CH=CH—CH$_3$, —C$_2$H$_4$—CH=CH—C$_2$H$_5$, —CH$_2$—CH=CH—C$_3$H$_7$, —CH=CH—C$_4$H$_9$, —C$_3$H$_6$—C(CH$_3$)=CH$_2$, —C$_2$H$_4$—CH(CH$_3$)—CH=CH$_2$, —CH$_2$—CH(CH$_3$)—CH=CH$_2$, —C$_2$H$_4$—CH=C(CH$_3$)$_2$, —CH(CH$_3$)—C$_2$H$_4$—CH=CH$_2$, —C$_2$H$_4$—C(CH$_3$)=CH—CH$_3$, —CH$_2$—CH(CH$_3$)—CH=CH—CH$_3$, —CH(CH$_3$)—CH$_2$—CH=CH—CH$_3$, —CH$_2$—CH=CH—CH(CH$_3$)$_2$, —CH$_2$—CH=C(CH$_3$)—C$_2$H$_5$, —CH$_2$—C(CH$_3$)=CH—C$_2$H$_5$, —CH(CH$_3$)—CH=CH—C$_2$H$_5$, —CH=CH—CH$_2$—CH(CH$_3$)$_2$, —CH=CH—CH(CH$_3$)—C$_2$H$_5$, —CH=C(CH$_3$)—C$_3$H$_7$, —C(CH$_3$)=CH—C$_3$H$_7$, —CH$_2$—CH(CH$_3$)—C(CH$_3$)=CH$_2$, —C[C(CH$_3$)$_3$]=CH$_2$, —CH(CH$_3$)—CH$_2$—C(CH$_3$)=CH$_2$, —CH(CH$_3$)—CH(CH$_3$)—CH=CH$_2$, —CH$_2$—C(CH$_3$)$_2$—CH=CH$_2$, —C(CH$_3$)$_2$—CH$_2$—CH=CH$_2$, —CH$_2$—C(CH$_3$)=C(CH$_3$)$_2$, —CH(CH$_3$)—CH=C(CH$_3$)$_2$, —C(CH$_3$)$_2$—CH=CH—CH$_3$, —CH(CH$_3$)—C(CH$_3$)=CH—CH$_3$, —CH=C(CH$_3$)—CH(CH$_3$)$_2$, —C(CH$_3$)=CH—CH(CH$_3$)$_2$, —C(CH$_3$)=C(CH$_3$)—C$_2$H$_5$, —CH=CH—C(CH$_3$)$_3$, —C(CH$_3$)$_2$—C(CH$_3$)=CH$_2$, —CH(C$_2$H$_5$)—C(CH$_3$)=CH$_2$, —C(CH$_3$)(C$_2$H$_5$)—CH=CH$_2$, —CH(CH$_3$)—C(C$_2$H$_5$)=CH$_2$, —CH$_2$—C(C$_3$H$_7$)=CH$_2$, —CH$_2$—C(C$_2$H$_5$)=CH—CH$_3$, —CH(C$_2$H$_5$)—CH=CH—CH$_3$, —C(C$_4$H$_9$)=CH$_2$, —C(C$_3$H$_7$)=CH—CH$_3$, —C(C$_2$H$_5$)=CH—C$_2$H$_5$, —C(C$_2$H$_5$)=C(CH$_3$)$_2$, —C[CH(CH$_3$)(C$_2$H$_5$)]=CH$_2$, —C[CH$_2$—CH(CH$_3$)$_2$]=CH$_2$, —C$_3$H$_6$—C≡C—CH$_3$, —CH(CH$_3$)—CH$_2$—C≡CH, —CH(CH$_3$)—C≡C—CH$_3$, —C$_2$H$_4$—CH(CH$_3$)—C≡CH, —CH$_2$—CH(CH$_3$)—C≡CH, —CH$_2$—CH(CH$_3$)—C≡CH, —C≡CH, —C≡C—CH$_3$, —CH$_2$—C≡CH, —C$_2$H$_4$—C≡CH, —CH$_2$—C≡C—CH$_3$, —C≡C—C$_2$H$_5$, —C$_3$H$_6$—C≡CH, —C$_2$H$_4$C≡C—CH$_3$, —CH$_2$—C≡C—C$_2$H$_5$, —C≡C—C$_3$H$_7$, —CH(CH$_3$)—C≡CH, —C$_4$H$_8$C≡CH, —C$_2$H$_4$—C≡C—C$_2$H$_5$, —CH$_2$—C≡C—C$_3$H$_7$, —C≡C—C$_4$H$_9$, —C≡CC(CH$_3$)$_3$, CH(CH$_3$)C$_2$H$_4$C≡CH, CH$_2$CH(CH$_3$)C≡CCH$_3$, —CH(CH$_3$)—CH$_2$—C≡C—CH$_3$, —CH(CH$_3$)—C≡C—C$_2$H$_5$, CH$_2$C≡C—CH(CH$_3$)$_2$, —C≡C—CH(CH$_3$)—C$_2$H$_5$, —C≡C—CH$_2$—CH(CH$_3$)$_2$, —CH(C$_2$H$_5$)—C≡C—CH$_3$, —C(CH$_3$)$_2$—C≡C—CH$_3$, —CH(C$_2$H$_5$)CH$_2$C≡CH, —CH$_2$—CH(C$_2$H$_5$)—C≡CH, —C(CH$_3$)$_2$—CH$_2$—C≡CH, —CH$_2$C(CH$_3$)$_2$C≡CH, —CH(CH$_3$)—CH(CH$_3$)—C≡CH, —CH(C$_3$H$_7$)—C≡CH, —C(CH$_3$)(C$_2$H$_5$)—C≡CH, or —CH$_2$—CH(C≡CH)$_2$;

and enantiomers, stereoisomeric forms, mixtures of enantiomers, anomers, deoxy-forms, diastereomers, mixtures of diastereomers, prodrugs, tautomers, hydrates, solvates and racemates of the above mentioned compounds and pharmaceutically acceptable salts thereof with the proviso that the compound of the formula (I) is not 9-(4-chlorophenylsulfonyl)-3,9-diazabicyclo[3.3.1]nonan-2-one.

Excluded from the present invention and from the claimed scope are also compounds wherein R$^A$ is an aryl group such as phenyl. Compounds of general formula (I), wherein an aryl group is directly bonded to the nitrogen atom in the ring system did not show any potent inhibitory effect in regard to FKBP51 and FKBP52 (R$^A$=Ph, K$_i$ value for FKBP51 and FKBP52>100 µM). The same is true for compounds wherein R$^A$ represents an alkyl group (R$^A$=Et, K$_i$ value for FKBP51 and FKBP52>100 µM). Thus is was surprisingly found that R$^A$ has to represent an alkylaryl group or an alkyloxyaryl group in order to obtain compounds which are potent FKBP51 and FKBP52 inhibitors.

The expression prodrug is defined as a pharmacological substance, a drug, which is administered in an inactive or significantly less active form. Once administered, the prodrug is metabolized in the body in vivo into the active compound.

The expression tautomer is defined as an organic compound that is interconvertible by a chemical reaction called tautomerization. Tautomerization can be catalyzed preferably by bases or acids or other suitable compounds.

Very preferred substituents for R$^A$ are:

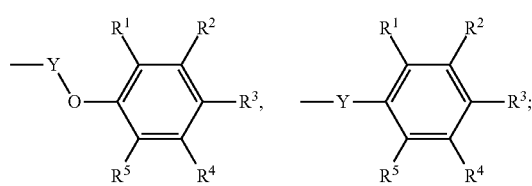

wherein Y has the meanings as defined herein.

Specifically preferred are compounds of the formula (I) having one of the following substituents R$^A$,

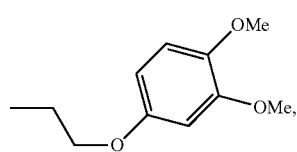

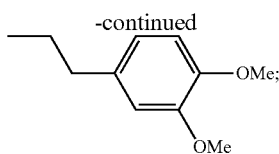

Preferred substituents for R$^B$ are:

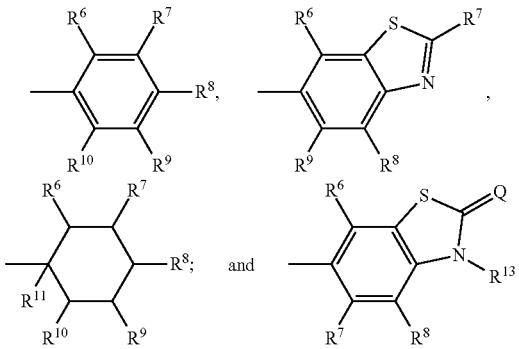

Particularly preferred are compounds of the formula (I) having one of the following substituents R$^B$

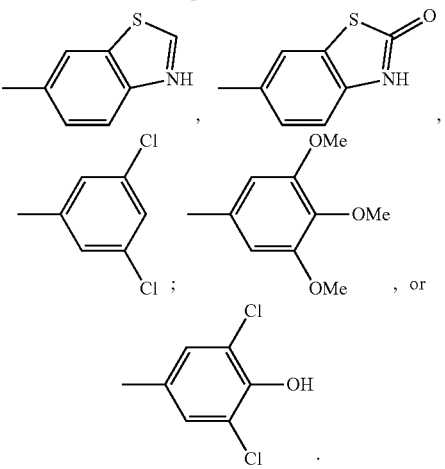

Preferred substituents for R$^1$-R$^{11}$ are: —H, —OH, —OCH$_3$, —OC$_2$H$_5$, —OC$_3$H$_7$, —OCH(CH$_3$)$_2$, —OCPh$_3$, —CH$_2$—OCH$_3$, —CH$_2$—OH, —OC$_3$H$_7$, —OC(CH$_3$)$_3$, —OCH$_2$—COOH, —CH$_3$, —CH$_2$—OH, —C$_2$H$_5$, —C$_3$H$_7$, —CH(CH$_3$)$_2$, —F, —Cl, —Br, —I;

Especially preferred are compounds of the formula (II) and (III):

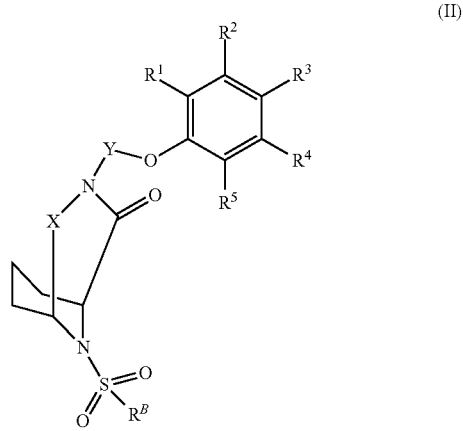

(II)

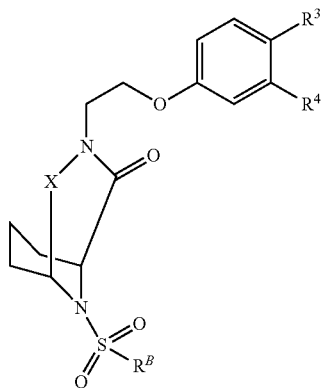

(III)

wherein X, Y, $R^B$ and the substituents $R^1$-$R^5$ have the meanings as defined herein.

In these formula (II) and (III) $R^B$ represents preferably

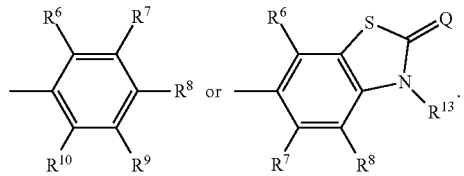

The compounds falling under general formula (I)-(VIII) are novel so that the present invention also relates to compounds of the general formula (I)-(VIII) as well as enantiomers, stereoisomeric forms, mixtures of enantiomers, anomers, diastereomers, mixtures of diastereomers, tautomers, hydrates, solvates and racemates and pharmaceutically acceptable salts of these compounds.

Further preferred are the general formula (IV), (V) and (VI):

(IV)

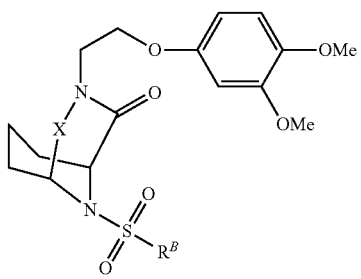

(VI)

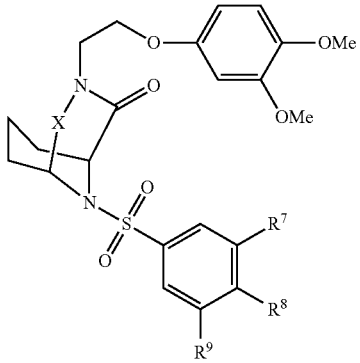

(V)

wherein X and the substituents $R^B$ and $R^7$-$R^9$ have the meanings as defined herein.

Yet further preferred are the general formula (VII) and (VIII):

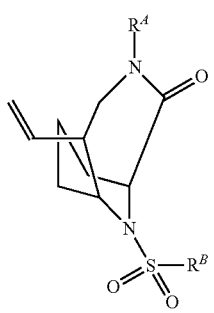

(VII)

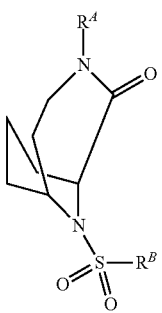

(VIII)

wherein the substituents $R^A$ and $R^B$ have the meanings as defined herein.

However, particularly preferred are compounds of general formula (VII):

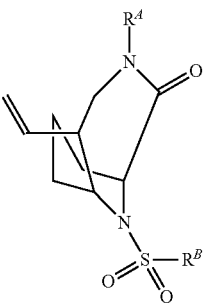

(VII)

wherein the substituents $R^A$ and $R^B$ have the meanings as defined herein.

Particularly preferred are compounds of formula (VII), wherein $R^A$ represents —H,

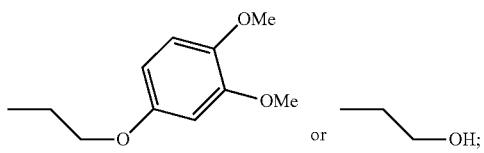

and/or wherein $R^B$ represents

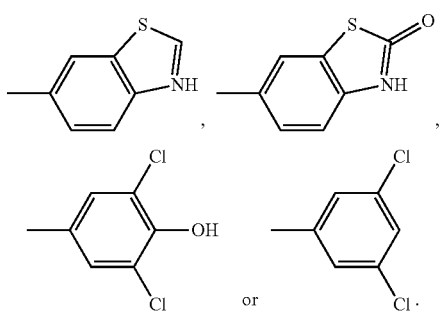

In yet another preferred embodiment of the present invention, the compound according to the general formula (I) is selected from the group comprising or consisting of:

9-(3,5-dichlorophenylsulfonyl)-3-(2-(3,4-dimethoxyphenoxyl)ethyl)-3,9-diazabicyclo[3.3.1]nonan-2-one 4b 9-(benzo[d]thiazol-6-ylsulfonyl)-3-(2-(3,4-dimethoxyphenoxyl)ethyl)-3,9-diazabicyclo[3.3.1]nonan-2-one 4c 6-(3-(2-(3,4-dimethoxyphenoxyl)ethyl)-2-oxo-3,9-diazabicyclo[3.3.1]nonan-9-ylsulfonyl)benzo[d]thiazol-2(3H)-one 4d 6-(2-oxo-3,9-diazabicyclo[3.3.1]nonan-9-ylsulfonyl)benzo[d]thiazol-2(3H)-one 4e 10-(3,5-dichlorophenylsulfonyl)-3-(2-(3,4-dimethoxyphenoxy)ethyl)-3,10-diazabicyclo[4.3.1]decan-2-one 5b 10-(benzo[d]thiazol-6-ylsulfonyl)-3-(2-(3,4-dimethoxyphenoxyl)ethyl)-3,10-diazabicyclo[4.3.1]decan-2-one 5c 6-(3-(2-(3,4-dimethoxyphenoxy)ethyl)-2-oxo-3,10-diazabicyclo[4.3.1]decan-10-ylsulfonyl)benzo[d]thiazol-2(3H)-one 5d 6-(2-oxo-3,10-diazabicyclo[4.3.1]decan-10-ylsulfonyl)benzo[d]thiazol-2(3H)-one 5e 10-(3,5-dichloro-4-hydroxyphenylsulfonyl)-3-(2-(3,4-dimethoxyphenoxyl)ethyl)-3,10-diazabicyclo[4.3.1]decan-2-one 5i and (1S,5S,6R)-10-(3,5-dichlorophenylsulfonyl)-3-(2-(3,4-dimethoxyphenoxyl)ethyl)-5-vinyl-3,10-diazabicyclo[4.3.1]decan-2-one 5k.

Another aspect of the present invention refers to the synthesis of the compounds of the formula (I)

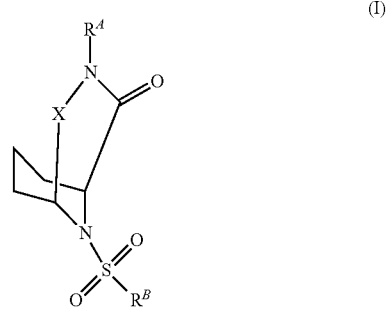

wherein X and the substituents $R^A$ and $R^B$ have the meanings as defined herein.

Specifically the compounds of the general formula (I) can be prepared according to the following synthetic route I:

Synthetic Route I

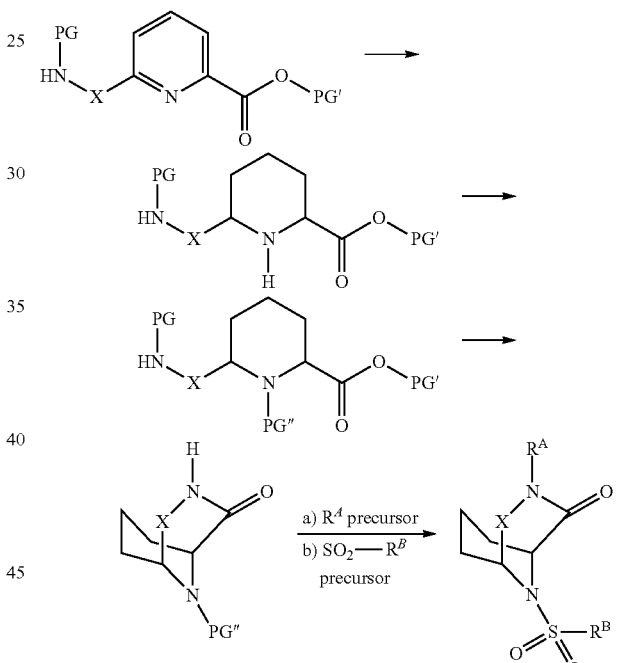

wherein X represents —$CH_2$— or —$CH_2$—$CH_2$— and the substituents $R^A$ and $R^B$ have the meanings as defined herein, $R^A$ precursor and $SO_2$—$R^B$ precursor refer to active species of the respective compounds being suitable of transferring the substituents $R^A$ and $R^B$ via chemical bond to another molecule or atom. Thus the term "$R^A$ precursor" refers to a reagent containing the chemical moiety $R^A$ so that under the reaction conditions this reagent transfers the moiety $R^A$ to the above shown molecule of the general formula (I). The $R^A$ precursor reacts with the above shown intermediate product, wherein the amino group in the six-membered cycle is protected by PG" and the amide nitrogen is unprotected in order to introduce the residue —$R^A$ by covalent chemical bonding into the intermediate product.

Consequently the term "$SO_2$—$R^B$ precursor" refers to a reagent containing the chemical moiety $SO_2$—$R^B$ so that under the reaction conditions this reagent transfers the moiety $SO_2$—$R^B$ to the above shown molecule of the general formula (I). The $SO_2$—$R^B$ precursor reacts with the above shown intermediate product wherein the amino group in the six-membered cycle is deprotected (i.e. PG" is replaced by hydrogen) and the amide nitrogen is protected or modified by the residue $R^A$ in order to introduce the residue —$SO_2$—$R^B$ by covalent chemical bonding into the intermediate product.

PG and PG" refer to commonly used protecting groups for amines and PG' refers to a protecting group for carboxyl groups such as esters.

Further, the compounds of the general formula (I) can be prepared according to the following synthetic route II comprising the following steps as defined below. Accordingly, compounds of the general formula (I), wherein X represents —CH(CH=CH$_2$)— or —CH(CH=CH$_2$)—CH$_2$—, can be prepared be providing 6-carboxy-2-piperidone and a precursor molecule for the moiety $R^A$ which has a suitable leaving group (LG) such as trimethylsilyl and a carbon-carbon double bond in vinyl or allyl position to the $R^A$ amino group. Said $R^A$ amino group is reacted with the carboxy moiety of 6-carboxy-2-piperidone yielding compound (IX). Subsequently, compound (IX) is protected with a suitable amine protection group PG''' furnishing compound (X). Compound (X) undergoes a cyclization reaction upon which the leaving group LG is detached from the starting molecule yielding intermediate compound (XI). Performing a suitable deprotection reaction amine intermediate (XII) is formed, which can subsequently be reacted with a suitable precursor for the moiety —$SO_2$—$R^B$ yielding compounds of the general formula (I), wherein X represents —CH(CH=CH$_2$)— or —CH(CH=CH$_2$)—CH$_2$—.

Synthetic Route II

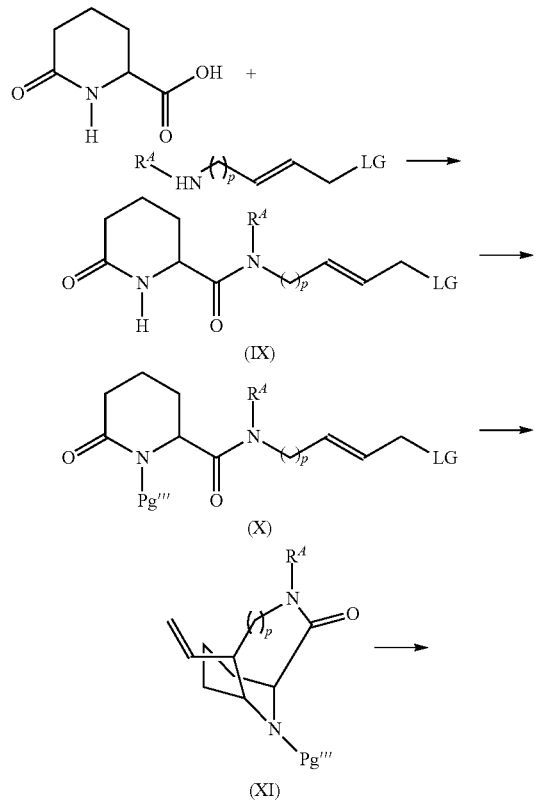

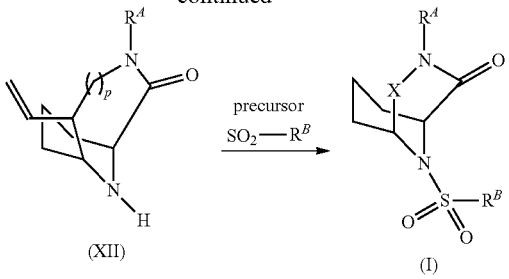

providing a compound of formula (X),
performing a cyclization reaction to yield compounds of formula (XI),
deprotecting (XI) to yield intermediate compounds of formula (XII), and
introducing the moiety —$SO_2$—$R^B$ to yield compounds of formula (I), wherein X represents —CH(CH=CH$_2$)— or —CH(CH=CH$_2$)—CH$_2$—, and
wherein the substituents $R^A$ and $R^B$ have the meanings as defined herein, p is 0 or 1, $SO_2$—$R^B$ precursor refers to active species of the respective compounds being suitable of transferring the substituent $SO_2$—$R^B$ via chemical bond to another molecule or atom, LG refers to a leaving group suitable such as trimethylsilyl, and PG''' refers to commonly used protecting group for amines. The term $SO_2$—$R^B$ precursor has the same meaning as defined in synthetic route I. Thus the term "$SO_2$—$R^B$ precursor" refers to a reagent containing the chemical moiety $SO_2$—$R^B$ so that under the reaction conditions this reagent transfers the moiety $SO_2$—$R^B$ to the above shown molecule of the general formula (XII). The $SO_2$—$R^B$ precursor reacts with the amino group of the above shown intermediate product (XII) in order to introduce the residue —$SO_2$—$R^B$ by covalent chemical bonding into the intermediate product to obtain the inventive compounds of general formula (I).

Suitable protecting groups PG, PG" and PG''' for amines are carbobenzyloxy (Cbz), p-methoxybenzyl carbonyl (Moz), tert-butyloxycarbonyl (Boc), 9-fluorenylmethyloxycarbonyl (Fmoc), allyloxycarbonyl (Alloc), 2,2,2-trichlorethoxycarbonyl (Troc), and 2-(trimethylsilyl)ethoxycarbonyl (Teoc).

The present invention also comprises pharmaceutically acceptable salts of the compounds according to the general formula (I), (II), (III), (IV), (V), (VI), (VII) and (VIII), all stereoisomeric forms of the compounds according to at least one of the general formula (I) to (VIII), as well as solvates, especially hydrates or prodrugs thereof.

In case the compounds of the present invention bear basic and/or acidic substituents (the compounds are definitely basic; in addition the compounds may bear acidic substituents), they may form salts with organic or inorganic acids or bases. Examples of suitable acids for such acid addition salt formation are hydrochloric acid, hydrobromic acid, sulfuric acid, phosphoric acid, acetic acid, citric acid, oxalic acid, malonic acid, salicylic acid, p-aminosalicylic acid, malic acid, fumaric acid, succinic acid, ascorbic acid, maleic acid, sulfonic acid, phosphonic acid, perchloric acid, nitric acid, formic acid, propionic acid, gluconic acid, lactic acid, tartaric acid, hydroxymaleic acid, pyruvic acid, phenylacetic acid, benzoic acid, p-aminobenzoic acid, p-hydroxybenzoic acid, methanesulfonic acid, ethanesulfonic acid, nitrous acid, hydroxyethanesulfonic acid, ethylenesulfonic acid, p-toluenesulfonic acid, naphthylsulfonic acid, sulfanilic acid, camphorsulfonic acid, china acid, mandelic acid, o-methylmandelic acid, hydrogen-benzenesulfonic acid, picric acid, adipic acid, d-o-tolyliartanc acid, tartronic acid, (o, m, p)-toluic acid, naphthylamine sulfonic acid, and other mineral or carboxylic acids well known to those skilled in the art. The salts are prepared by contacting the free base form with a sufficient amount of the desired acid to produce a salt in the conventional manner.

Examples for suitable inorganic or organic bases are, for example, NaOH, KOH, NH$_4$OH, tetraalkylammonium hydroxide, lysine or arginine and the like. Salts may be prepared in a conventional manner using methods well known in the art, for example by treatment of a solution of the compound of the general formula (I) with a solution of an acid, selected out of the group mentioned above.

Some of the compounds of the present invention may be crystallised or recrystallised from solvents such as aqueous and organic solvents. In such cases solvates may be formed. This invention includes within its scope stoichiometric solvates including hydrates as well as compounds containing variable amounts of water that may be produced by processes such as lyophilisation.

Certain compounds of the general formula (I) may exist in the form of optical isomers if substituents with at least one asymmetric center are present, e.g. diastereoisomers and mixtures of isomers in all ratios, e.g. racemic mixtures. The invention includes all such forms, in particular the pure isomeric forms. The different isomeric forms may be separated or resolved one from the other by conventional methods, or any given isomer may be obtained by conventional synthetic methods or by stereospecific or asymmetric syntheses. Where a compound according to the general formula (I) contains an alkene moiety, the alkene can be presented as a cis or trans isomer or a mixture thereof. When an isomeric form of a compound of the invention is provided substantially free of other isomers, it will preferably contain less than 5% w/w, more preferably less than 2% w/w and especially less than 1% w/w of the other isomers.

Another aspect of the present invention relates to the use of the inventive bicyclic aza-amides derivatives as drugs, i.e. as pharmaceutically active agents applicable in medicine.

Surprisingly it was found that the above-mentioned bicyclic aza-amides derivatives as well as the pharmaceutical compositions comprising said bicyclic aza-amides derivatives are useful for the specific inhibition of FKBP12, FKBP51 and/or 52.

Therefore one aspect of the present invention is that the compounds according to the general formula (I) are suitable for use as inhibitor of FK506-binding proteins (FKBP). It is preferred if said compound is suitable for use as inhibitor of the FK506-binding protein 51 (FKBP51) or 52 (FKBP52).

It is believed that the compounds of general formulae (I) to (XII) rigidly lock the biologically active conformation of FK506. This effect is contributed to a consistently higher affinity compared to monocyclic scaffolds in the art, in part due to stabilization of the high energy binding conformation. Surprisingly, the binding of the compounds of general formula (VII) for example was preferably enthalpy-driven and entropically disfavored compared to the flexible analogs. Thus, it is believed that conformational control can be a very atom-efficient way for improving affinity that does not require new protein contacts. Also, it is believed that energetically a substantial contribution can be attributed to ligand reorganization and further that ligand rigidification can enhance affinity, selectivity and physicochemical parameters. Further, the compounds of general formula (VII) for example were found as mimics of the putative FKBP transition state. Thus, the inventive compounds represent the first lead-like, functionally active ligands for FKBP51. Also, the compounds of the general formula (VII) for example represent atom-efficient ligands even in very open and thus difficult binding sites such as FKBP51. This result was even more surprising as FKBP51 has emerged as a promising new target for psychiatric disorders but its chemical tractability has proven challenging. So far all known FKBP51 ligands, including the natural products rapamycin and FK506 suffer from a very low ligand efficiency, and further are rather flexible, and therefore display unfavorable pharmacokinetic profiles. Moreover, a high-throughput screening of 350,000 compounds also did not provide any suitable chemical starting points raising doubts on the feasibility of FKBP51 as a CNS drug target.

Thus, the bicyclic aza-amides compounds of the present invention and especially the bicyclic aza-amides compounds according to the general formulae (I) to (VIII) can be used for treatment and prophylaxis, or for the preparation of a pharmaceutical formulation for treatment and prophylaxis of psychiatric and neurodegenerative diseases, disorders and conditions, for neuroprotection or neuroregeneration, for the treatment of neurological disorders, for the treatment of diseases relating to neurodegeneration, for the treatment of cancers, for the treatment of glucocorticoid hyposensitivity syndromes, for the treatment of alopecia and promoting hair growth, for the treatment or prevention of multi-drug resistance, for stimulating neurite growth, for the use as wound healing agents for treating wounds resulting from injury or surgery; for the use in antiglaucomatous medications for treating abnormally elevated intraocular pressure; for the use in limiting or preventing hemorrhage or neovascularization for treating macular degeneration, and for treating oxidative damage to eye tissues, for treating a vision disorder, for improving vision, for treating memory impairment or enhancing memory performance.

Preferably the bicyclic aza-amides compounds according to one of the general formulae (I) to (VIII) are useful for or can be used for treatment and prophylaxis, or for the preparation of a pharmaceutical formulation for treatment and prophylaxis of psychiatric disorder, neurological disorder, cancer, transplant rejection or metabolic disorders, glucocorticoid hyposensitivity syndrome, alopecia, abnormally elevated intraocular pressure, macular degeneration, oxidative damage to eye tissues, vision disorder, memory impairment, and increase and/or support neuroprotection, neuroregeneration, and promote hair growth, and stimulate neurite growth, wound healing, antiglaucomatous medications, and improve vision, and enhance memory performance, and treat or prevent multi-drug resistance, and limit or prevent hemorrhage or neovascularization, and for the treatment of diseases relating to neurodegeneration.

More preferably the bicyclic aza-amides compounds according to one of the general formulae (I) to (VIII) are useful for or can be used for treatment and prophylaxis, or for the preparation of a pharmaceutical formulation for treatment and prophylaxis of psychiatric disorders, cancer, transplant rejection or metabolic disorders, glucocorticoid hyposensitivity syndrome, alopecia, abnormally elevated intraocular pressure, macular degeneration, oxidative damage to eye tissues, vision disorder, memory impairment, and increase and/or support neuroprotection, neuroregeneration, and promote hair growth, and
stimulate neurite growth, wound healing, antiglaucomatous medications, and
improve vision, and
enhance memory performance, and
treat or prevent multi-drug resistance, and
limit or prevent hemorrhage or neovascularization, and
for the treatment of diseases relating to neurodegeneration.

Still more preferably the bicyclic aza-amides compounds according to one of the general formulae (I) to (VIII) are useful for or can be used for treatment and prophylaxis, or for the preparation of a pharmaceutical formulation for treatment and prophylaxis of psychiatric disorders, cancer, transplant rejection or metabolic disorders, glucocorticoid hyposensitivity syndrome, alopecia, abnormally elevated intraocular pressure, macular degeneration, oxidative damage to eye tissues, vision disorder, and
promote hair growth, and
stimulate neurite growth, wound healing, antiglaucomatous medications, and
improve vision, and
enhance memory performance, and
treat or prevent multi-drug resistance, and
limit or prevent hemorrhage or neovascularization, and Most preferred is the use of the bicyclic aza-amides compounds according to one of the general formulae (I) to (VIII) for treatment and prophylaxis, or for the preparation of a pharmaceutical formulation for treatment and prophylaxis of psychiatric disorders, cancer, transplant rejection and metabolic disorders and especially preferred for treatment and prophylaxis, or for the preparation of a pharmaceutical formulation for treatment and prophylaxis of psychiatric disorders such as affective disorders or an anxiety disorders.

Concerning this use, bicyclic aza-amides compounds according to general formula (I) are preferred, wherein $R^4$ represents one of the following two substituents:

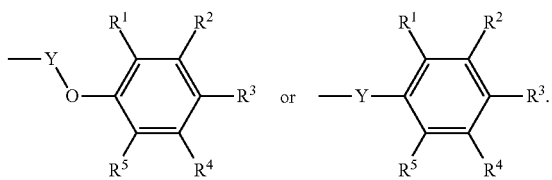

The connection between the inhibition of FKBP51 as result of drug targeting and a treatment or prophylaxis of psychiatric disorders has been disclosed in *Psychoneuroendocrinology*, 2009, 34, 186-95. The connection between the inhibition of FKBP51 and the treatment or prophylaxis of prostate cancer is provided in *Molecular and Cellular Biology*, 2010, 30(5), 1243. The connection between the inhibition or availability of FKBP51 and the treatment or prophylaxis of asthma is disclosed in WO2011/054399.

Examples for the above addressed disorders are depression, nerve regeneration and PTSD for psychiatric disorder and neurological disorder, prostate cancer and malignant melanoma for cancer, peripheral glucocorticoid hyposensitivity for glucocorticoid hyposensitivity syndrome in the field of inflammation.

Particularly for those above examples the bicyclic aza-amides compounds according to one of the general formulae (I) to (VIII) are useful or can be used for treatment and prophylaxis, or for the preparation of a pharmaceutical formulation for treatment and prophylaxis of the afore-mentioned diseases and dysfunctions.

The bicyclic aza-amides compounds of the present invention are preferably suitable for treatment, or for the preparation of a pharmaceutical formulation for prophylaxis and treatment of psychiatric diseases. It is especially preferred if this psychiatric diseases is an affective disorder or an anxiety disorder.

The affective disorder according to the invention is selected from the group comprising or consisting of depression, bipolar disorder, mania, substance induced mood disorder and seasonal affective disorder (SAD). Among the psychiatric diseases and disorders, the most preferred is depression, the most commonly diagnosed psychiatric disorder.

The anxiety disorder according to the invention is selected from the group comprising or consisting of generalized anxiety disorder, panic disorder, panic disorder with agoraphobia, phobias, obsessive compulsive disorder, post-traumatic stress disorder, separation anxiety and childhood anxiety disorders.

Among the hundreds of different neurodegenerative disorders, the attention has been given especially to a handful, including Alzheimer's Disease, Parkinson's Disease, and amyotrophic lateral sclerosis.

Among the glucocorticoid hyposensitivity syndromes, the attention has been given to the group of related diseases enclosing resistant asthma, AIDS, rheumatoid arthritis, hypertension and obesity.

Among the cancers, the attention has been given to malignant melanoma or prostate cancer.

Among the vision disorders, the attention has been given to visual impairments; orbital disorders; disorders of the lacrimal apparatus; disorders of the eyelids; disorders of the conjunctiva; disorders of the Cornea; cataract; disorders of the uveal tract; disorders of the retina; disorders of the optic nerve or visual pathways; free radical induced eye disorders and diseases; immunologically-mediated eye disorders and diseases; eye injuries; and symptoms and complications of eye disease, eye disorder, or eye injury.

Therefore, another aspect of the present invention is directed to pharmaceutical compositions comprising at least one compound of the present invention as active ingredient, together with at least one pharmaceutically acceptable carrier, excipient and/or diluents. The pharmaceutical compositions of the present invention can be prepared in a conventional solid or liquid carrier or diluent and a conventional pharmaceutically-made adjuvant at suitable dosage level in a known way. The preferred preparations are adapted for oral application. These administration forms include, for example, pills, tablets, film tablets, coated tablets, capsules, powders and deposits.

Furthermore, the present invention also includes pharmaceutical preparations for parenteral application, including dermal, intradermal, intragastral, intracutan, intravasal, intravenous, intramuscular, intraperitoneal, intranasal, intravaginal, intrabuccal, percutan, rectal, subcutaneous, sublingual, topical, or transdermal application, which preparations in addition to typical vehicles and/or diluents contain at least one compound according to the present invention and/or a pharmaceutical acceptable salt thereof as active ingredient.

The pharmaceutical compositions according to the present invention containing at least one compound according to the present invention, and/or a pharmaceutical acceptable salt thereof as active ingredient will typically be administered together with suitable carrier materials selected with respect to the intended form of administration, i.e. for oral administration in the form of tablets, capsules (either solid filled, semi-solid filled or liquid filled), powders for constitution, extrudates, deposits, gels, elixirs, dispersable granules, syrups, suspensions, and the like, and consistent with conventional pharmaceutical practices. For example, for oral administration in the form of tablets or capsules, the active drug component may be combined with any oral non-toxic pharmaceutically acceptable carrier, preferably with an inert carrier like lactose, starch, sucrose, cellulose, magnesium stearate, dicalcium phosphate, calcium sulfate, talc, mannitol, ethyl alcohol (liquid filled capsules) and the like. Moreover, suitable binders, lubricants, disintegrating agents and coloring agents may also be incorporated into the tablet or capsule. Powders and tablets may contain about 5 to about 95 weight % of the benzothiophene-1,1-dioxide derived compound and/or the respective pharmaceutically active salt as active ingredient.

Suitable binders include starch, gelatin, natural sugars, corn sweeteners, natural and synthetic gums such as acacia, sodium alginate, carboxymethylcellulose, polyethylene glycol and waxes. Among suitable lubricants there may be mentioned boric acid, sodium benzoate, sodium acetate, sodium chloride, and the like. Suitable disintegrants include starch, methylcellulose, guar gum, and the like. Sweetening and flavoring agents as well as preservatives may also be included, where appropriate. The disintegrants, diluents, lubricants, binders etc. are discussed in more detail below.

Moreover, the pharmaceutical compositions of the present invention may be formulated in sustained release form to provide the rate controlled release of any one or more of the components or active ingredients to optimise the therapeutic effect(s), e.g. antihistaminic activity and the like. Suitable dosage forms for sustained release include tablets having layers of varying disintegration rates or controlled release polymeric matrices impregnated with the active components and shaped in tablet form or capsules containing such impregnated or encapsulated porous polymeric matrices.

Liquid form preparations include solutions, suspensions, and emulsions. As an example, there may be mentioned water or water/propylene glycol solutions for parenteral injections or addition of sweeteners and opacifiers for oral solutions, suspensions, and emulsions. Liquid form preparations may also include solutions for intranasal administration. Aerosol preparations suitable for inhalation may include solutions and solids in powder form, which may be present in combination with a pharmaceutically acceptable carrier such as an inert, compressed gas, e.g. nitrogen. For preparing suppositories, a low melting fat or wax, such as a mixture of fatty acid glycerides like cocoa butter is melted first, and the active ingredient is then dispersed homogeneously therein e.g. by stirring. The molten, homogeneous mixture is then poured into conveniently sized moulds, allowed to cool, and thereby solidified.

Also included are solid form preparations which are intended to be converted, shortly before use, to liquid form preparations for either oral or parenteral administration. Such liquid forms include solutions, suspensions, and emulsions.

The compounds according to the present invention may also be delivered transdermally. The transdermal compositions may have the form of a cream, a lotion, an aerosol and/or an emulsion and may be included in a transdermal patch of the matrix or reservoir type as is known in the art for this purpose.

The term capsule as recited herein refers to a specific container or enclosure made e.g. of methyl cellulose, polyvinyl alcohols, or denatured gelatins or starch for holding or containing compositions comprising the active ingredient(s). Capsules with hard shells are typically made of blended of relatively high gel strength gelatins from bones or pork skin. The capsule itself may contain small amounts of dyes, opaquing agents, plasticisers and/or preservatives. Under tablet a compressed or moulded solid dosage form is understood which comprises the active ingredients with suitable diluents. The tablet may be prepared by compression of mixtures or granulations obtained by wet granulation, dry granulation, or by compaction well known to a person of ordinary skill in the art.

Oral gels refer to the active ingredients dispersed or solubilised in a hydrophilic semi-solid matrix. Powders for constitution refers to powder blends containing the active ingredients and suitable diluents which can be suspended e.g. in water or in juice.

Suitable diluents are substances that usually make up the major portion of the composition or dosage form. Suitable diluents include sugars such as lactose, sucrose, mannitol, and sorbitol, starches derived from wheat, corn rice, and potato, and celluloses such as microcrystalline cellulose. The amount of diluent in the composition can range from about 5 to about 95% by weight of the total composition, preferably from about 25 to about 75 weight %, and more preferably from about 30 to about 60 weight %.

The term disintegrants refers to materials added to the composition to support break apart (disintegrate) and release the pharmaceutically active ingredients of a medicament. Suitable disintegrants include starches, "cold water soluble" modified starches such as sodium carboxymethyl starch, natural and synthetic gums such as locust bean, karaya, guar, tragacanth and agar, cellulose derivatives such as methylcellulose and sodium carboxymethylcellulose, microcrystalline celluloses, and cross-linked microcrystalline celluloses such as sodium croscaramellose, alginates such as alginic acid and sodium alginate, clays such as bentonites, and effervescent mixtures. The amount of disintegrant in the composition may range from about 2 to about 20 weight % of the composition, more preferably from about 5 to about 10 weight %.

Binders are substances which bind or "glue" together powder particles and make them cohesive by forming granules, thus serving as the "adhesive" in the formulation. Binders add cohesive strength already available in the diluent or bulking agent. Suitable binders include sugars such as sucrose, starches derived from wheat corn rice and potato, natural gums such as acacia, gelatin and tragacanth, derivatives of seaweed such as alginic acid, sodium alginate and ammonium calcium alginate, cellulose materials such as methylcellulose, sodium carboxymethylcellulose and hydroxypropylmethylcellulose, polyvinylpyrrolidone, and inorganic compounds such as magnesium aluminum silicate. The amount of binder in the composition may range from about 2 to about 20 weight % of the composition, preferably from about 3 to about 10 weight %, and more preferably from about 3 to about 6 weight %.

Lubricants refer to a class of substances which are added to the dosage form to enable the tablet granules etc. after being compressed to release from the mould or die by reducing friction or wear. Suitable lubricants include metallic stearates such as magnesium stearate, calcium stearate, or potassium stearate, stearic acid, high melting point waxes, and other water soluble lubricants such as sodium chloride, sodium benzoate, sodium acetate, sodium oleate, polyethylene glycols and D,L-leucine. Lubricants are usually added at the very last step before compression, since they must be present at the surface of the granules. The amount of lubricant in the composition may range from about 0.2 to about 5 weight % of the composition, preferably from about 0.5 to about 2 weight %, and more preferably from about 0.3 to about 1.5 weight % of the composition.

Glidents are materials that prevent caking of the components of the pharmaceutical composition and improve the flow characteristics of granulate so that flow is smooth and uniform. Suitable glidents include silicon dioxide and talc. The amount of glident in the composition may range from about 0.1 to about 5 weight % of the final composition, preferably from about 0.5 to about 2 weight %.

Coloring agents are excipients that provide coloration to the composition or the dosage form. Such excipients can include food grade dyes adsorbed onto a suitable adsorbent such as clay or aluminum oxide. The amount of the coloring agent may vary from about 0.1 to about 5 weight % of the composition, preferably from about 0.1 to about 1 weight %.

Said pharmaceutical compositions may further comprise at least one active bicyclic aza-amides compound of the general formula (I).

The pharmaceutical compositions may further comprise at least one further active agent. It is preferred if this active agent is selected from the group consisting of anti-depressant and other psychotropic drugs. It is further preferred if the anti-depressant is selected from amitriptyline, amioxide clomipramine, doxepine, duloxetine, imipramine trimipramine, mirtazapine, reboxetine, citaloprame, fluoxetine, moclobemide and sertraline.

EXAMPLES

Generic Route to Bicyclic Aza-Amides

Example 1

Preparation of Precursors A

Synthesis of Precursor A

Synthesis of 6-(Cyanomethyl) picolinic acid

Butyl lithium (6.02 g, 94 mmol) (47 ml 2 mol/L butyl lithium in cyclohexane) was added into 100 ml anhydrous THF at −78° C. followed by addition of acetonitrile (4.06 g, 99 mmol) under argon. The mixture was stirring at −78° C. for 30 min. Then 6-bromopicolinic acid (2.5 g, 12.38 mmol) in 100 ml anhydrous THF cooled on ice was added dropwise. The mixture was stirring for another 2 h at −78° C. and 30 min at room temperature. Reaction mixture was concentrated in vacuo, dissolved in DCM and extracted with saturated NaHCO$_3$ solution for three times. The collected aqueous layers were acidified with 10% HCl, and then extracted with DCM for six times. The collected organic layers were dried over MgSO$_4$ and concentrated in vacuo. This crude product was used for next reaction without further purification.

TLC [20% MeOH, 0.2% TFA in CHCl$_3$]: R$_f$=0.04

Yield: 1.76 g (87.7%)

$^1$HNMR (300 MHz, CDCl$_3$): δ=8.1 (d, 1H, J=7.75 Hz), 8.05 (t, 1H, J=7.77, 7.77 Hz), 7.75 (d, 1H, J=7.8 Hz), 4.08 (s, 2H)

$^{13}$C NMR (75 MHz, CDCl$_3$): δ=163.69, 150.06, 146.67, 140.26, 126.86, 123.68, 116.05, 26.47

HRMS: 163.0504 [M+H]$^+$, 185.0321 [M+Na]$^+$, calculated 163.0508 [M+H]$^+$

Synthesis of Methyl 6-(cyanomethyl) picolinate 6-(Cyanomethyl) picolinic acid (1.31 g, 8.08 mmol) was dissolved in 27 ml anhydrous MeOH at room temperature. 13.35 ml 2M TMSCHN$_2$ in Et$_2$O (3.05 g, 26.7 mmol) was added dropwise at 0° C. followed by stirring at room temperature for 5 h. Reaction was quenched by adding saturated NaHCO$_3$ solution, extracted with DCM for six times, dried

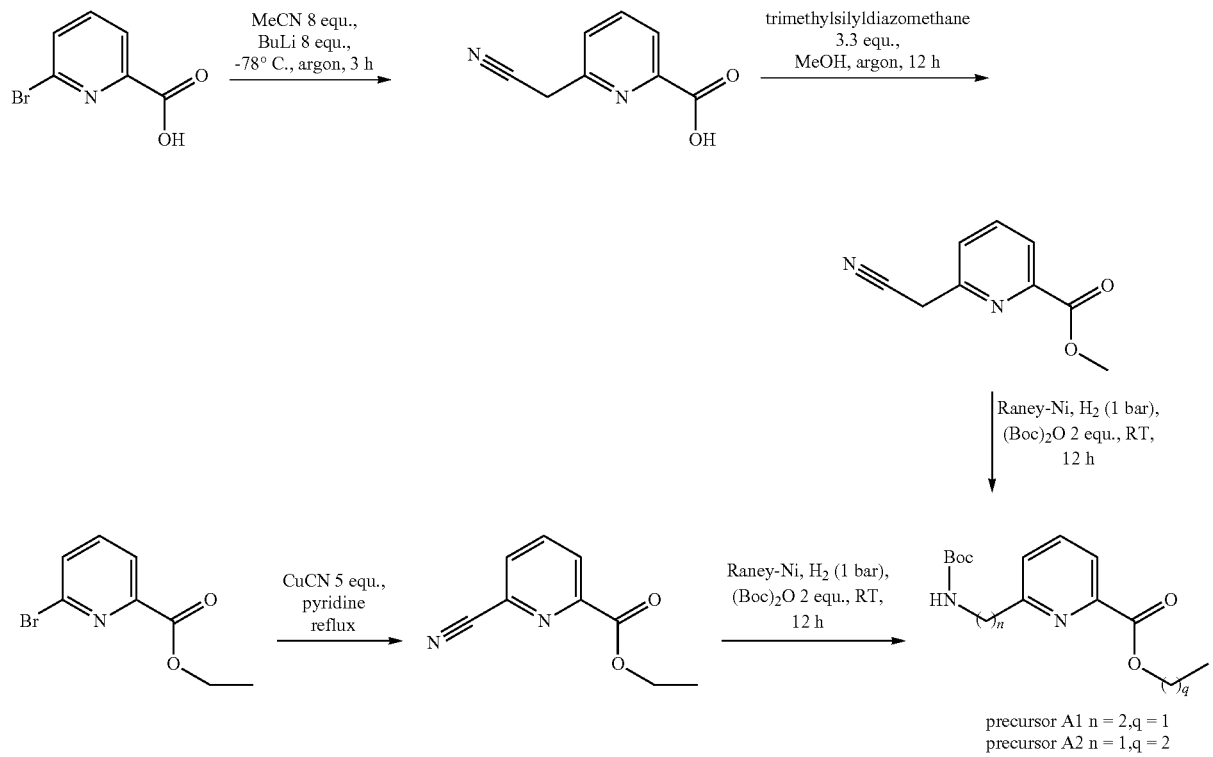

precursor A1 n = 2, q = 1
precursor A2 n = 1, q = 2 over MgSO$_4$, concentrated in vacuo followed by purification with flash chromatography in hexane/EE 1:1.

TLC [hexane/EE 1:1]: R$_f$=0.54

Yield: 750 mg (52.7%)

$^1$HNMR (300 MHz, CDCl$_3$): δ=8.12 (d, 1H, J=7.79 Hz), 7.88-7.98 (m, 1H), 7.72 (d, 1H, d=7.82 Hz), 4.08 (s, 2H), 4.02 (s, 3H)

HRMS: 177.0649 [M+H]$^+$, 199.0472 [M+Na]$^+$, calculated 177.0664[M+H]$^+$

Synthesis of ethyl 6-cyanopicolinate

CuCN (31.1 g, 348 mmol) was added into ethyl 6-bromopicolinate (16 g, 69.5 mmol) in 608 ml pyridine. The mixture was refluxed under argon for 16 h, filtered through celite, and concentrated in vacuo. Saturated NaHCO$_3$ solution was added followed by extracted with DCM for three times. The mixture was purified with flash chromatography in hexane/EE=1:1.

TLC [hexane/EE 1:1]: R$_f$=0.65

Yield: 7.3 g, (60%)

$^1$HNMR (600 MHz, CDCl$_3$): δ=8.32 (dd, 1H, J=1.15, 7.97 Hz), 8.04 (t, 1H, J=7.86, 7.86 Hz), 7.88 (dd, 1H, J=1.13, 7.76 Hz), 4.52 (q, 2H, J=7.13, 7.13, 7.12 Hz), 1.40 (t, 3H, J=7.13, 7.13 Hz)

$^{13}$C NMR (300 MHz, CDCl$_3$): δ=163.76, 150.06, 138.70, 134.23, 131.40, 128.12, 116.62, 62.89, 14.44

HRMS: 177.0669[M+H], calculated 177.0664[M+H]

Synthesis of ethyl-6-((tert-butoxycarbonylamino)methyl) picolinate (precursor A C1)

Ethyl 6-cyanopicolinate (7.87 g, 44.7 mmol) was dissolved in MeOH under argon and degassed followed by addition of Boc$_2$O (19.5 g, 89 mmol), catalytical amount Ni-catalyst and by degasing with argon again. The reaction was stirred under 1 atm H$_2$ at room temperature for 24 h, filtered through celite, and concentrated in vacuo. The mixture was purified with flash chromatography in EE/DCM=1:5.

TLC [EE/DCM 1:5]: R$_f$=0.34

Yield: 8.74 g, (68%)

Synthesis of Methyl-6-(2-(tert-butoxycarbonylamino)ethyl) picolinate (precursor A C2)

Methyl 6-(cyanomethyl) picolinate (5) (0.75 g, 4.26 mmol) was dissolved in 54 ml MeOH and degassed with argon. Then Boc$_2$O (1.858 g, 8.51 mmol) and Raney-Ni catalyst was added and degassed with argon again. The reaction was stirred under 1 atm H$_2$ at room temperature for 24 h, filtered through celite, and concentrated in vacuo. The mixture was purified with flash chromatography in EE/DCM=1:2.

TLC [EE/DCM 1:2]: R$_f$=0.54

Yield—860 mg, (76%)

$^1$HNMR (300 MHz, CDCl$_3$) δ=7.95-8.05 (m, 1H), 7.75-7.85 (m, 1H), 7.35-7.45 (m, 1H), 4.00 (s, 3H), 3.58-3.65 (m, 2H), 3.05-3.15 (m, 2H), 1.44 (s, 9H)

HRMS: m/z: found 281.1457 [M+H]$^+$, 303.1287 [M+Na]$^+$, calculated 281.1501 [M+H]$^+$

Example 2

Preparation of Precursors B

Synthesis of Precursor B:

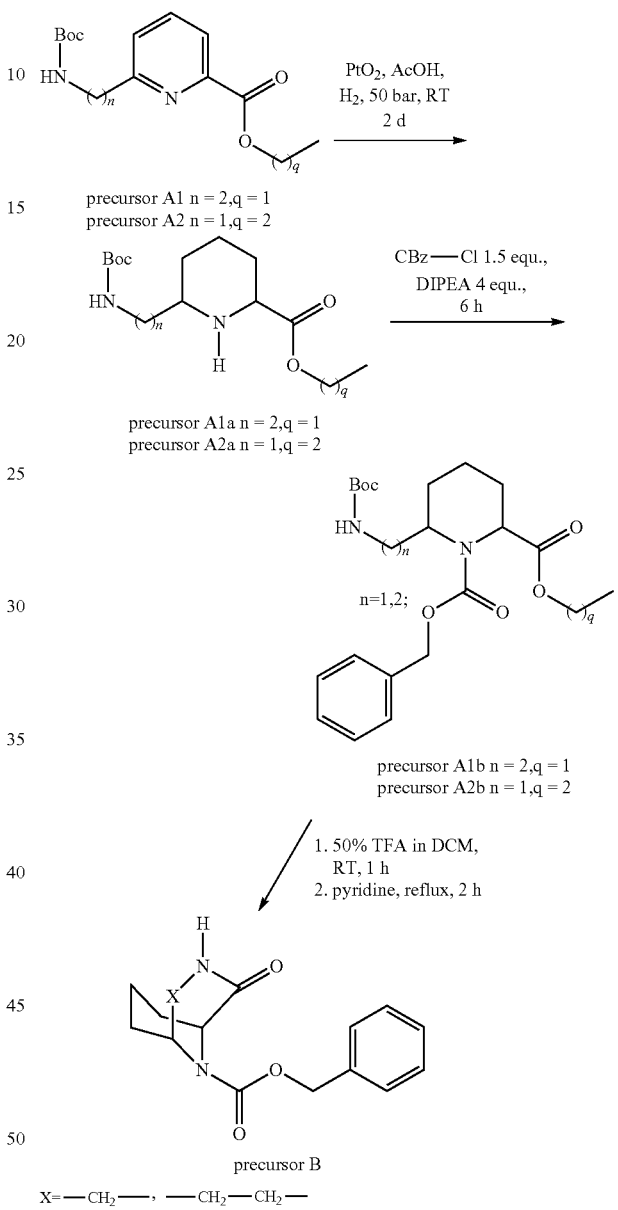

precursor B

X= —CH$_2$—, —CH$_2$—CH$_2$—

Synthesis of ethyl 6-((tert-butoxycarbonylamino) methyl)piperidine-2-carboxylate Ethyl 6-((tert-butoxycarbonylamino)methyl)picolinate (8.74 g, 31.2 mmol) was dissolved in AcOH and degassed with argon in a reactor (Roth), then catalytical amount PtO$_2$ was added and degassed with argon again. The reaction was stirred at room temperature under H$_2$ (40 bar) for 3 days. 8a was not fully converted. The reaction mixture was filtered through celite, concentrated in vacuo and purified with flash chromatography in EE. The retrieval of 8a was repeated until 100% converted with the same procedure.

TLC [EE]: $R_f$=0.38

Yield—4.35 g, (49%)

$^1$HNMR (600 MHz, CDCl$_3$) δ=5.07 (s, 1H), 4.14-4.2 (m, 2H), 3.33 (dd, 1H, J=2.83, 11.52 Hz), 3.23-3.35 (m, 1H), 2.90-3.05 (m, 1H), 2.66-2.70 (m, 1H), 1.97-2.05 (m, 3H), 1.86-1.92 (m, 1H), 1.59-1.65 (m, 1H), 1.4-1.48 (m, 10H), 1.32-1.4 (m, 1H), 1.03-1.12 (m, 1H).

$^{13}$C NMR (300 MHz, CDCl$_3$) δ=175.00, 156.25, 79.3, (60.92, 60.97), (58.7, 58.75), 55.68, 46, (29.06, 29.1), (28.96, 29.01), (28.37, 28.41), 23.92, (14.13, 14.17)

MS (ESI) m/z: found 287.2 [M+H]$^+$, calculated 287.1791 [M+H]$^+$

Synthesis of Methyl 6-(2-(tert-butoxycarbonylamino)ethyl) piperidine-2-carboxylate Methyl 6-(2-(tert-butoxycarbonylamino)ethyl) picolinate (8b) (644.46 mg, 2.299 mmol) was dissolved in 33 ml AcOH and degassed with argon in a reactor (Roth), then catalytical amount PtO$_2$ was added and degassed with argon again. The reaction was stirred at room temperature under H$_2$ (50 bar) for 2 days, filtered through celite, and concentrated in vacuo followed by purification with flash chromatography in EE.

TLC [EE]: $R_f$=0.31

Yield—646.29 mg, (98%)

$^1$HNMR (600 MHz, CDCl$_3$) δ=3.74 (s, 3H), 3.32-3.42 (m, 1H), 3.12-3.32 (m, 2H), 2.55-2.67 (m, 1H), 1.95-2.05 (m, 1H), 1.85-1.95 (m, 1H), 1.55-1.7 (m, 3H), 1.4-1.5 (m, 9H), 1.25-1.4 (m, 2H), 1-1.15 (m, 1H)

HRMS: m/z: found 287.1876 [M+H]$^+$, calculated 287.1971[M+H]

Synthesis of 1-benzyl 2-ethyl 6-((tert-butoxycarbonylamino)methyl)piperidine-1,2-dicarboxylate Benzyl chloroformate (3.89 g, 22.78 mmol) was added into Ethyl 6-((tert-butoxycarbonylamino)methyl)piperidine-2-carboxylate (4.35 g, 15.19 mmol) in 50 ml DCM at 0° C. dropwise followed by addition of N,N-diisopropylethylamine (7.85 g, 60.8 mmol). The reaction was stirred at room temperature for 5 h. Then saturated NH$_4$Cl solution was added followed by extraction with DCM for four times. The pure product was obtained after purification with flash chromatography in Hexane/EE 3:1

TLC [Hexane/EE 3:1]: $R_f$=0.26

Yield—6.14 g, (96%)

$^1$HNMR (300 MHz, CDCl$_3$) δ=7.25-7.4 (m, 5H), 5.2-5.4 (m, 1H), 5.0-5.1 (m, 1H), 4.7-5-0 (m, 1H), 4.36-4.52 (m, 1H), 4.06-4.3 (m, 1H), 3.3-3.5 (m, 1H), 2.9-3.14 (m, 1H), 2.18-2.35 (m, 1H), 1.5-1.8 (m, 6H), 1.3-1.5 (m, 10H), 1.1-1.3 (m, 3H)

$^{13}$C NMR (300 MHz, CDCl$_3$) δ=173.4, 157.1, 156.4, 136.79, 128.68, 128.17, 127.96, 79.14, 67.8, 61.80, 53.4, 50.54, 42.58, 28.69, 26.26, 16.53, 14.33

MS (ESI) m/z: found 421.22[M+H]$^+$, calculated 421.23 [M+H]$^+$

HRMS: m/z: found 421.2333 [M+H]$^+$, calculated 421.2339 [M+H]$^+$

Synthesis of 1-Benzyl 2-methyl 6-(2-(tert-butoxycarbonylamino)ethyl) piperidine-1,2-dicarboxylate Benzyl Chloroformate (578 mg, 3.39 mmol) was added into methyl 6-(2-(tert-butoxycarbonylamino)ethyl)piperidine-2-carboxylate (646.29 mg, 2.257 mmol) in 7 ml DCM at 0° C. followed by dropwise addition of N,N-diisopropylethylamine (1167 mg, 9.03 mmol). The reaction was stirring at room temperature for 6 hours and quenched with saturated NH$_4$Cl solution and followed by extraction with DCM for four times. The pure product was obtained after purification with flash chromatography in Hexane/EE 2:1

TLC [Hexane/EE 2:1]: $R_f$=0.46

Yield—811.55 mg, (86%)

Synthesis of Benzyl 2-oxo-3,9-diazabicyclo[3.3.1]nonane-9-carboxylate (precursor B C1)

Step 1:1-benzyl 2-ethyl 6-((tert-butoxycarbonylamino)methyl)piperidine-1,2-dicarboxylate (6.11 g, 15.03 mmol) in 50% TFA in DCM was stirred at room temperature for 1 h, then concentrated in vacuo. DCM was added and evaporated for three times to remove the TFA. It was used for the next step without further purification.

Step 2: the compound from step 1 was dissolved in pyridine and refluxed for 2 h. The mixture was concentrated in vacuo and purified with flash chromatography in EE.

TLC [EE]: Rf=0.23

Yield—3.14 g, (76%)

$^1$HNMR (600 MHz, CDCl$_3$) δ=7.28-7.42 (m, 5H), 5.05-5.2 (m, 2H), 4.63-4.77 (m, 1H), 4.43-4.57 (m, 1H), 3.63-3.77 (m, 1H), 3.15-3.24 (m, 1H), 1.89-1.99 (m, 1H), 1.66-1.89 (m, 5H)

$^{13}$C NMR (150 MHz, CDCl$_3$) δ=171.41, 154.19, 136.31, 128.77, 128.42, 128.15, 67.79, (54.18, 53.47), (45.94, 45.59), (44.98, 44.13), (30.59, 30.20), (27.84, 27.43), 18.12

HRMS: m/z: found 275.1390 [M+H]$^+$, calculated 275.1396 [M+H]$^+$

Synthesis of Benzyl 2-oxo-3,10-diazabicyclo[4.3.1] decane-10-carboxylate (precursor B C2)

Step 1:1-benzyl 2-methyl 6-(2-(tert-butoxycarbonylamino)ethyl)piperidine-1,2-dicarboxylate (10b) (92.14 mg, 0.219 mmol) in 3 ml 50% TFA in DCM was stirred at room temperature for 1 hour and then concentrated in vacuo. DCM was added and evaporated for three times to remove the TFA. It was used for the next step without further purification.

TLC [10% MeOH in CHCl$_3$]: $R_f$=0.31

Step 2: the crude product from step 1 was dissolved in 3 ml pyridine and refluxed for 2 days. The reaction mixture was concentrated in vacuo followed by purification with flash chromatography in EE.

TLC [EE]: $R_f$=0.26

Yield—20.77 mg, (33%)

$^1$H-NMR (300 MHz, CDCl$_3$): δ==7.28-7.38 (m, 5H), 6.52-6.74 (m, 1H), 5.12-5.24 (m, 2H), 4.96-5.18 (m, 1H), 4.6-4.74 (m, 1H), 3.14-3.22 (m, 1H), 2.88-2.96 (m, 1H), 2.24-2.36 (m, 1H), 2.12-2.24 (m, 1H), 1.88-1.96 (m, 1H), 1.56-1.76 (m, 4H), 1.48-1.56 (m, 1H).

$^{13}$C-NMR (150 MHz, CDCl$_3$): δ==175.24, (156.0, 155.92), (136.37, 136.30), (128.58, 128.52), 128.23, 128.12, 127.00, 127.80, 67.63, (55.51, 55.28), (46.89, 46.44), (39.28, 39.26), (33.02, 32.88), (29.24, 28.91), (28.10, 27.92), (15.32, 15.26)

MS (ESI) m/z: found 289.15 [M+H]$^+$, calculated 289.12

HRMS: m/z: found 289.1546 [M+H]⁺, calculated 289.1552 [M+H]

Example 3

Compounds 4 with X=—CH₂—

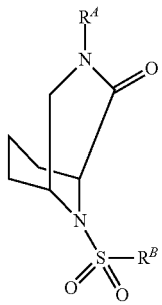

Route to structures according to the general formula (I)

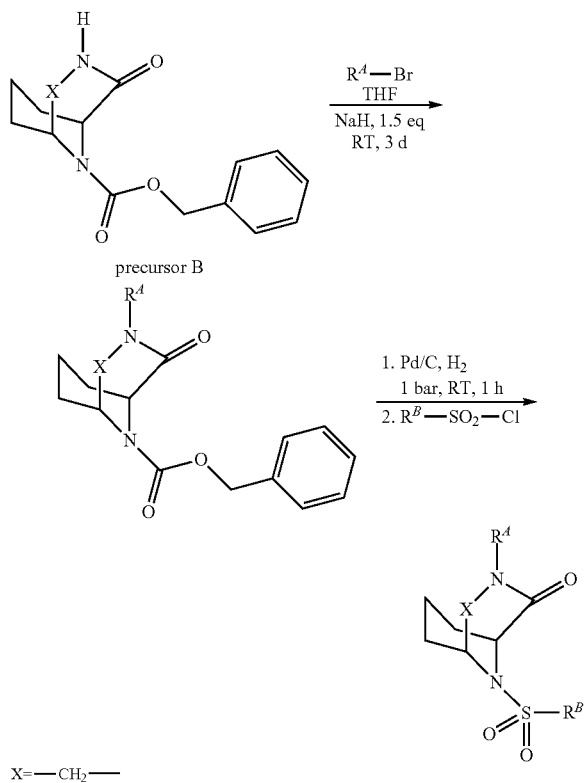

X=—CH₂—

Synthesis of benzyl 3-(2-(3,4-dimethoxyphenoxyl)ethyl)-2-oxo-3,9-diazabicyclo[3.3.1]nonane-9-carboxylate NaH (26.2 mg, 0.911 mmol) was added to benzyl 2-oxo-3,9-diazabicyclo[3.3.1]nonane-9-carboxylate (100 mg, 0.35 mmol) in 2 ml dry THF under argon at 0° C. After stirring for 15 min, 4-(2-bromoethoxy)-1,2-dimethoxybenzene (238 mg, 0.911 mmol) was added and stirred at room temperature for 5 days. The reaction mixture was first concentrated in vacuo, and then dissolved in 10% HCl solution followed by extraction with DCM for three times. The organic layers were dried over MgSO₄ and concentrated. The pure product was obtained after purification with flash chromatography in HE/EE 2:1

TLC [Hexane/EE 1:2]: $R_f$=0.31
Yield—104 mg, (63%)
¹HNMR (300 MHz, CDCl₃) δ=7.3-7.42 (m, 5H), 6.74-6.8 (m, 1H), 4.45-4.50 (m, 1H), 4.34-4.42 (m, 1H), 5.07-5.2 (m, 2H), 4.42-4.82 (m, 2H), 4.05-4.25 (m, 2H), 3.9-4.05 (m, 1H), 3.77-3.9 (m, 7H), 3.38-3.62 (m, 2H), 1.92-2.04 (m, 1H), 1.78-1.92 (m, 1H), 1.6-1.78 (m, 4H)
¹³C NMR (75 MHz, CDCl₃) δ=168.6, 154.2, 153.21, 150.14, 144.01, 136.3, 128.77, 128.41, 128.18, 112.21, 104.20, 100.73, 67.71, 66.95, 56.68, 56.11, 54.5, 53.10, 46.79, 45.4, 30.4, 28.2, 18.50
HRMS: m/z: found 455.2176[M+H]⁺, calculated 455.2182 [M+H]⁺

Synthesis of 3-(2-(3,4-dimethoxyphenoxyl)ethyl)-3,9-diazabicyclo[3.3.1]nonan-2-one To a solution of benzyl 3-(3,4-dimethoxyphenoxy)ethyl)-2-oxo-3,9-diazabicyclo[3.3.1]nonane-9-carboxylate (104 mg, 0.2 mmol) in 1 ml anhydrous MeOH was added catalytic amounts of Palladium on carbon and degassed with H₂. The reaction was stirred at room temperature under 1 atm H₂ for 2 h, filtered through celite, concentrated in vacuo and used for the next step without further purification.

TLC [MeOH: CHCl₃ 1:9]: $R_f$=0.4
Yield: 73 mg, 0.2 mmol (100%)
¹HNMR (600 MHz, CDCl₃) δ=6.80 (d, 1H, J=8.75 Hz), 6.51 (s, 1H), 6.39-6.44 (m, 1H), 4.15-4.25 (m, 2H), 3.9-4 (m, 1H), 3.8-3.89 (m, 7H), 3.54-3.64 (m, 2H), 3.45-3.51 (m, 1H), 3.35-3.43 (m, 1H), 2.39 (s, 1H), 1.55-2 (m, 6H)
¹³C NMR (300 MHz, CDCl₃) δ=171.35, 153.08, 149.89, 143.71, 111.95, 104.02, 100.53, 66.81, 56.45, 55.9, 54.4, 54.3, 46.6, 45.9, 31.8, 28.9, 18.22
HRMS: m/z: found 321.1808 [M+H]⁺, calculated 321.1814 [M+H]⁺

Synthesis of 2-oxo-2-(3,4,5-trimethoxyphenyl)acetic acid 1-(3,4,5-Trimethoxyphenyl)ethanone (2.93 g, 13.9 mmol) and selenium dioxide (2.32 g, 20.9 mmol) in 60 ml pyridine were heated to 100° C. for 14 h. The mixture was filtered through celite, concentrated in vacuo and purified with flash chromatography in hexane:EtOAc:AcOH 1:15:1.

TLC (hexane:EtOAc:AcOH 1:15:1): $R_f$=0.14
Yield: 2.19 g, 9.1 mmol (65%)
¹HNMR (600 MHz, CDCl₃) δ=3.91 (s, 6H), 3.95 (s, 3H), 7.50 (s, 2H)
¹³C NMR (150 MHz, CDCl₃) δ=56.31, 61.03, 108.04, 127.55, 144.19, 153.06, 165.74, 186.94
HRMS (EI): m/z: found 240.0624[M]⁺, calculated 240.0634[M]⁺

Synthesis of 9-(3,5-dichlorophenylsulfonyl)-3-(2-(3,4-dimethoxyphenoxyl)ethyl)-3,9-diazabicyclo[3.3.1]nonan-2-one 4b 3-(2-(3,4-Dimethoxyphenoxyl)ethyl)-3,9-diazabicyclo[3.3.1]nonan-2-one (24 mg, 0.08 mmol) in 3 ml DCM was treated with DIPEA (12 mg, 0.09 mmol) and stirred for 30 min at room temperature followed by addition of 3,5-dichlorobenzene sulfonyl chloride (22 mg, 0.09 mmol). After stirring for 6 h at room temperature, the reaction was quenched with saturated NH$_4$Cl solution (5 ml), extracted with DCM (4×10 ml). The organic layers were dried over MgSO$_4$ and concentrated in vacuo. The mixture was purified with flash chromatography in hexane: EtOAc 1:1.

TLC [EtOAc]: R$_f$=0.48
Yield: 21 mg, 0.04 mmol (53%) purity >99%
$^1$HNMR (600 MHz, CDCl$_3$) δ=7.66-7.73 (m, 2H), 7.33-7.39 (m, 1H), 6.74-6.79 (m, 1H), 6.36-6.41 (m, 1H), 6.28-6.33 (m, 1H), 4.43 (s, 1H), 4.28-4.33 (m, 1H), 4.04-4.10 (m, 1H), 3.88-3.94 (m, 1H), 3.73 (d, 6H, J=6.56 Hz), 3.65-3.72 (m, 1.5H), 3.55-3.62 (m, 1H), 3.3-3.37 (m, 1.5H), 1.88-2.02 (m, 2H), 1.72-1.84 (m, 2H), 1.54-1.72 (m, 2H)
$^{13}$C NMR (300 MHz, CDCl$_3$) δ=166.85, 152.74, 149.83, 143.85, 142.76, 136.14, 132.87, 125.29, 111.92, 103.94, 100.36, 66.89, 56.45, 55.85, 55.12, 52.12, 47.40, 46.57, 31.46, 28.13, 17.27
HRMS (EI): m/z: found 528.0893 [M]$^+$, calculated 528.0889[M]$^+$ Synthesis of 9-(benzo[d]thiazol-6-ylsulfonyl)-3-(2-(3,4-dimethoxyphenoxy)-ethyl)-3,9-diazabicyclo[3.3.1]nonan-2-one 4c 3-(2-(3,4-Dimethoxyphenoxyl)ethyl)-3,9-diazabicyclo[3.3.1]nonan-2-one (32 mg, 0.1 mmol) in 3 ml DCM was treated with DIPEA (15 mg, 0.12 mmol) and stirring for 30 min at room temperature followed by addition of 1,3-benzothiazole-6-sulfonyl chloride (28 mg, 0.12 mmol). The reaction was stirred overnight at room temperature, the reaction was quenched with saturated NH$_4$Cl solution (5 ml), extracted with DCM (4×10 ml). The organic layers were dried over MgSO$_4$ and concentrated in vacuo. The mixture was purified with Preparative-TLC in 10% MeOH in CHCl$_3$.

TLC [EE]: R$_f$=0.47
Yield: 8 mg, 0.02 mmol (15%) purity >99%
$^1$HNMR (600 MHz, CDCl$_3$) δ=9.13 (s, 1H), 8.51 (d, 1H, J=1.33 Hz), 8.18 (d, 1H, J=8.62 Hz), 7.93 (dd, 1H, J=1.87, 8.63 Hz), 6.72 (d, 1H, J=8.79 Hz), 6.31 (d, 1H, J=2.82 Hz), 6.18-6.23 (m, 1H), 4.43-4.46 (m, 1H), 4.35-4.39 (m, 1H), 3.92-3.98 (m, 1H), 3.78-3.83 (m, 6H), 3.7-3.74 (m, 1H), 3.5-3.59 (m, 2H), 3.29-3.33 (m, 1H), 2.97-3.05 (m, 1H), 1.96-2.01 (m, 1H), 1.9-1.96 (m, 1H), 1.76-1.84 (m, 1H), 1.7-1.75 (m, 1H), 1.6-1.68 (m, 2H)
$^{13}$C NMR (300 MHz, CDCl$_3$) δ=167.25, 158.13, 155.6, 152.66, 149.80, 143.76, 136.86, 134.3, 124.55, 124.38, 122.18, 111.83, 103.86, 100.29, 66.60, 56.39, 55.84, 55.03, 51.90, 47.21, 46.23, 31.53, 28.04, 17.30
HRMS (EI): m/z: found 517.1340 [M]$^+$, calculated 517.1341 [M]$^+$ Synthesis of 6-(3-(2-(3,4-dimethoxyphenoxyl)ethyl)-2-oxo-3,9-diazabicyclo-[3.3.1]nonan-9-ylsulfonyl)benzo[d]thiazol-2(3H)-one 4d 3-(2-(3,4-Dimethoxyphenoxyl)ethyl)-3,9-diazabicyclo[3.3.1]nonan-2-one (40 mg, 0.13 mmol) in 3 ml DCM was treated with DIPEA (32 mg, 0.25 mmol) and stirred for 30 min at room temperature followed by addition of 2-oxo-2,3-dihydrobenzo[d]thiazole-6-sulfonyl chloride (62 mg, 0.25 mmol). After stirring overnight at room temperature, the reaction was quenched with saturated NH$_4$Cl solution (5 ml), extracted with DCM (4×10 ml). The organic layers were dried over MgSO$_4$ and concentrated in vacuo. The mixture was purified with Preparative-HPLC in 50-57% buffer B in 16 mins.

TLC [EE]: R$_f$=0.38
Yield: 35 mg, 0.07 mmol (53%) purity >99%
$^1$HN.MR (300 MHz, DMSO) δ=12.33-12.40 (m, 1H), 8.11-8.15 (m, 1H), 7.64-7.71 (m, 1H), 7.20-7.26 (m, 1H), 6.75-6.85 (m, 1H), 6.44-6.48 (m, 1H), 6.23-6.32 (m, 1H), 4.19-4.28 (m, 1H), 4.12-4.18 (m, 1H), 3.71-3.83 (m, 2H), 3.69 (s, 3H), 3.66 (s, 3H), 3.36-3.50 (m, 2H), 3.20-3.29 (m, 1H), 2.97-3.10 (m, 1H), 1.35-1.82 (m, 6H)
$^{13}$C NMR (75 MHz, DMSO) δ=170.69, 166.56, 152.95, 150.12, 143.74, 140.65, 133.40, 126.15, 124.90, 122.45, 113.20, 112.11, 104.48, 101.25, 65.55, 56.51, 55.92, 54.85, 50.70, 47.20, 45.41, 31.27, 28.09, 17.25
HRMS (EI) m/z: found 533.1299 [M]$^+$, calculated 533.1290 [M]$^+$ Synthesis of 3,9-diazabicyclo[3.3.1]nonan-2-one 31

To a solution of benzyl 2-oxo-3,9-diazabicyclo[3.3.1]nonane-9-carboxylate (precursor B, 84 mg, 0.3 mmol) in 1 ml anhydrous MeOH was added catalytic amounts of Palladium on carbon and degassed with H$_2$. After stirring under 1 atm H$_2$ at room temperature for 2 h, the reaction mixture was filtered through celite, concentrated in vacuo and used for the next step without further purification.

TLC [20% MeOH in CHCl$_3$]: R$_f$=0.17
Yield: 35 mg, 0.25 mmol (82%)

Synthesis of 6-(2-oxo-3,9-diazabicyclo[3.3.1]nonan-9-ylsulfonyl)benzo[d]-thiazol-2(3H)-one 4e 3,9-Diazabicyclo[3.3.1]nonan-2-one (25 mg, 0.2 mmol) in 1 ml DCM under argon was treated with DIPEA (69 mg, 0.5 mmol) and stirred for 30 min at room temperature followed by addition of 2-oxo-2,3-dihydrobenzo[d]thiazole-6-sulfonyl chloride (53 mg, 0.2 mmol). After stirring overnight at room temperature, the reaction was quenched with saturated NH$_4$Cl solution (5 ml), extracted with DCM (4×10 ml). The organic layers were dried over MgSO$_4$ and concentrated in vacuo. The mixture was purified with Preparative-HPLC in 45% buffer B in 16 mins.

TLC [10% MeOH in DCM]: R$_f$=0.71
Yield: 27 mg, 0.08 mmol (43%) purity >99%
$^1$HNMR (600 MHz, DMSO-D$_6$) δ=8.13 (d, 1H, J=1.88 Hz), 7.68 (dd, 1H, J=1.98, 8.44 Hz), 7.60 (s, 1H), 7.21 (d, 1H, J=8.39 Hz), 4.12-4.15 (m, 1H), 4.01-4.04 (m, 1H), 3.17-3.25 (m, 1H), 2.93-2.97 (m, 1H), 1.57-1.73 (m, 5H), 1.40-1.50 (m, 1H)
$^{13}$C NMR (300 MHz, DMSO) δ=170.80, 167.59, 140.59, 133.66, 126.07, 124.82, 122.52, 112.14, 54.62, 46.17, 44.07, 31.11, 27.63, 17.59
HRMS (EI+): m/z: found 353.0458 [M]$^+$, calculated 353.0504 [M]$^+$ Synthesis of 3-(2-(3,4-dimethoxyphenethyl)-3,9-diazabicyclo[3.3.1]nonan-2-one To a solution of benzyl 3-(3,4-dimethoxyphenethyl)-2-oxo-3,9-diazabicyclo[3.3.1]nonane-9-carboxylate (104 mg, 0.2 mmol) in 1 ml anhydrous MeOH was added catalytic amounts of Palladium on carbon and degassed with H$_2$. The reaction was stirred at room temperature under 1 atm H$_2$ for 2 h, filtered through celite, concentrated in vacuo and used for the next step without further purification.

TLC [MeOH: CHCl$_3$ 1:9]: R$_f$=0.4
Yield: 73 mg, 0.2 mmol (100%)
$^1$HNMR (600 MHz, CDCl$_3$) δ=6.80 (d, 1H, J=8.75 Hz), 6.51 (s, 1H), 6.39-6.44 (m, 1H), 4.15-4.25 (m, 2H), 3.9-4 (m, 1H), 3.8-3.89 (m, 7H), 3.54-3.64 (m, 2H), 3.45-3.51 (m, 1H), 3.35-3.43 (m, 1H), 2.39 (s, 1H), 1.55-2 (m, 6H)
$^{13}$C NMR (300 MHz, CDCl$_3$) δ=171.35, 153.08, 149.89, 143.71, 111.95, 104.02, 100.53, 66.81, 56.45, 55.9, 54.4, 54.3, 46.6, 45.9, 31.8, 28.9, 18.22
HRMS: m/z: found 321.1808 [M+H]$^+$, calculated 321.1814 [M+H]

Example 4

Compounds 5 with X=—CH$_2$—CH$_2$—

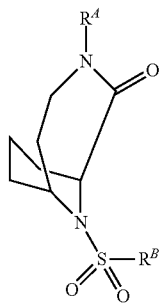

Route to structures according to the general formula (I):

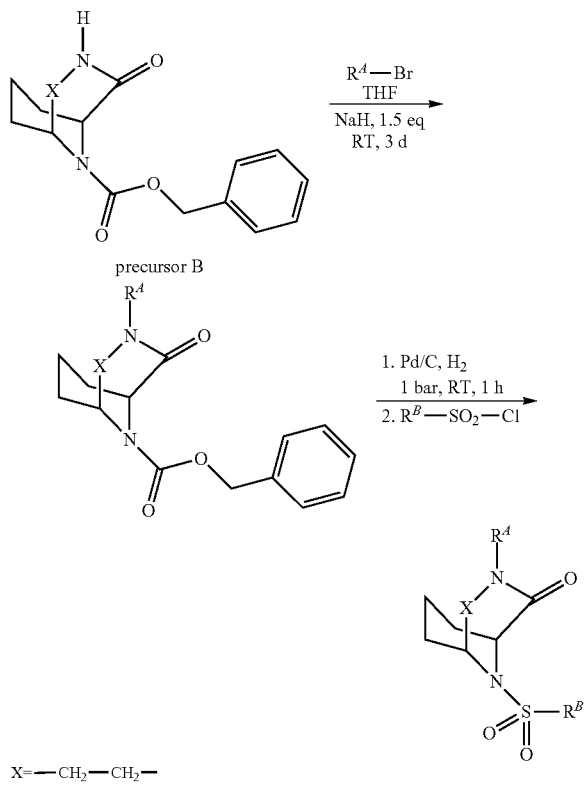

X=—CH$_2$—CH$_2$—

Synthesis of benzyl 3-(2-(3,4-dimethoxyphenoxy)ethyl)-2-oxo-3,10-diazabicyclo[4.3.1]decane-10-carboxylate To a solution of benzyl 2-oxo-3,10-diazabicyclo[4.3.1]decane-10-carboxylate (70 mg, 0.2 mmol) in 2 ml dry THF under argon at 0° C. was added NaH (9 mg, 0.4 mmol) and stirred for 15 min followed by addition of 4-(2-bromoethoxy)-1,2-dimethoxybenzene (158 mg, 0.6 mmol). The reaction was stirred at room temperature for 3 days and concentrated in vacuo. A 10% HCl solution (5 ml) was added and extracted with DCM (4×10 ml). The organic phases were dried over MgSO$_4$, concentrated in vacuo and purified with flash chromatography in hexane: EtOAc 1:3.
TLC [hexane: EtOAc 1:3]: R$_f$=0.49
Yield: 73 mg, 0.2 mmol (64%)
$^1$H-NMR (600 MHz, CDCl$_3$): δ=7.24-7.36 (m, 5H), 6.56 (t, 1H), 6.49 (m, 1H), 6.46-6.48 (m, 1H), 5.12-5.2 (m, 1H), 5.0-5.1 (m, 2H), 4.55-4.65 (m, 1H), 4.0-4.15 (m, 2H), 3.85-3.95 (m, 1H), 3.81-3.84 (m, 6H), 3.55.3.65 (m, 1H), 3.49-3.54 (m, 1H), 3.21-3.27 (m, 1H), 2.3-2.4 (m, 1H), 2.15.2.25 (m, 1H), 1.94-2.01 (m, 1H), 1.4-1.7 (m, 5H)
$^{13}$C-NMR (150 MHz, CDCl$_3$): δ=172.23, 155.96, 153.14, 149.87, 143.63, 136.32, 128.55, 128.47, 128.06, 127.90, 127/6, 111.88, 103.79, 100.38, 67.54, 67.22, 56.41, 56.17, 55.85, 51.22, 47.79, 45.85, 32.24, 28.81, 28.79, 15.29
HRMS (EI): m/z: found 468.2261 [M]$^+$, calculated 468.2260 [M]

Synthesis of 3-(2-(3,4-dimethoxyphenoxy)ethyl)-3,10-diazabicyclo[4.3.1]decan-2-one To a solution of benzyl 8-(2-(3,4-dimethoxyphenoxy)ethyl)-2-oxo-3,10-diazabicyclo[4.3.1]decane-10-carboxylate (60 mg, 0.1 mmol) in 1 ml anhydrous MeOH was added catalytic amounts of Palladium on carbon and degassed with H$_2$. The reaction was stirred under 1 atm H$_2$ at room temperature for 1 h, filtered through celite, concentrated in vacuo and used for the next step without further purification.
TLC [10% MeOH in CHCl$_3$]: R$_f$=0.17
Yield: 41 mg, 0.1 mmol (97%)
$^1$H-NMR (600 MHz, CDCl$_3$): δ=6.76 (d, 1H), 6.50 (d, 1H), 6.40 (m, 1H), 4.08-4.15 (m, 3H), 3.85 (s, 3H), 3.83 (s, 3H), 3.75-3.82 (m, 3H), 3.33-3.35 (m, 1H), 3.2-3.26 (m, 1H), 2.23-2.24 (m, 1H), 1.98-2.12 (m, 2H), 1.5-1.75 (m, 6H)
$^{13}$C-NMR (150 MHz, CDCl$_3$): δ=172.23, 153.27, 149.85, 143.56, 111.90, 103.89, 100.48, 67.32, 57.97, 56.43, 55.86, 51.05, 47.99, 45.91, 33.79, 30.28, 29.68, 29.85.
MS (ESI) m/z: found 335.13 [M+H]$^+$, calculated 335.19 [M+H]$^+$ Synthesis of 10-(3,5-dichlorophenylsulfonyl)-3-(2-(3,4-dimethoxyphenoxy)-ethyl)-3,10-diazabicyclo[4.3.1]decan-2-one 5b 3-(2-(3,4-Dimethoxyphenoxy)ethyl)-3,10-diazabicyclo[4.3.1]decan-2-one (22 mg, 0.07 mmol) in 3 ml DCM was treated with DIPEA (10 mg, 0.08 mmol) and stirred for 30 min at room temperature followed by addition of 3,5-dichlorobenzen sulfony chloride (19 mg, 0.08 mmol). After stirring overnight at room temperature, the reaction was quenched with saturated NH$_4$Cl solution (5 ml), extracted with DCM (4×10 ml). The organic layers were dried over MgSO$_4$ and concentrated in vacuo. The mixture was purified with flash chromatography in cyclohexane: EtOAc 2:1.
TLC [Cyclohexane/EE 1:1]: R$_f$=0.40
Yield: 16 mg, 0.03 mmol (45%) purity >99%
$^1$HNMR (600 MHz, CDCl$_3$) δ=7.69 (s, 1H), 7.68 (s, 1H), 7.48-7.53 (m, 1H), 6.74-6.8 (m, 1H), 6.47-6.5 (m, 1H), 6.36-6.41 (m, 1H), 4.68-4.72 (m, 1H), 4.34-4.42 (m, 1H), 4.07-4.17 (m, 2H), 3.98-4.07 (m, 1H), 3.93-3.98 (m, 1H), 3.86 (s, 3H), 3.82 (s, 3H), 3.64-3.68 (m, 2H), 3.43-3.48 (m, 0.5H), 3.31-3.4 (m, 1.5H), 2.2-2.3 (m, 2H), 1.95-2.05 (m, 2H), 1.55-1.75 (m, 2H)

$^{13}$C NMR (300 MHz, CDCl$_3$) δ=170.50, 153.15, 149.9, 144.15, 143.75, 136.30, 132.63, 124.92, 111.98, 104.06, 100.56, 67.25, 57.05, 56.45, 55.90, 51.42, 51.36, 49.1, 48.2, 32.7, (28.35, 27.9), (14.8, 14.1)

HRMS (EI): m/z: found 542.1045 [M]$^+$, calculated 542.1045 [M]$^+$

Synthesis of 10-(benzo[d]thiazol-6-yisulfonyl)-3-(2-(3,4-dimethoxyphenoxy)-ethyl)-3,10-diazabicyclo[4.3.1]decan-2-one 5c 3-(2-(3,4-Dimethoxyphenoxy)ethyl)-3,10-diazabicyclo[4.3.1]decan-2-one (24 mg, 0.07 mmol) in 3 ml DCM was treated with DIPEA (11 mg, 0.09 mmol) and stirred for 30 min at room temperature followed by addition of 1,3-benzothiazole-6-sulfonyl chloride (20 mg, 0.09 mmol). After stirring overnight at room temperature, the reaction was quenched with saturated NH$_4$Cl solution (5 ml), extracted with DCM (4×10 ml). The organic layers were dried over MgSO$_4$ and concentrated in vacuo. The mixture was purified with Preparative-TLC in 10% MeOH in CHCl$_3$.

TLC [EE]: R$_f$=0.54

Yield: 5 mg, 0.01 mmol (13%) purity >99%

$^1$HNMR (600 MHz, CDCl$_3$) δ=9.18 (s, 1H), 8.48-8.52 (m, 1H), 8.23 (d, 1H, J=8.63 Hz), 7.93 (dd, 1H, J=1.86, 8.64 Hz), 6.77 (d, 1H, J=8.78 Hz), 6.47 (d, 1H, J=2.84 Hz), 6.36-6.39 (m, 1H), 4.74-4.78 (m, 1H), 4.42-4.48 (m, 1H), 4.09-4.15 (m, 2H), 4.02-4.08 (m, 1H), 3.95-3.99 (m, 1H), 3.84 (s, 3H), 0.815-3.825 (m, 3H), 3.6-3.65 (m, 2H), 3.3-3.35 (m, 1H), 3.05-3.1 (m, 1H), 2.25-2.33 (m, 1H), 2.15-2.2 (m, 1H), 1.97-2.03 (m, 1H), 1.7-1.85 (m, 1H), 1.55-1.63 (m, 1H), 1.1-1.2 (m, 1H)

$^{13}$C NMR (300 MHz, CDCl$_3$) δ=166.1, 153.15, 150.70, 148.4, 145.1, 138.93, 133.75, 129.62, 119.86, 119.35, 116.84, 107.10, 99.21, 95.75, 62.45, 52.15, 51.65, 51.12, 44.03, 43.52, 37.15, 24.93, 27.95, 23.02, 17.85

HRMS: m/z: found 532.1560 [M]$^+$, calculated 532.1576 [M+H]$^+$,

Synthesis of 6-(3-(2-(3,4-dimethoxyphenoxyl)ethyl)-2-oxo-3,10-diazabicyclo-[4.3.1]decan-10-ylsulfonyl)benzo[d]thiazol-2(3H)-one 5d 3-(2-(3,4-Dimethoxyphenoxy)ethyl)-3,10-diazabicyclo[4.3.1]decan-2-one (15 mg, 0.05 mmol) in 3 ml DCM was treated with DIPEA (12 mg, 0.09 mmol) and stirred for 30 min at room temperature followed by addition of 2-oxo-2,3-dihydrobenzo[d]thiazole-6-sulfonyl chloride (22 mg, 0.09 mmol). After stirring overnight at room temperature, the reaction was quenched with saturated NH$_4$Cl solution (5 ml), extracted with DCM (4×10 ml). The organic layers were dried over MgSO$_4$ and concentrated in vacuo. The mixture was purified with Preparative-HPLC in 55-65% buffer B in 16 mins.

TLC [EE]: R$_f$=0.54

Yield: 5 mg, 0.01 mmol (20%) purity >99%

$^1$HNMR (300 MHz, DMSO) δ=12.07-12.13 (s, 1H), 7.85-7.88 (m, 1H), 7.56-7.61 (m, 1H), 7.12-7.18 (m, 1H), 6.68-6.73 (m, 1H), 6.67-6.73 (m, 1H), 6.41-6.46 (m, 1H), 6.29-6.34 (m, 1H), 4.54-4.60 (m, 1H), 4.20-4.29 (m, 1H), 3.93-4.02 (m, 2H), 3.75-3.93 (m, 2H), 3.65-3.75 (m, 8H), 3.20-3.27 (m, 1H), 2.15-2.25 (m, 1H), 1.95-2.05 (m, 1H), 1.87-1.93 (m, 1H), 1.05-1.45 (m, 3H)

$^{13}$C NMR (75 MHz, DMSO) δ=175.49, 175.30, 157.94, 154.62, 148.30, 144.97, 139.84, 129.90, 126.01, 125.95, 117.40, 113.70, 109.12, 105.60, 71.41, 61.47, 61.20, 60.57, 55.53, 53.13, 52.60, 37.32, 32.66, 32.36, 19.54

HRMS (EI) m/z: found 547.1446 [M]$^+$, calculated 547.1447 [M]$^+$

Synthesis of 3,10-diazabicyclo[4.3.1]decan-2-one 32

To a solution of benzyl 2-oxo-3,10-diazabicyclo[4.3.1]decane-10-carboxylate 19 (precursor B, 33 mg, 0.1 mmol) in 1 ml anhydrous MeOH was added catalytic amounts of Palladium on carbon and degassed with H$_2$. After stirring under 1 atm H$_2$ at room temperature for 3 h, the reaction mixture was filtered through celite, concentrated in vacuo and used for the next step without further purification.

TLC [20% MeOH in CHCl$_3$]: R$_f$=0.26

Yield: 17 mg, 0.1 mmol (100%)

Synthesis of 6-(2-oxo-3,10-diazabicyclo[4.3.1]decan-10-ylsulfonyl)benzo[d]-thiazol-2(3H)-one 5e 3,10-Diazabicyclo[4.3.1]decan-2-one (17 mg, 0.1 mmol) in 1 ml DCM under argon was treated with DIPEA (43 mg, 0.3 mmol) and stirred for 30 min at room temperature followed by addition of 2-oxo-2,3-dihydrobenzo[d]thiazole-6-sulfonyl chloride (33 mg, 0.1 mmol). After stirring overnight at room temperature, the reaction was quenched with saturated NH$_4$Cl solution (5 ml), extracted with DCM (4×10 ml). The organic layers were dried over MgSO$_4$ and concentrated in vacuo. The mixture was purified with Preparative-HPLC in 45% buffer B in 16 mins.

TLC [10% MeOH in DCM]: R$_f$=0.72

Yield: 5 mg, 0.01 mmol (12%) purity >98%

$^1$HNMR (600 MHz, DMSO) δ=8.19 (d, 1H, J=1.93 Hz), 7.90-7.95 (m, 1H), 7.73 (dd, 1H, J=1.98, 8.43 Hz), 7.25 (d, 1H, J=8.44 Hz), 4.39-4.43 (m, 1H), 4.25-4.31 (m, 1H), 3.25-3.30 (m, 1H), 2.84-2.9 (m, 1H), 2.03-2.17 (m, 1H), 1.85-1.93 (m, 1H), 1.67-1.77 (m, 1H), 1.42-1.50 (m, 1H), 1.17-1.33 (m, 2H), 1.05-1.15 (m, 2H)

$^{13}$C NMR (300 MHz, DMSO) δ=172.4, 170.8, 140.4, 135.3, 125.5, 124.9, 122.1, 112.3, 56.3, 49.1, 38.9, 33.25, 28.0, 26.9, 14.8

HRMS: m/z: found 368.0736 [M+H]$^+$, calculated 368.0739 [M+H]$^+$

Synthesis of 10-(3,5-dichloro-4-hydroxyphenylsulfonyl)-3-(2-(3,4-dimethoxy-phenoxy)ethyl)-3,10-diazabicyclo[4.3.1]decan-2-one 5i The 3-(2-(3,4-dimethoxyphenoxy)ethyl)-3,10-diazabicyclo[4.3.1]decan-2-one (24 mg, 0.07 mmol) in 3 ml DCM was treated with DIPEA (23 mg, 0.09 mmol) and stirred for 30 min at room temperature followed by addition of Benzenesulfonylchloride, 3,5-dichloro-4-hydroxy (23 mg, 0.09 mmol). After stirring overnight at room temperature, the reaction was quenched with saturated NH$_4$Cl solution (5 ml), extracted with DCM (4×10 ml). The organic layers were dried over MgSO$_4$ and concentrated in vacuo. The mixture was purified with flash chromatography in EE followed by 10% MeOH in CHCl$_3$.

TLC [EE]: R$_f$=0.6

Yield: 10 mg, 0.02 mmol (25%) purity >98%

$^1$HNMR (300 MHz, CDCl$_3$) δ=7.78 (s, 2H), 6.76-6.82 (m, 1H), 6.5-6.54 (m, 1H), 6.38-6.44 (m, 1H), 4.68-4.74 (m, 1H), 4.3-4.45 (m, 1H), 3.93-4.24 (m, 3H), 3.85-3.9 (m, 7H), 3.6-

3.73 (m, 3H), 3.3-3-45 (m, 1H), 2.2-2.4 (m, 2H), 1.95-2.1 (m, 2H), 1.6-1.7 (m, 1H), 1.35-1.45 (m, 1H)
$^{13}$C NMR (75 MHz, CDCl$_3$) δ=170.4, 153.14, 151.5, 149.9, 143.7, 134.4, 126.83, 122.09, 111.99, 104.07, 100.59, 67.25, 56.93, 56.46, 55.91, 51.43, 51.35, 48.91, 48.27, 31.92, 22.69, 14.11
HRMS (EI): m/z: found 558.0993 [M]$^+$, calculated 558.0994 [M]$^+$
Example 4
Compounds No. 5 with X=—CH(CH=CH$_2$)—CH$_2$—
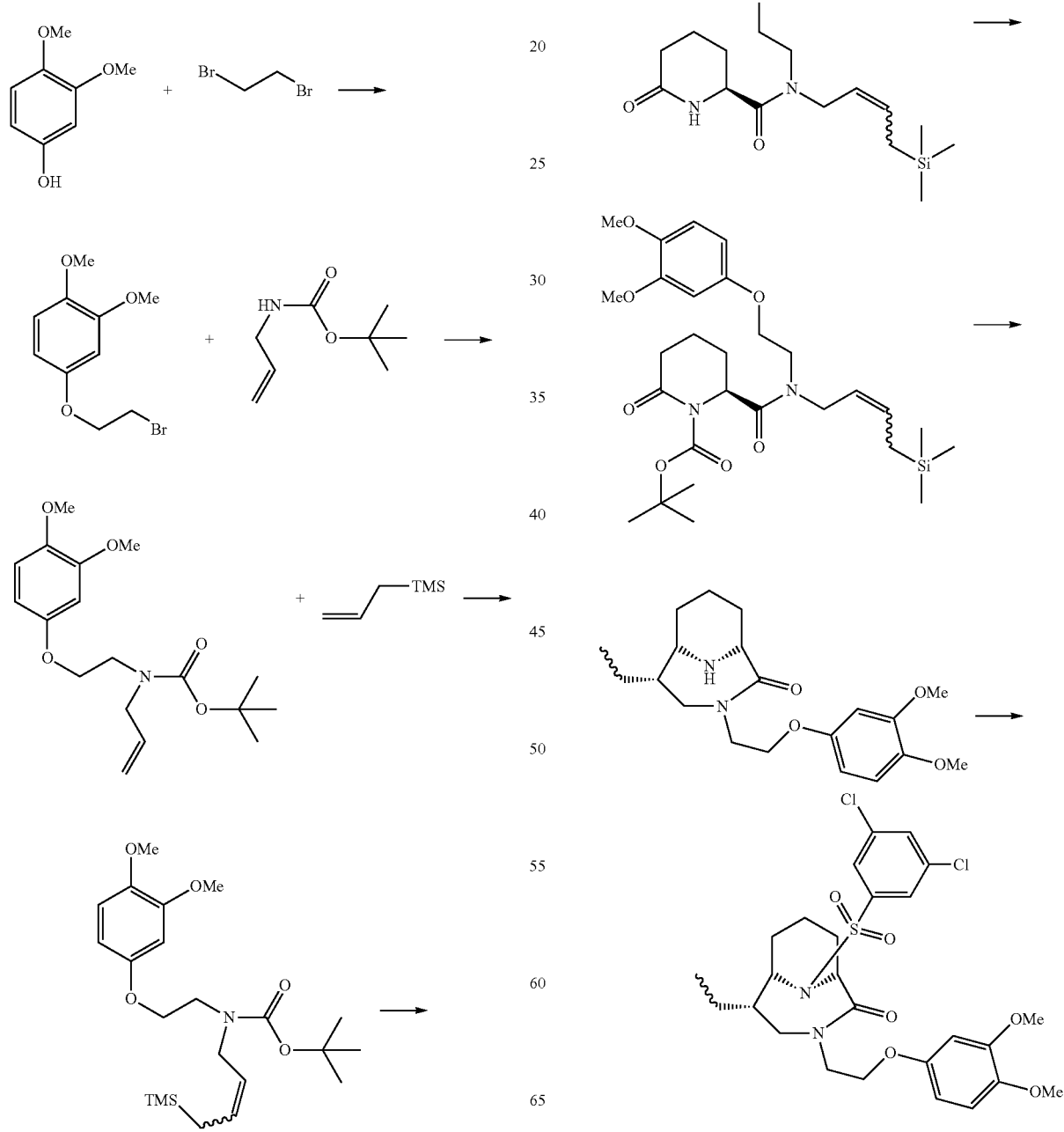

Synthesis of 4-(2-bromoethoxy)-1,2-dimethoxybenzene

To a solution of 2,3-dimethoxyphenol in acetone was added an equimolar amount of 1,2-dibromoethane and excess K$_2$CO$_3$ and heated under reflux overnight. The reaction mixture was filtered and the solvent was evaporated in vacuo. The pure product was obtained with flash chromatography in cyclohexane: EtOAc 5:1 in 46% yield.

Synthesis of tert-butyl allyl(2-(3,4-dimethoxyphenoxyl)ethyl)carbamate

To a solution of tert-butyl N-allylcarbamate (144 mg, 0.92 mmol) in 1 ml DMF was added NaH (22 mg, 0.92 mmol) under argon and the reaction mixture was stirred for 30 min at 0° C. followed by addition of 4-(2-bromoethoxy)-1,2-dimethoxybenzene (200 mg, 0.77 mmol) and stirring at 0° C. for 2 h. To the mixture a saturated NH$_4$Cl solution (10 ml) was added and extracted with DCM (5×10 ml), dried over MgSO$_4$, filtered and concentrated in vacuo. The pure product was obtained with flash chromatography in cyclohexane: EtOAc 5:1.

TLC [cyclohexane: EtOAc 5:1]: R$_f$=0.26
Yield: 178 mg, 0.53 mmol (69%)
$^1$HNMR (400 MHz, CDCl$_3$) δ=6.76 (d, 1H, J=8.75 Hz), 6.49 (s, 1H), 6.31-6.43 (m, 1H), 5.70-5.90 (m, 1H), 5.02-5.23 (m, 2H), 3.98-4.08 (m, 2H), 3.88-3.98 (m, 2H), 3.84 (s, 3H), 3.81 (s, 3H), 3.55 (s, 2H), 1.45 (s, 9H)
MS (ESI): m/z: found 337.93 [M+Na]$^+$, calculated 338.19 [M+H]$^+$

Synthesis of tert-butyl 2-(3,4-dimethoxyphenoxyl) ethyl(4-(trimethylsilyl)but-2-enyl)carbamate To a solution of tert-butyl allyl(2-(3,4-dimethoxyphenoxyl)ethyl)carbamate (100 mg, 0.30 mmol) and allyltrimethylsilane (135 mg, 1.18 mmol) in 3 ml DCM was added Grubbs catalyst generation I (24 mg, 0.03 mmol, Sigma-Aldrich) and heated under reflux overnight. The mixture was filtered through celite and concentrated in vacuo. The pure product was obtained by flash chromatography with cyclohexane: EtOAc 6:1

TLC [cyclohexane: EtOAc 6:1]: R$_f$=0.38
Yield: 85 mg, 0.20 mmol (67%)
$^1$HNMR (400 MHz, CDCl$_3$) δ=6.73-6.82 (m, 1H), 6.46-6.56 (m, 1H), 6.35-6.45 (m, 1H), 5.45-5.67 (m, 1H), 5.18-5.45 (m, 1H), 3.87-4.15 (m, 4H), 3.86 (s, 3H), 3.84 (s, 3H), 3.43-3.63 (m, 2H), 1.50-1.75 (m, 2H), 1.47 (s, 9H), −0.09-0.03 (m, 9H)
$^{13}$C NMR (100 MHz, CDCl$_3$) δ=155.50, 153.33, 149.89, 143.55, 129.55, 123.57, 111.91, 103.80, 100.82, 79.54, 67.02, 56.45, 55.82, 50.01, 45.50, 28.45, 22.69, −1.81
MS (ESI): m/z: found 446.93 [M+Na]$^+$, calculated 446.60 [M+Na]$^+$

Synthesis of N-(2-(3,4-dimethoxyphenoxyl)ethyl)-4-(trimethylsilyl)but-2-en-1-amine Excess amount of SiO$_2$ was added to tert-butyl 2-(3,4-dimethoxyphenoxyl)ethyl(4-(trimethylsilyl)but-2-enyl)carbamate (220 mg, 0.52 mmol) and stirred at 150° C. in vacuo for 2 h. It was washed with EtOAc for 3 times and the organic layers were collected and concentrated in vacuo. The compound was used for the next step without further purification.
TLC [5% TEA in EtOAc]: R$_f$=0.6
Yield: 143 mg, 0.44 mmol (85%)

MS (ESI): m/z: found 323.93 [M+H]$^+$, calculated 324.20 [M+H]$^+$

Synthesis of (S)—N-(2-(3,4-dimethoxyphenoxyl) ethyl)-6-oxo-N-(4-(trimethylsilyl)but-2-enyl)piperidine-2-carboxamide To a solution of (S)-6-oxo-2-piperidinecarboxylic acid (109 mg, 0.76 mmol) in 5 ml DCM was added sequentially with DIPEA (205 mg, 1.58 mmol), HOAt (104 mg, 0.76 mmol), EDC-HCl (118 mg, 0.76 mmol) and stirred for 30 min at room temperature followed by addition of N-(2-(3,4-dimethoxyphenoxyl)ethyl)-4-(trimethylsilyl)but-2-en-1-amine (205 mg, 0.63 mmol). After 24 h, brine (10 ml) was added and extracted with DCM (5×10 ml), dried over MgSO$_4$, filtered and concentrated in vacuo. The pure product was obtained by flash chromatography with 5% TEA in EtOAc.

TLC [5% TEA in EtOAc]: R$_f$=0.27
Yield: 260 mg, 0.58 mmol (90%)
MS (ESI): m/z: found 449.57 [M+H]$^+$, calculated 449.24 [M+H]$^+$

Synthesis of (S)-tert-butyl 24(2-(3,4-dimethoxyphenoxyl)ethyl)(4-(trimethylsilyl)but-2-enyl)carbamoyl)-6-oxopiperidine-1-carboxylate To a solution of (S)—N-(2-(3,4-dimethoxyphenoxyl) ethyl)-6-oxo-N-(4-(trimethylsilyl)but-2-enyl)piperidine-2-carboxamide (1102 mg, 2.46 mmol) in 20 ml THF was added BuLi (189 mg, 2.95 mmol) dropwise under argon at −78° C. and stirred for 1 h followed by addition of di-tert-butyl dicarbonate (1072 mg, 4.91 mmol). After 5 h at −78° C., a saturated NH$_4$Cl solution (20 ml) was added at room temperature and extracted with DCM (6×20 ml), dried over MgSO$_4$, filtered and concentrated in vacuo. The pure product was obtained by flash chromatography with cyclohexane: EtOAc 1:1.

TLC [cyclohexane: EtOAc 1:1]: R$_f$=0.4
Yield: 617 mg, 1.12 mmol (46%)
$^1$HNMR (400 MHz, CDCl$_3$) δ=6.72-6.79 (m, 1H), 6.44-6.53 (m, 1H), 6.31-6.42 (m, 1H), 5.55-5.75 (m, 1H), 5.15-5.45 (m, 1H), 4.95-5.05 (m, 1H), 3.95-4.25 (m, 4H), 3.77-3.90 (m, 6H), 3.55-3.77 (m, 2H), 2.54-2.65 (m, 1H), 2.35-2.50 (m, 1H), 1.50-1.65 (m, 4H), 1.38-1.49 (m, 9H), 0 (t, 9H, J=12.30, 12.30 Hz)
$^{13}$C NMR (100 MHz, CDCl$_3$) δ=171.37, 171.13, 153.13, 153.09, 149.76, 143.51, 131.93, 122.53, 111.80, 103.95, 100.51, 83.04, 66.64, 55.82, 55.57, 51.36, 45.29, 34.40, 27.96, 25.84, 22.91, 19.13, −1.92
MS (ESI): m/z: found 571.34 [M+H]$^+$, calculated 571.28 [M+H]$^+$

Synthesis of (1S,5S,6R)-3-(2-(3,4-dimethoxyphenoxyl)ethyl)-5-vinyl-3,10-diazabicyclo[4.3.1]decan-2-one To a solution of (S)-tert-butyl 24(2-(3,4-dimethoxyphenoxyl)ethyl)(4-(trimethylsilyl)but-2-enyl)carbamoyl)-6-oxopiperidine-1-carboxylate (100 mg, 0.18 mmol) in 1 ml THF under argon was added DIBAL-H (78 mg, 0.55 mmol) dropwise and stirred at −78° C. for 1 h followed by removal of solvent in vacuo. The oily residue in 1 ml DCM was treated with 1 ml 10% TFA in DCM at −78° C. dropwise and stirred at 0° C. for 2 h followed by addition of 1 mL TFA and stirring for another 2 h. A saturated NaHCO$_3$ solution (10 ml) was added and extracted with DCM (6×10 ml), dried over MgSO₄, filtered and concentrated in vacuo. The pure product was obtained by Preparative-TLC with 5% MeOH, 5% TEA in EtOAc.

TLC [5% MeOH, 5% TEA in EtOAc]: $R_f$=0.38
Yield: 50 mg, 0.14 mmol (76%)
¹HNMR (400 MHz, CDCl₃) δ=6.77 (d, 1H, J=8.76 Hz), 6.49 (d, 1H, J=2.81 Hz), 6.38 (dd, 1H, J=2.84, 8.73 Hz), 5.65-5.76 (m, 1H), 5.07 (s, 1H), 5.01-5.05 (m, 1H), 4.22-4.30 (m, 1H), 4.13-4.20 (m, 1H), 3.99-4.10 (m, 2H), 3.84-3.90 (m, 1H), 3.83 (s, 3H), 3.82 (s, 3H), 3.55-3.78 (m, 1H), 3.26-3.35 (m, 1H), 2.97-3.04 (m, 1H), 2.73-2.83 (m, 1H), 2.23-2.32 (m, 1H), 1.69-1.82 (m, 2H), 1.48-1.68 (m, 4H)
¹³C NMR (100 MHz, CDCl₃) δ=172.90, 153.11, 149.81, 143.56, 138.58, 115.55, 111.77, 103.46, 100.48, 67.33, 57.00, 56.40, 55.79, 52.73, 52.51, 51.34, 48.88, 28.70, 27.28, 16.24
MS (ESI): m/z: found 361.09 [M+H]⁺, calculated 361.21 [M+H]⁺

Synthesis of (1S,5S,6R)-10-(3,5-dichlorophenylsulfonyl)-3-(2-(3,4-dimethoxy-phenoxy)ethyl)-5-vinyl-3,10-diazabicyclo[4.3.1]decan-2-one 5k To a solution (1S,5S,6R)-3-(2-(3,4-dimethoxyphenoxyl)ethyl)-5-vinyl-3,10-diazabicyclo[4.3.1]decan-2-one (80 mg, 0.22 mmol) in 1 mL DCM under argon was treated with DIPEA (34.4 mg, 0.266 mmol) and stirred for 30 min at room temperature followed by addition of 3,5-dichlorobenzene sulfonyl chloride (65 mg, 0.27 mmol). After stirring overnight at room temperature, the pure product was obtained by Preparative-TLC with cyclohexane: EtOAc 1:1.

TLC [cyclohexane: EtOAc 1:1]: $R_f$=0.68
Yield: 60 mg, 0.11 mmol (48%)
¹HNMR (600 MHz, CDCl₃) δ=7.68 (d, 2H, J=1.85 Hz), 7.53 (t, 1H, J=1.85, 1.85 Hz), 6.76 (d, 1H, J=8.77 Hz), 6.46 (d, 1H, J=2.79 Hz), 6.36 (dd, 1H, J=2.81, 8.75 Hz), 5.77-5.86 (m, 1H), 5.05-5.16 (m, 2H), 4.65-4.71 (m, 1H), 4.07-4.21 (m, 3H), 3.99-4.05 (m, 1H), 3.94-3.98 (m, 1H), 3.83 (s, 3H), 3.82 (s, 3H), 3.45-3.53 (m, 1H), 3.22-3.3 (m, 1H), 2.67-2.76 (m, 1H), 2.24 (d, 1H, J=13.52 Hz), 1.42-1.53 (m, 3H), 1.14-1.22 (m, 2H)
¹³C NMR (150 MHz, CDCl₃) δ=170.18, 153.04, 149.83, 144.05, 143.66, 137.52, 136.31, 132.67, 124.84, 116.54, 111.81, 103.52, 100.52, 67.29, 56.80, 56.40, 55.79, 54.92, 53.39, 51.60, 49.25, 27.60, 26.27, 15.41
MS (ESI): m/z: found 570.62 [M+H]⁺, calculated 570.51 [M+H]

Example Comparative Examples

General route to the corresponding reference structures 3a to 3d:

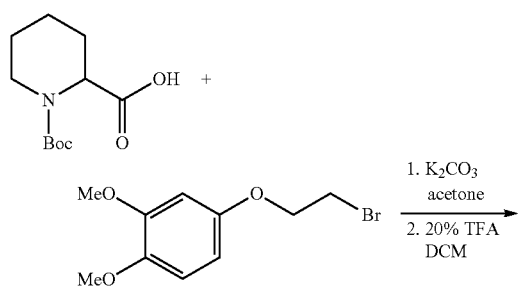

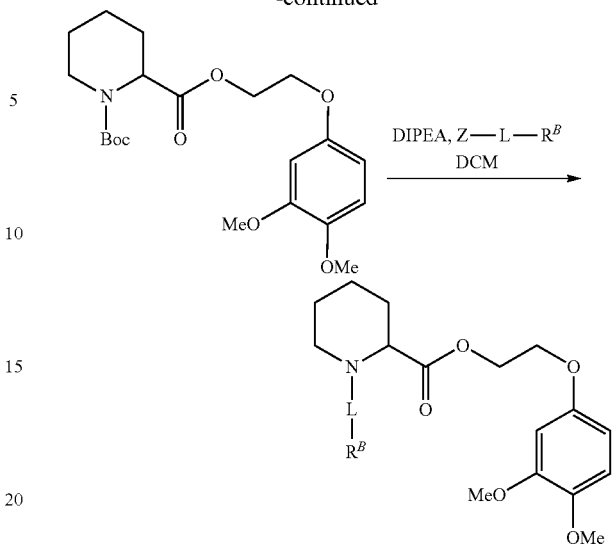

wherein L represents —CO—CO— or —SO₂—, and wherein Z represents H when L represents —CO—CO—, and wherein Z represents —Cl when L represents —SO₂—.

Comparative Examples 4a, 4f, 4g, 5a, 5f and 5h were prepared according to the procedures below.

Synthesis of 2-(3,4-dimethoxyphenoxyl)ethyl piperidine-2-carboxylate 1-tert-Butyl 2-(2-(3,4-dimethoxyphenoxy)ethyl) piperidine-1,2-dicarboxylate (456 mg, 1.1 mmol), prepared by reacting 1-tert-butyl-piperidine-1,2-dicarboxylate and 4-(2-bromoethoxy)-1,2-dimethoxybenzene in acetone in the presence of potassium carbonate, was dissolved in 10 ml 20% TFA in DCM and was stirred at room temperature for 2 h. The reaction mixture was concentrated in vacuo and used for next step without further purification.

TLC [hexane:EtOAc:TEA 7.5:2.3:0.4]: $R_f$=0.19
Yield: 344 mg, 1.1 mmol (100%)
¹H NMR (600 MHz, CDCl₃) δ=6.76 (d, 1H, J=9 Hz), 6.50 (d, 1H, J=3 Hz), 6.35 (dd, 1H, J=3, 9 Hz), 4.45-4.54 (m, 2H), 4.11 (t, 2H, J=4.2 Hz), 3.92 (dd, 1H, J=3.6, 11.4 Hz), 3.83 (s, 3H), 3.82 (s, 3H), 3.55 (d, 1H, J=12.6 Hz), 2.99-3.04 (m, 1H), 2.24-2.28 (m, 1H), 1.82-1.97 (m, 4H), 1.54-1.61 (m, 1H),
¹³C NMR (150 MHz, CDCl₃) δ=168.48, 152.71, 149.91, 143.98, 111.74, 103.94, 100.97, 65.85, 64.71, 56.83, 56.39, 55.81, 44.14, 25.60, 21.74, 21.50,
HRMS (EI): m/z: found 309.1580 [M]⁺, calculated 309.1576 [M]⁺

Synthesis of 2-(3,4-dimethoxyphenoxyl)ethyl 1-(2-oxo-2-(3,4,5-trimethoxy-phenyl)acetyl)piperidine-2-carboxylate 3a 2-(3,4-Dimethoxyphenoxyl)ethyl piperidine-2-carboxylate (50 mg, 0.2 mmol) in 10 ml acetonitrile under argon was treated sequentially with DIPEA (63 mg, 0.5 mmol), 2-oxo-2-(3,4,5-trimethoxyphenyl) acetic acid (44 mg, 0.2 mmol) and HATU (58 mg, 0.2 mmol). After stirring at room temperature for 3 days, it was concentrated in vacuo followed by addition of 5 ml H₂O and extraction with DCM (3×10 ml). The organic phases were dried over MgSO₄, concentrated in vacuo and purified with flash chromatography in hexane: EtOAc 3:1

TLC [hexane: EtOAc 1:1]: R$_f$=0.32

Yield: 36 mg, 0.07 mmol (42%) purity >99%

$^1$HNMR (300 MHz, CDCl$_3$) δ=7.33-7.39 (m, 1.5H), 7.21-7.23 (m, 0.5H), 6.73-6.8 (m, 1H), 6.46-6.54 (m, 1H), 6.3-6.43 (m, 1H), 5.41-5.46 (m, 1H), 4.5-4.65 (m, 2H), 4.1-4.2 (m, 2H), 3.94 (d, 9H, J=1.96 Hz), 3.84 (d, 6H, J=2.16 Hz), 3.22-3.54 (m, 2H), 2.2-2.44 (m, 2H), 1.73-1.88 (m, 2H), 1.51-1.69 (m, 2H)

$^{13}$C NMR (300 MHz, CDCl$_3$) δ=(190.83, 190.34), (170.44, 170.19), (167.89, 166.87), (153.54, 153.27), (152.92, 152.78), (149.96, 149.92), (144.01, 143.99), (128.11, 128.01), (111.78, 111.76), 107.25, 107.00, (104.05, 104.0), (101.16, 101.08), (66.34, 66.27), (63.80, 63.78), (60.98, 60.35), 56.43, 56.41, 56.31, 55.87, 51.75, 44.26, 26.31, 24.75, (21.16, 21.02)

HRMS (EI): m/z: found 531.2105 [M]$^+$, calculated 531.2104 [M]$^+$

Synthesis of 2-(3,4-dimethoxyphenoxyl)ethyl 1-(3,5-dichlorophenyisulfonyl)-piperidine-2-carboxylate 3b 2-(3,4-Dimethoxyphenoxyl)ethyl piperidine-2-carboxylate (50 mg, 0.16 mmol) in 1 ml DCM was treated with DIPEA (63 mg, 0.49 mmol) and stirred for 30 min at room temperature followed by addition of 3,5-dichlorobenzen sulfony chloride (40 mg, 0.16 mmol). After stirring overnight at room temperature, the reaction was quenched with saturated NH$_4$Cl solution (5 ml), extracted with DCM (4×10 ml). The organic layers were dried over MgSO$_4$ and concentrated in vacuo. The mixture was purified with Preparative-TLC in cyclohexane:EtOAc 3:1.

TLC [cyclohexane: EtOAc 3:1]: R$_f$=0.57

Yield: 17 mg, 0.03 mmol (20%) purity >99%

$^1$HNMR (600 MHz, CDCl$_3$) δ=7.64 (d, 2H, J=1.85 Hz), 7.49 (t, 1H, J=1.86, 1.86 Hz), 6.76 (d, 1H, J=8.76 Hz), 6.48 (d, 1H, J=2.8 Hz), 6.34 (dd, 1H, J=2.83, 8.73 Hz), 4.75-4.8 (m, 1H), 4.35-4.4 (m, 1H), 4.25-4.3 (m, 1H), 4.03-4.08 (m, 1H), 3.97-4.03 (m, 1H), 3.83 (d, 6H, J=7.88 Hz), 3.72-3.77 (m, 1H), 3.16-3.24 (m, 1H), 2.16-2.21 (m, 1H), 1.73-1.85 (m, 1H), 1.65-1.71 (m, 1.8H), 1.47-1.63 (m, 2H), 1.33-1.36 (m, 0.5H)

$^{13}$C NMR (300 MHz, CDCl$_3$) δ=170.23, 152.82, 149.92, 143.99, 142.67, 135.64, 132.29, 125.55, 111.76, 103.99, 101.06, 66.13, 63.48, 56.41, 55.85, 55.31, 42.88, 27.92, 24.73, 19.88

HRMS: m/z: found 518.1343 [M+H]$^+$, calculated 518.0807 [M+H]

Synthesis of 2-(3,4-dimethoxyphenoxyl)ethyl 1-(benzo[d]thiazol-6-ylsulfonyl)-piperidine-2-carboxylate 3c 2-(3,4-Dimethoxyphenoxyl)ethyl piperidine-2-carboxylate (50 mg, 0.16 mmol) in 1 ml DCM under argon was treated sequentially with DIPEA (42 mg, 0.32 mmol) and 1,3-benzothiazole-6-sulfonyl chloride (76 mg, 0.32 mmol). After stirring at room temperature overnight, the reaction was quenched with saturated NH$_4$Cl solution (5 ml), extracted with DCM (4×10 ml). The organic layers were dried over MgSO$_4$ and concentrated in vacuo. The mixture was purified with flash chromatography in cyclohexane: EtOAc 1:1.

TLC [cyclohexane: EtOAc 1:1]: R$_f$=0.3

Yield: 39 mg, 0.077 mmol (48%) purity >98%

$^1$HNMR (300 MHz, CDCl$_3$) δ=9.18-9.22 (m, 1H), 8.47-8.51 (m, 1H), 8.19-8.24 (m, 1H), 7.90-7.96 (m, 1H), 6.75-6.81 (m, 1H), 6.47-6.51 (m, 1H), 6.31-6.37 (m, 1H), 4.85-4.91 (m, 1H), 4.09-4.38 (m, 2H), 3.89-4.05 (m, 2H), 3.83-3.89 (d, 6H, J=2.01 Hz), 3.74-3.83 (m, 1H), 3.21-3.34 (m, 1H), 2.15-2.25 (m, 1H), 1.74-1.88 (m, 1H), 1.62-1.74 (m, 2H), 1.3-1.62 (m, 2H)

$^{13}$C NMR (75 MHz, CDCl$_3$) δ=170.56, 157.63, 155.2, 152.84, 149.94, 144.01, 137.34, 133.95, 124.98, 123.98, 122.00, 111.80, 104.07, 101.09, 66.16, 63.37, 56.44, 55.89, 55.21, 42.80, 27.94, 24.75, 19.98

LCMS Rt=12.08 MS 507.25 [M+H]$^+$, calculated 507.12 [M+H]$^+$,

HRMS: m/z: found 507.1779 [M+H]$^+$, calculated 507.1260 [M+H]$^+$

Synthesis of ethyl 1-(2-oxo-2,3-dihydrobenzo[d]thiazol-6-ylsulfonyl)piperidine-2-carboxylate 3d To ethyl piperidine-2-carboxylate (50 mg, 0.32 mmol) DIPEA (124 mg, 0.96 mmol) and the 2-oxo-2,3-dihydrobenzo[d]thiazole-6-sulfonyl chloride (88 mg, 0.35 mmol) were added. The reaction was stirred at room temperature overnight and purified by flash chromatography.

TLC (Hexane: EtOAc 1:1): Rf=0.18 yield=106 mg, 0.29 mmol (91%) purity >99%

1HNMR (300 MHz, CDCl3) δ=1.169 (3H, t, J=6.9 Hz), 1.46-1.83 (m, 7H), 2.05-2.17 (m, 1H), 3.72-3.78 (m, 1H), 3.94-4.08 (m, 2H), 4.74 (d, 1H, J=4.8 Hz), 7.27 (s, 1H), 7.67-7.70 (m, 1H), 7.84 (d, 1H, J=0.9 Hz).

13C NMR (75 MHz, CDCl3) δ=172.11, 170.68, 138.88, 134.62, 125.87, 124.59, 121.84, 111.64, 61.27, 55.16, 42.68, 27.94, 24.75, 19.99, 14.12

HRMS 370.0655 [M]$^+$, calculated 370.0657 [M]$^+$.

Synthesis of (S)-2-(3,4-dimethoxyphenoxyl)ethyl 1-(3,3-dimethyl-2-oxopentanoyl)piperidine-2-carboxylate 3e 3e was prepared as described in Gopalakrishnan J. Med Chem 2012, 55/9, 4114-22

Synthesis of 1-(3-(2-(3,4-dimethoxyphenoxyl)ethyl)-2-oxo-3,9-diazabicyclo[3.3.1]nonan-9-yl)-2-(3,4,5-trimethoxyphenyl)ethane-1,2-dione 4a 3-(2-(3,4-Dimethoxyphenoxyl)ethyl)-3,9-diazabicyclo[3.3.1]nonan-2-one (35 mg, 0.1 mmol) in 6 ml DCM was treated sequentially with 2-oxo-2-(3,4,5-trimethoxyphenyl) acetic acid (29 mg, 0.1 mmol), EDC-HCl (20 mg, 0.1 mmol), HOBt (18 mg, 0.1 mmol), TEA (13 mg, 0.1 mmol) at room temperature and stirred overnight. The reaction was quenched with saturated NH$_4$Cl solution (5 ml), extracted with DCM (4×10 ml). The organic layers were dried over MgSO$_4$ and concentrated in vacuo. The mixture was purified with flash chromatography in EtOAc.

TLC [EtOAc]: R$_f$=0.54

Yield: 14 mg, 0.03 mmol (24%) purity >99%

$^1$HNMR (600 MHz, CDCl$_3$) δ=7.19 (d, 2H, J=22.63), 6.72-6.8 (m, 1H), 6.42-6.48 (m, 1H), 6.34-6.39 (m, 1H), 5.22 (s, 0.5H), 5.07 (s, 0.5H), 4.17-4.27 (m, 1.5H), 4.08-4.16 (m, 1.5H), 4.04-4.07 (m, 0.5H), 3.97-4.04 (m, 1.5H), 3.94 (d, 3H, J=7.39), 3.79-3.92 (m, 12H), 3.62-3.65 (m, 0.5H), 3.47-3.56 (m, 1.5H), 2.13-2.18 (m, 0.5H), 1.93-2.02 (m, 1.5H), 1.79-1.9 (m, 2H), 1.7-1.78 (m, 2H)

$^{13}$C NMR (300 MHz, CDCl$_3$) δ=(189.57, 189.30), (167.24, 166.73), (163.90, 163.38), 153.43, 153.39, (152.77, 152.76), (149.92, 149.90), (144.48, 144.46), (143.88, 143.85), (127.86, 127.74), (111.87, 111.85), (107.09, 107.00), (103.94, 103.85), (100.36, 100.35), (66.81, 66.80), (61.07, 61.04), 60.38, (56.39, 56.36), (56.29, 56.14), (55.89, 55.86), (53.39, 52.68), 51.17, 49.36, (46.71, 46.55), 42.84, (31.35, 30.49), (28.95, 28.30), (18.03, 17.92)

HRMS (EI): m/z: found 542.2264 [M]$^+$, calculated 542.2264 [M]$^+$

Synthesis of 3,3-dimethyl-2-oxopentanoic acid 25e

To a suspension of NaOH (175 mg, 4.4 mmol) and KMnO$_4$ (543 mg, 3.4 mmol) in 5 ml water at 0° C. was added 3,3-dimethyl-2-pentanone (200 mg, 1.8 mmol). After stirring for 1 h at 0° C. and 3 days at room temperature, the reaction was acidified with concentrated HCl and extracted with DCM (4×10 ml). The organic phases were dried over MgSO$_4$, concentrated in vacuo and purified with flash chromatography in hexane: EtOAc 5:1.

TLC [hexane: EtOAc 5:1]: R$_f$=0.45

Yield: 97 mg, 0.7 mmol (39%)

$^1$HNMR (300 MHz, CDCl$_3$) δ=1.61 (q, 2H, J=7.49, 7.49, 7.51 Hz), 1.21 (s, 6H), 0.91 (t, 3H, J=7.49, 7.49 Hz), $^{13}$C NMR (150 MHz, CDCl$_3$) δ=9.18, 24.38, 33.13, 42.49, 185.25

Synthesis of Reference Example 1-(3-(2-(3,4-dimethoxyphenoxyl)ethyl)-2-oxo-3,9-diazabicyclo-[3.3.1]nonan-9-yl)-3,3-dimethylpentane-1,2-dione 4f 3-(2-(3,4-Dimethoxyphenoxyl)ethyl)-3,9-diazabicyclo [3.3.1]nonan-2-one (20 mg, 0.06 mmol) in 3 ml DCM was treated sequentially with 3,3-dimethyl-2-oxopentanoic acid (18 mg, 0.13 mmol), EDC-HCl (23 mg, 0.13 mmol), HOBt (17 mg, 0.13 mmol), TEA (8 mg, 0.08 mmol) at room temperature and stirred overnight. The reaction was quenched with saturated NH$_4$Cl solution (5 ml), extracted with DCM (4×10 ml). The organic layers were dried over MgSO$_4$ and concentrated in vacuo. The mixture was purified with flash chromatography in EtOAc.

TLC [EtOAc]: R$_f$=0.6

Yield: 21 mg, 0.05 mmol (76%) purity >98%

$^1$HNMR (600 MHz, CDCl$_3$) δ=6.74 (d, 1H, J=8.76 Hz), 6.44 (t, 1H, J=2.86, 2.86 Hz), 6.35 (dt, 1H, J=2.95, 2.95, 8.74 Hz), 5.04 (s, 0.5H), 4.89 (s, 0.5H), 4.16 (ddd, 2H, J=6.88, 11.94, 14.20 Hz), 3.85-4.03 (m, 2.5H), 3.83 (d, 3H, J=2.67 Hz), 3.80 (s, 3H), 3.69-3.75 (m, 1H), 3.56-3.63 (m, 0.5H), 3.46-3.54 (m, 1H), 1.95-2.1 (m, 1H), 1.75-1.9 (m, 3H), 1.65-1.57 (m, 4H), 1.16-1.26 (m, 3H), 1.11 (d, 3H, J=5.56 Hz), 0.78-0.88 (m, 3H)

$^{13}$C NMR (300 MHz, CDCl$_3$) δ=(207.03, 206.85), (167.30, 166.9), (164.44, 163.63), (152.85, 152.84), 149.88, 143.81, (111.92, 111.87), (103.99, 103.83), (100.43, 100.42), (67.92, 25.57), (66.82, 66.59), (56.39, 56.09), (55.86, 55.83), (53.36, 52.50), (50.76, 42.32), (48.16, 46.47), (46.71, 46.64), (32.40, 32.32), (31.26, 27.96), (30.19, 28.51), (23.63, 23.37), (23.33, 22.84), (18.00, 17.94), (8.84, 8.71)

HRMS: m/z: found 446.2413[M+H], calculated 446.2417 [M+H]$^+$

Synthesis of benzyl 3-ethyl-2-oxo-3,9-diazabicyclo [3.3.1]nonane-9-carboxylate

To a solution of benzyl 2-oxo-3,9-diazabicyclo[3.3.1] nonane-9-carboxylate (500 mg, 1.8 mmol) in 15 ml dry THF under argon at 0° C. was added NaH (109 mg, 2.7 mmol). After stirring for 15 min, ethyl iodide (421 mg, 2.7 mmol) was added and stirred at room temperature. The reaction was checked with TLC until 18 was fully converted. The mixture was purified with flash chromatography in 4% MeOH in CHCl$_3$ TLC [5% MeOH in CHCl$_3$]: R$_f$=0.56

Yield: 538 mg, 1.8 mmol (95%)

$^1$HNMR (300 MHz, CDCl$_3$) δ=7.25-7.45 (m, 5H), 5.03-5.23 (m, 2H), 4.65-4.77 (m, 1H), 4.45-4.65 (m, 1H), 3.55-3.78 (m, 2H), 3.05-3.33 (m, 2H), 1.95-2.07 (m, 1H), 1.55-1.90 (m, 5H), 1.13-1.23 (t, 3H, J=7.18, 7.18 Hz)

HRMS: m/z: found 303.1703[M+H]$^+$, calculated 303.1709 [M+H]$^+$

Synthesis of 3-ethyl-3,9-diazabicyclo[3.3.1]nonan-2-one

To a solution of benzyl 3-ethyl-2-oxo-3,9-diazabicyclo [3.3.1]nonane-9-carboxylate (100 mg, 0.3 mmol) in 1 ml anhydrous MeOH was added catalytic amounts of Palladium on carbon and degassed with H$_2$. After stirring under 1 atm H$_2$ at room temperature for 2 h, the reaction mixture was filtered through celite and concentrated in vacuo. A 20% HCl solution (5 ml) was added and extracted with DCM (4×10 ml).

The aqueous layer was basified with saturated NaHCO$_3$ solution and extracted with DCM (4×10 ml). The organic layer was concentrated and used for the next step without further purification.

TLC [5% MeOH in CHCl$_3$]: R$_f$=0.37

Yield: 45 mg, 0.3 mmol (81%)

$^1$HNMR (300 MHz, CDCl$_3$) δ=3.6-3.73 (m, 2H), 3.53-3.57 (m, 1H), 3.35-3.43 (m, 1H), 3.22-3.35 (m, 1H), 3.13-3.21 (m, 1H), 1.55-2.03 (m, 6H), 1.15-1.23 (t, 3H, J=7.19, 7.19 Hz)

$^{13}$C NMR (75 MHz, CDCl$_3$) δ=170.96, 54.63, 51.52, 46.06, 41.34, 32.17, 29.27, 18.51, 12.28

HRMS: m/z: found 169.1333[M+H]$^+$, calculated 169.1314 [M+H]$^+$

Synthesis of 1-(3-ethyl-2-oxo-3,9-diazabicyclo [3.3.1]nonan-9-yl)-2-(3,4,5-trimethoxyphenyl) ethane-1,2-dione 2-oxo-2-(3,4,5-trimethoxyphenyl) acetic acid (42 mg, 0.2 mmol) in 1 ml DMF was treated with oxalyl chloride (47 mg, 0.5 mmol) and stirred at 0° C. for 3 h. The reaction mixture was first concentrated in vacuo and then dissolved in 1 ml DCM followed by addition of 3-ethyl-3,9-diazabicyclo [3.3.1]nonan-2-one (30 mg, 0.2 mmol), DIPEA (28 mg, 0.2 mmol) and stirred at room temperature for 1 h. The reaction was quenched with saturated NH$_4$Cl solution (5 ml), extracted with DCM (4×10 ml). The organic layers were dried over MgSO$_4$ and concentrated in vacuo. The mixture was purified with flash chromatography in hexane: EtOAc 2:1.

TLC [hexane: EtOAc]: R$_f$=0.09

Yield: 20 mg, 0.05 mmol (28%) purity >99%

$^1$HNMR (300 MHz, CDCl$_3$) δ=7.23 (s, 1H), 7.19 (s, 1H), 5.17-5.22 (m, 0.5H), 5.05-5.12 (m, 0.5H), 4.13-4.18 (m, 0.5H), 3.98-4.06 (m, 0.5H), 3.94-3.97 (m, 3H), 3.88-3.93 (m, 6H), 3.62-3.89 (m, 1.5H), 3.21-3.42 (m, 2H), 3.13-3.17 (m, 0.5H), 2.15-2.25 (m, 1H), 1.72-2.05 (m, 5H), 1.16-1.24 (m, 3H)

$^{13}$C NMR (75 MHz, CDCl$_3$) δ=(189.91, 189.62), (166.69, 166.19), (164.21, 163.62), (153.70, 153.65), (144.78, 144.72), (128.17, 128.05), (107.40, 107.29), (61.31, 61.28), 56.65, 56.60, 56.31, (51.35, 50.55), (49.75, 48.35), (41.57, 41.47), (31.60, 30.68), (29.09, 28.45), (18.31, 18.21), 12.19

HRMS: m/z: found 391.1863[M+H]⁺, calculated 391.1869 [M+H]⁺

Synthesis of 1-(3-(2-(3,4-dimethoxyphenoxyl)ethyl)-2-oxo-3,10-diazabicyclo-[4.3.1]decan-10-yl)-2-(3,4,5-trimethoxyphenyl)ethane-1,2-dione 5a 3-(2-(3,4-Dimethoxyphenoxy)ethyl)-3,10-diazabicyclo[4.3.1]decan-2-one (20 mg, 0.06 mmol) in 3 ml DCM was treated sequentially with 2-oxo-2-(3,4,5-trimethoxyphenyl) acetic acid (16 mg, 0.07 mmol), EDC-HCl (14 mg, 0.07 mmol), HOBt (10 mg, 0.07 mmol), TEA (7 mg, 0.07 mmol) at room temperature and stirred for 6 h. The reaction was quenched with saturated NH4Cl solution (5 ml), extracted with DCM (4×10 ml). The organic layers were dried over MgSO4 and concentrated in vacuo. The reaction mixture was purified with flash chromatography in EtOAc.

TLC [EtOAc]: $R_f$=0.23

Yield: 22 mg, 0.04 mmol (67%) purity >98%

$^1$H-NMR (600 MHz, CDCl$_3$): δ=7.2 (d, 2H, J=3.95), 6.78-6.82 (m, 1H), 6.51-6.55 (m, 1H), 6.4-6.46 (m, 1H), 5.59 (s, 0.5H), 5.12 (s, 0.5H), 4.0-4.36 (m, 5H), 3.97 (d, 3H, J=2.62), 3.92 (d, 6H, J=2.23), 3.88 (d, 3H, J=2.67), 3.86 (d, 3H, J=2.02), 3.6-3.7 (m, 1H), 3.36-3.46 (m, 1H), 2.4-2.6 (m, 2H), 1.5-1.8 (m, 6H)

$^{13}$C-NMR (150 MHz, CDCl$_3$): δ=(190.62, 190.22), (170.56, 170.30), 167.04, 165.98, (153.54, 153.49), (153.14, 153.13), 149.95, (144.51, 144.48), (143.80, 143.77), (128.04, 127.86), (112.02, 111.99), 107.01, 106.88, (104.15, 104.09), (100.65, 100.55), (67.33, 67.29), (61.09, 61.07), 58.68, 56.46, 56.45, 56.39, 55.91, 53.09, (51.27, 51.23), 49.81, (47.58, 43.38), (29.7, 29.66), 29.47, 29.03

HRMS (EI): m/z: found 556.2417 [M]⁺, calculated 556.2421 [M]

Synthesis of Reference Example 1-(3-(2-(3,4-dimethoxyphenoxyl)ethyl)-2-oxo-3,10-diazabicyclo-[4.3.1]decan-10-yl)-3,3-dimethylpentane-1,2-dione 5f To a solution of 3-(2-(3,4-dimethoxyphenoxy)ethyl)-3,10-diazabicyclo[4.3.1]decan-2-one 24a (22 mg, 0.06 mmol) in 3 ml DCM was added sequentially 3,3-dimethyl-2-oxopentanoic acid 25e (19 mg, 0.1 mmol), EDC-HCl (25 mg, 0.1 mmol), HOBt (17 mg, 0.1 mmol), TEA (8 mg, 0.08 mmol) at room temperature and stirred overnight. The reaction was quenched with saturated NH4Cl solution (5 ml), extracted with DCM (4×10 ml). The organic layers were dried over MgSO4 and concentrated in vacuo. The reaction mixture was purified with flash chromatography in EtOAc.

TLC [EtOAc]: $R_f$=0.69

Yield: 18 mg, 0.04 mmol (60%) purity >98%

$^1$H-NMR (600 MHz, CDCl$_3$): δ=6.77 (d, J=8.75) 1H, 6.47-6.5 (m, 1H), 6.37-6.4 (m, 1H), 5.36-5.38 (m, 0.5H), 4.88-4.94 (m, 0.5H), 4.14-4.17 (m, 1H), 4.09-4.14 (m, 1H), 4.01-4.07 (m, 1.5H), 3.96-4.01 (m, 0.5H), 3.92-3.955 (m, 0.5H), 3.85-3.88 (m, 0.3H), 3.85 (s, 3H), 3.832-3.84 (m, 0.2H), 3.83 (d, J=1.69, 3H), 3.77-3.81 (m, 0.5H), 3.66-3.77 (m, 1.5H), 3.56-3.62 (m, 0.5H), 3.28-3.35 (m, 1H), 2.44-2.50 (m, 1H), 2.36-2.42 (m, 1H), 2.27-2.34 (m, 1H), 2.16-2.23 (m, 1H), 1.99-2.08 (m, 1H), 1.78-1.86 (m, 1H), 1.52-1.74 (m, 6H), 1.24 (s, 1.5H), 1.12-1.19 (m, 4.5H), 0.82-0.91 (m, 3H)

$^{13}$C-NMR (150 MHz, CDCl$_3$): δ=(208.39, 207.54), (170.67, 170.39), (167.50, 166.19), (153.11, 153.06), 149.85, (143.68, 143.65), (111.92, 111.85), (103.95, 103.90), (100.53, 100.47), (67.20, 67.17), (58.59, 49.40) (56.41, 56.40), 55.85, (52.74, 43.06), (51.32, 51.13), (47.73, 47.39), (46.71, 46.52), (32.57, 31.90), (32.54, 32.53), (30.02, 28.72), (29.25, 29.11), (24.11, 23.39), (23.05, 22.7), (15.81, 15.67), (8.74, 8.73)

HRMS (EI): m/z: found 460.2571 [M]⁺, calculated 460.2573 [M]⁺

Synthesis of benzyl 3-(3,4-dimethoxyphenethyl)-2-oxo-3,10-diazabicyclo-[4.3.1]decane-10-carboxylate To a solution of benzyl 2-oxo-3,10-diazabicyclo[4.3.1]decane-10-carboxylate (100 mg, 0.3 mmol) in 2 ml dry THF under argon at 0° C. was added NaH (25 mg, 0.9 mmol) and stirred for 15 min followed by addition of commercially available 3,4-dimethoxyphenylethyl bromide (213 mg, 0.9 mmol). The mixture was stirred at room temperature for 2 days and concentrated in vacuo. A 10% HCl solution (5 ml) was added and extracted with DCM (4×10 ml). The organic phases were dried over MgSO$_4$, concentrated in vacuo and purified with flash chromatography in hexane:EtOAc 1:2.

TLC [hexane: EtOAc 1:2]: $R_f$=0.44

Yield: 39 mg, 0.1 mmol (25%)

$^1$H-NMR (600 MHz, CDCl$_3$): δ=7.27-7.39 (m, 5H), 6.72-6.78 (m, 3H), 5.13-5.17 (m, 2H), 5.09-5.13 (m, 0.5H), 4.99-5.05 (m, 0.5H), 4.45-4.65 (m, 1H), 3.8-3.9 (m, 6H), 3.45-3.77 (m, 4H), 3.27-3.37 (m, 1H), 2.85-2.95 (m, 1H), 2.70-2.85 (m, 2H), 2.30-2.45 (m, 1H), 2.00-2.20 (m, 1H), 1.50-1.80 (m, 3H), 0.86-0.94 (m, 1H)

$^{13}$C-NMR (150 MHz, CDCl$_3$): δ=(171.81, 171.85), (155.71, 155.90), 148.90, (147.58, 147.52), 136.40, (131.58, 131.23), (128.55, 128.52), (128.17, 128.10), (127.95, 127.80), (120.74, 120.68), (112.05, 111.93), (111.19, 111.14), (67.52, 67.45), 56.17, (55.88, 55.85), 53.65, 53.20, (46.55, 46.27), (46.20, 45.73), (33.79, 33.72), (33.25, 31.90), (28.76, 28.65), (15.33, 15.24)

HRMS: m/z: found 468.2484 [M]⁺, calculated 453.2389 [M]

Synthesis of 3-(3,4-dimethoxyphenethyl)-3,10-diazabicyclo[4.3.1]decan-2-one

To a solution of benzyl 3-(3,4-dimethoxyphenethyl)-2-oxo-3,10-diazabicyclo[4.3.1]decane-10-carboxylate (10 mg, 0.02 mmol) in 1 ml anhydrous MeOH was added catalytic amounts of Palladium on carbon and degassed with H$_2$. The reaction was stirred under 1 atm H$_2$ at room temperature for 1 h, filtered through celite, concentrated in vacuo and used for the next step without further purification.

TLC [10% MeOH in CHCl$_3$]: $R_f$=0.51

Yield: 5 mg, 0.02 mmol (71%)

MS (ESI) m/z: found 319.42 [M+H]⁺, calculated 319.20 [M+H]⁺

Synthesis of 1-(3-(3,4-dimethoxyphenethyl)-2-oxo-3,10-diazabicyclo[4.3.1]-decan-10-yl)-2-(3,4,5-trimethoxyphenyl)ethane-1,2-dione 5h To a solution of 3-(3,4-dimethoxyphenethyl)-3,10-diazabicyclo[4.3.1]decan-2-one (27 mg, 0.09 mmol) in 3 ml DCM was added sequentially 2-oxo-2-(3,4,5-trimethoxyphenyl) acetic acid (23 mg, 0.1 mmol), EDC-HCl (20 mg, 0.1 mmol), HOBt (14 mg, 0.1 mmol), TEA (10 mg, 0.1 mmol) at room temperature and stirred overnight. The reaction was quenched with saturated NH$_4$Cl solution (5 ml), extracted with DCM (4×10 ml). The organic layers were dried over MgSO$_4$ and concentrated in vacuo. The reaction mixture was purified with flash chromatography in EtOAc. TLC [EtOAc]: $R_f$=0.42

Yield: 35 mg, 0.07 mmol (75%) purity >99%

$^1$H-NMR (600 MHz, CDCl$_3$): δ=7.17 (d, 2H, J=2.09), 6.74-6.82 (m, 5H), 4.27-4.30 (m, 1H), 3.94 (d, 3H, J=4.9), 3.90 (d, 6H, J=3.27), 3.87 (d, 3H, J=2.64), 3.85 (d, 3H, J=2.45), 3.80-3.84 (m, 1H), 3.66-3.78 (m, 2H), 3.54-3.66 (m,

1H), 2.96-3.03 (m, 1H), 2.78-2.87 (m, 2H), 2.50-2.58 (m, 1H), 2.32-2.38 (m, 1H), 2.23-2.31 (m, 1H), 2.05-2.12 (m, 1H), 1.77-1.91 (m, 2H), 1.69-1.76 (m, 1H), 1.51-1.59 (m, 1H)

$^{13}$C NMR (150 MHz, CDCl$_3$): δ=(190.59, 190.23), 171.11, (170.02, 169.72), (166.95, 165.85), (155.48, 153.44), (148.95, 148.91), (147.63, 147.61), (144.44, 144.38), (131.40, 131.30), (127.99, 127.81), (120.78, 120.77), (112.05, 111.97), (111.33, 111.28), (106.94, 106.78), (61.06, 61.05), 58.71, (56.38, 56.35), (55.92, 55.89), (55.86, 55.85), (53.63, 53.35), 53.05, 49.61, (46.38, 46.26), 43.15, (33.89, 33.75), (33.25, 32.06), 30.15, (29.65, 29.45), (29.2, 28.95), 21.03, (15.78, 15.58), 14.18

MS (ESI) m/z: found 541.27 [M+H]$^+$, calculated 541.25

HRMS (EI): m/z: found 540.2479 [M]$^+$, calculated 540.2472 [M]$^+$

Example 6

Generation of Biological Data

Fluorescence Polarization Assay

Binding of the bicyclic compounds to FKBPs was measured using a competitive fluorescence polarization The fluorescent ligand tracer 2a (from Konzany et al ChemBioChem 2009, 10, 1402-1410) was diluted in assay buffer to a concentration of 40 nM (double the final concentration of 20 nM). The compound library ligand was dissolved in DMSO to reach a 100-times concentrated stock solution. This was used for a 1:1 serial dilution in DMSO. Every sample of this serial dilution was diluted by a factor of 50 in assay buffer (25 mM HEPES, 0.1% triton, pH 8) supplemented with fluorescent ligand CK182 (40 nM) to achieve a 2× concentrated mixture of fluorescent tracer and the corresponding inhibitor. To each of these competitive ligand mixtures (30 µL), double the protein concentration (30 µL, 400 nM FKBP51FK1, 1600 nM FKBP52FK1), diluted in assay buffer was added. The samples were transferred to black 384-well assay plates (No.: 3575; Corning Life Sciences B.V., Schiphol-Rijk, Netherlands) After incubation at room temperature for 30 min the fluorescence anisotropy was measured (GENios Pro, Tecan, Mannedorf, Switzerland) by using an excitation filters of 485/20 nm and emission filters of 535/25 nm. For FKBP12, -51FK1 and -52FK1 the binding assays were performed in duplicates in the plate format. The competition curves were analyzed by using SigmaPlot11. Data were fitted to a four parameter logistic curve to deduce the IC50 values.

TABLE 1

Chemical compounds according to formula (I) used in fluorescence polarization assay: Binding affinity to FKBP12, FKBP51 and FKBP52

| Comp. No. | Structure | FKBP52 $K_i$ [µM](LE) | FKBP51 $K_i$ [µM](LE) | FKBP12 $K_i$ [µM](LE) |
|---|---|---|---|---|
| FK506 | | 0.08 ± 0.01 (0.17) | 0.028 ± 0.005 (0.18) | 0.01 ± 0.003 (0.24) |
| 3a | 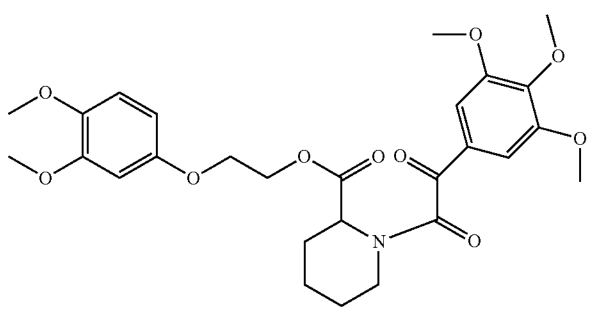 | >100 | >100 | 0.3 ± 0.03 (0.22) |
| 4a | 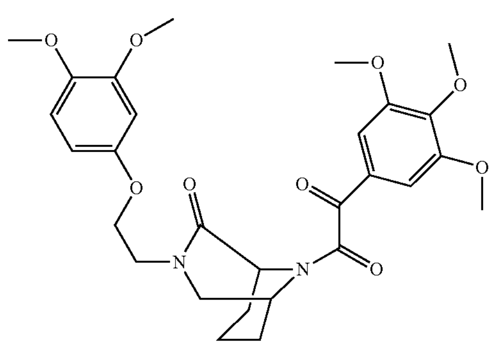 | 79.4 ± 20 (0.15) | 51.1 ± 7.6 (0.15) | 0.2 ± 0.01 (0.24) |

TABLE 1-continued

*Chemical compounds according to formula (I) used in fluorescence polarization assay: Binding affinity to FKBP12, FKBP51 and FKBP52*

| Comp. No. | Structure | FKBP52 $K_i$ [μM](LE) | FKBP51 $K_i$ [μM](LE) | FKBP12 $K_i$ [μM](LE) |
|---|---|---|---|---|
| 3b | 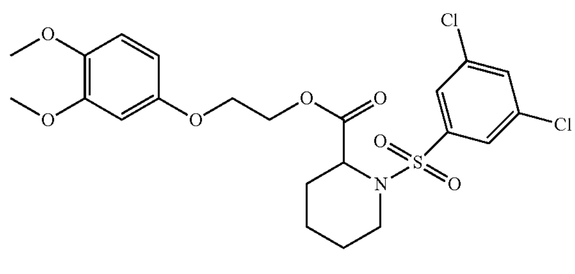 [SMILES: COc1ccc(OCCOC(=O)C2CCCCN2S(=O)(=O)c2cc(Cl)cc(Cl)c2)cc1OC] | >100 | >100 | 0.4 ± 0.006 (0.27) |
| 4b | 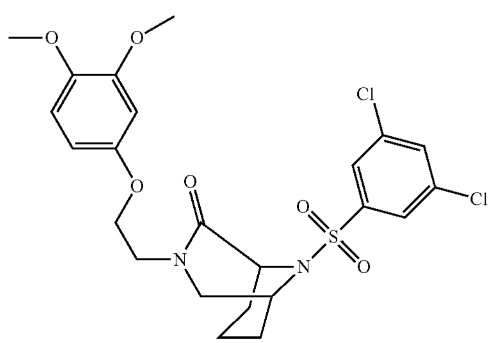 [SMILES: COc1ccc(OCCN2CC3CCCC(C2=O)N3S(=O)(=O)c2cc(Cl)cc(Cl)c2)cc1OC] | 12.2 ± 3.7 (0.20) | 8.8 ± 1.1 (0.21) | 0.14 ± 0.01 (0.28) |
| 5b | 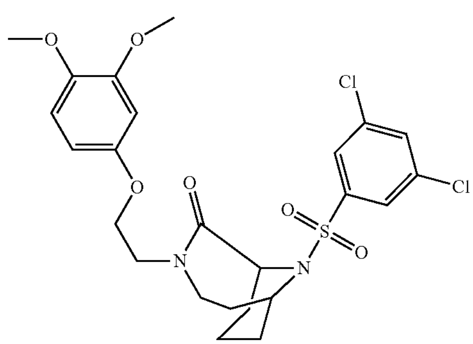 [SMILES: COc1ccc(OCCN2CCC3CCCC(C2=O)N3S(=O)(=O)c2cc(Cl)cc(Cl)c2)cc1OC] | 1.6 ± 0.3 (0.23) | 1.2 ± 0.2 (0.23) | 0.01 ± 0.002 (0.32) |
| 3c | 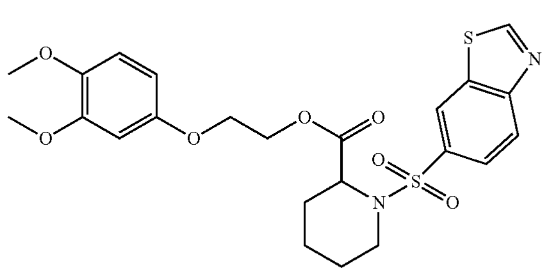 [SMILES: COc1ccc(OCCOC(=O)C2CCCCN2S(=O)(=O)c2ccc3ncsc3c2)cc1OC] | >100 | >100 | 0.1 ± 0.00003 (0.28) |

TABLE 1-continued

*Chemical compounds according to formula (I) used in fluorescence polarization assay: Binding affinity to FKBP12, FKBP51 and FKBP52*

| Comp. No. | Structure | FKBP52 $K_i$ [μM](LE) | FKBP51 $K_i$ [μM](LE) | FKBP12 $K_i$ [μM](LE) |
|---|---|---|---|---|
| 4c | 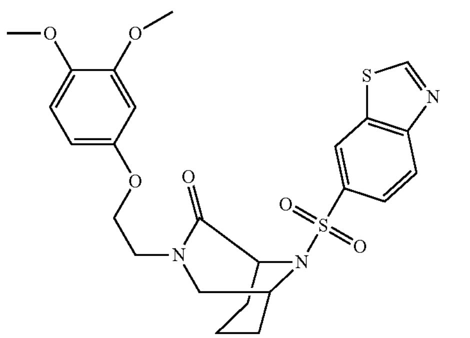 [SMILES: COc1ccc(OCCN2CC3CCCC(C2=O)N3S(=O)(=O)c2ccc3ncsc3c2)cc1OC] | n.d. | 64.8 ± 12.3 (0.17) | 0.9 ± 2 (0.24) |
| 5c | 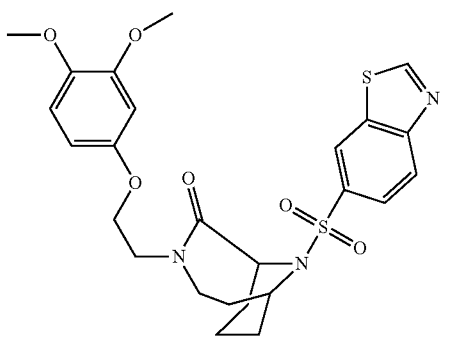 [SMILES: COc1ccc(OCCN2CCC3CCCC(C2=O)N3S(=O)(=O)c2ccc3ncsc3c2)cc1OC] | 3.6 ± 0.5 (0.21) | 2.1 ± 0.2 (0.22) | 0.03 ± 0.007 (0.29) |
| 4d | 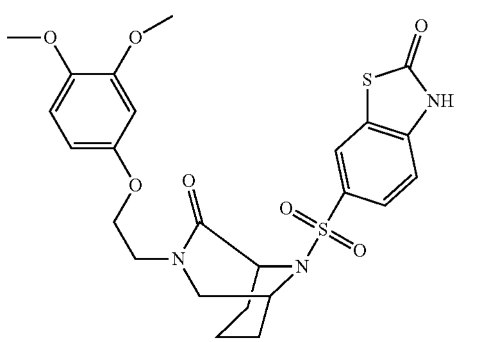 [SMILES: COc1ccc(OCCN2CC3CCCC(C2=O)N3S(=O)(=O)c2ccc3[nH]c(=O)sc3c2)cc1OC] | n.d. | 13.9 ± 0.9 (0.19) | 0.07 ± 0.0004 (0.28) |
| 5d | 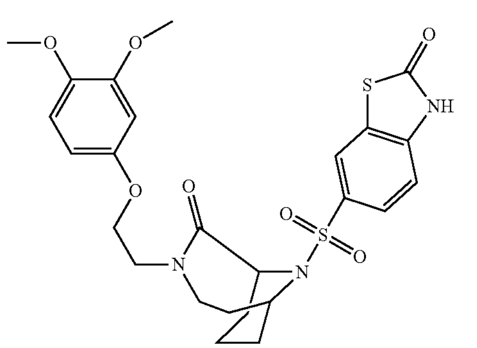 [SMILES: COc1ccc(OCCN2CCC3CCCC(C2=O)N3S(=O)(=O)c2ccc3[nH]c(=O)sc3c2)cc1OC] | 1.2 ± 0.2 (0.22) | 0.3 ± 0.02 (0.24) | 0.001 ± 0.0003 (0.34) |

TABLE 1-continued

*Chemical compounds according to formula (I) used in fluorescence polarization assay: Binding affinity to FKBP12, FKBP51 and FKBP52*

| Comp. No. | Structure | FKBP52 $K_i$ [μM](LE) | FKBP51 $K_i$ [μM](LE) | FKBP12 $K_i$ [μM](LE) |
|---|---|---|---|---|
| 3d | 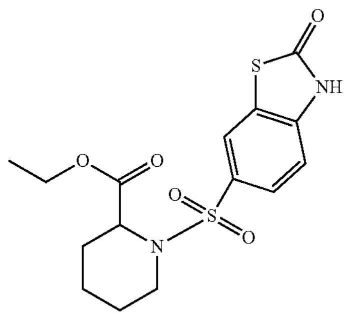 [SMILES: CCOC(=O)C1CCCCN1S(=O)(=O)c1ccc2[nH]c(=O)sc2c1] | >100 | >100 | 0.2 ± 0.004 (0.38) |
| 4e | 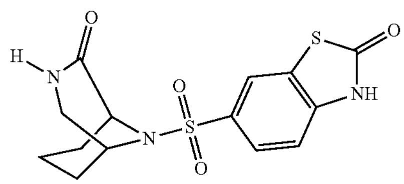 [SMILES: O=C1NCC2CCCC1N2S(=O)(=O)c1ccc2[nH]c(=O)sc2c1] | 46.4 ± 3.8 (0.26) | 27 ± 1.7 (0.27) | 0.1 ± 0.0005 (0.42) |
| 5e | 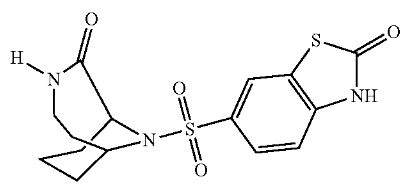 [SMILES: O=C1NCCC2CCCC1N2S(=O)(=O)c1ccc2[nH]c(=O)sc2c1] | 22.6 ± 1 (0.27) | 9.8 ± 0.5 (0.29) | 0.06 ± 0.002 (0.41) |
| 3e | 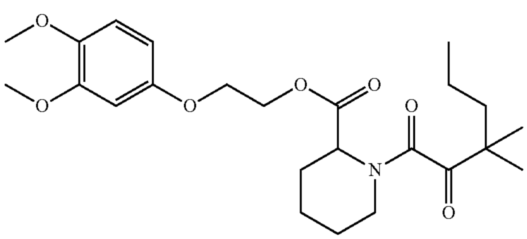 [SMILES: CCCC(C)(C)C(=O)C(=O)N1CCCCC1C(=O)OCCOc1ccc(OC)c(OC)c1] | >100 | >100 | 0.9 ± 0.1 (0.27) |
| 4f | 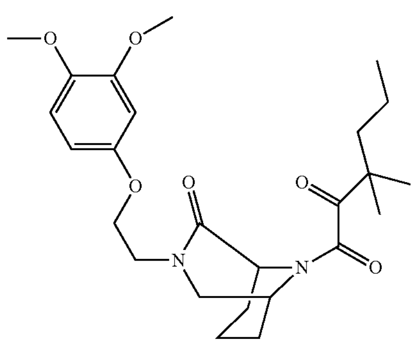 [SMILES: CCCC(C)(C)C(=O)C(=O)N1C2CCCC1C(=O)N(CCOc1ccc(OC)c(OC)c1)C2] | >100 | >100 | 3.5 ± 0.1 (0.24) |

TABLE 1-continued

Chemical compounds according to formula (I) used in fluorescence polarization assay: Binding affinity to FKBP12, FKBP51 and FKBP52

| Comp. No. | Structure | FKBP52 $K_i$ [μM](LE) | FKBP51 $K_i$ [μM](LE) | FKBP12 $K_i$ [μM](LE) |
| --- | --- | --- | --- | --- |
| 5f | 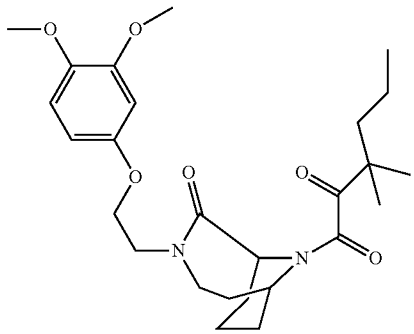 [SMILES: CCCC(C)(C)C(=O)C(=O)N1C2CCCC1C(=O)N(CCOc1ccc(OC)c(OC)c1)CC2] | >100 | >100 | 1.5 ± 0.1 (0.24) |
| 4g | 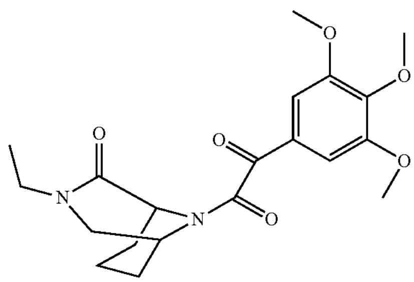 [SMILES: CCN1CC2CCCC(C1=O)N2C(=O)C(=O)c1cc(OC)c(OC)c(OC)c1] | >100 | >100 | 6.3 ± 0.02 (0.26) |
| 4h | 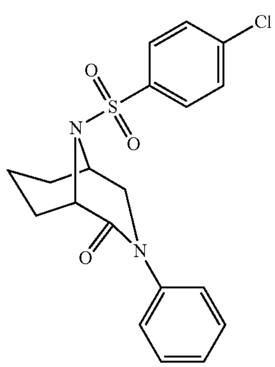 [SMILES: O=C1C2CCCC(CN1c1ccccc1)N2S(=O)(=O)c1ccc(Cl)cc1] | >100 | >100 | n.d. |
| 5h | 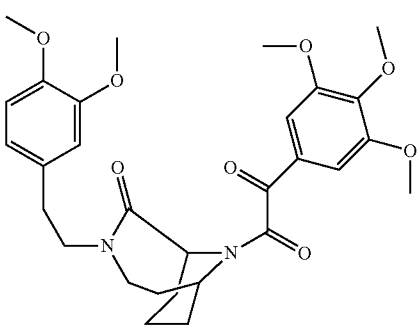 [SMILES: COc1ccc(CCN2CCC3CCCC(C2=O)N3C(=O)C(=O)c2cc(OC)c(OC)c(OC)c2)cc1OC] | >100 | >100 | 1.5 ± 0.04 (0.21) |

TABLE 1-continued

Chemical compounds according to formula (I) used in fluorescence polarization assay: Binding affinity to FKBP12, FKBP51 and FKBP52

| Comp. No. | Structure | FKBP52 $K_i$ [μM](LE) | FKBP51 $K_i$ [μM](LE) | FKBP12 $K_i$ [μM](LE) |
|---|---|---|---|---|
| 5i | 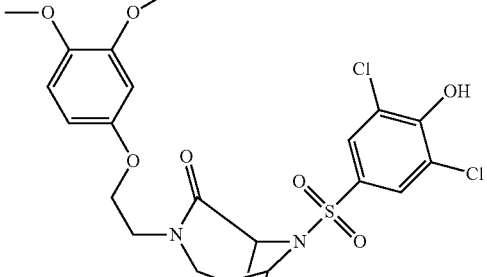 | 3.5 ± 0.4 (0.21) | 1 ± 0.1 (0.23) | 0.4 ± 0.04 (0.24) |
| 5k | 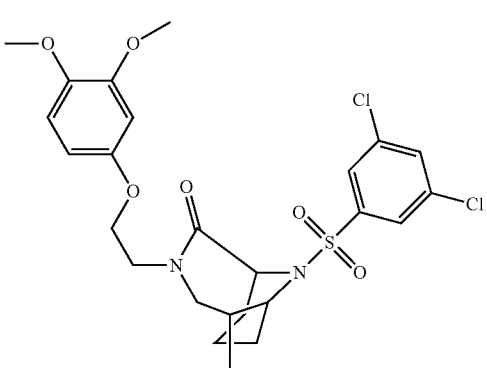 | 1.4 ± 0.2 (0.22) | 2.1 ± 0.4 (0.21) | 0.03 ± 0.003 (0.2) |

Ligand efficiency (LE) is defined as the ratio of Gibbs free energy (AG) to the number of non-hydrogen atoms of the compound: LE=(ΔG)/N, where ΔG=−RTlnK$_i$ with RT equal to 0.6 and N is the number of non-hydrogen atoms.

The invention claimed is:

1. Compound according to the general formula (I):

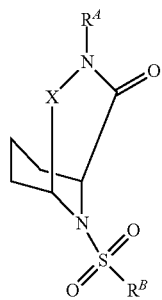

wherein

X represents —CH$_2$—CH$_2$— or —CH(CH=CH$_2$)—CH$_2$—;

R$^A$ represents —H, —CH$_3$, —C$_2$H$_5$, —C$_3$H$_7$, —CH(CH$_3$)$_2$, —C$_4$H$_9$, —CH$_2$—CH(CH$_3$)$_2$, —CH(CH$_3$)—C$_2$H$_5$, —C(CH$_3$)$_3$, —C$_5$H$_{11}$, —CH(CH$_3$)—C$_3$H$_7$, —CH$_2$—CH(CH$_3$)—C$_2$H$_5$, —CH(CH$_3$)—CH(CH$_3$)$_2$, —C(CH$_3$)$_2$—C$_2$H$_5$, —CH$_2$—C(CH$_3$)$_3$, —CH(C$_2$H$_5$)$_2$, —C$_2$H$_4$—CH(CH$_3$)$_2$, —C$_6$H$_{13}$, —C$_7$H$_{15}$, —C$_8$H$_{17}$, —C$_3$H$_6$—CH(CH$_3$)$_2$, —C$_2$H$_4$—CH(CH$_3$)—C$_2$H$_5$, —CH(CH$_3$)—C$_4$H$_9$, —CH$_2$—CH(CH$_3$)—C$_3$H$_7$, —CH(CH$_3$)—CH$_2$—CH(CH$_3$)$_2$, —CH(CH$_3$)—CH(CH$_3$)—C$_2$H$_5$, —CH$_2$—CH(CH$_3$)—CH(CH$_3$)$_2$, —CH$_2$—C(CH$_3$)$_2$—C$_2$H$_5$, —C(CH$_3$)$_2$—C$_3$H$_7$, —C(CH$_3$)$_2$—CH(CH$_3$)$_2$, —C$_2$H$_4$—C(CH$_3$)$_3$, —CH(CH$_3$)—C(CH$_3$)$_3$, —CH$_2$OH, —C$_2$H$_4$OH, —C$_3$H$_6$OH, —C$_4$H$_8$OH, —CH(CH$_3$)—C$_2$H$_4$OH, —C$_5$H$_{10}$OH, —CH$_2$OCH$_3$, —C$_2$H$_4$OCH$_3$, —C$_3$H$_6$OCH$_3$, —C$_4$H$_8$OCH$_3$, —CH(CH$_3$)—C$_2$H$_4$OCH$_3$, —C$_5$H$_{10}$OCH$_3$, —CH$_2$NH$_2$, —C$_2$H$_4$NH$_2$, —C$_3$H$_6$NH$_2$, —C$_4$H$_8$NH$_2$, —CH(CH$_3$)—C$_2$H$_4$NH$_2$, —C$_5$H$_{10}$NH$_2$, —CH=CH$_2$, —CH$_2$—CH=CH$_2$, —C(CH$_3$)=CH$_2$, —CH=CH—CH$_3$, —C$_2$H$_4$—CH=CH$_2$, —CH$_2$—CH=CH—CH$_3$, —CH=CH—C$_2$H$_5$, —CH$_2$—C(CH$_3$)=CH$_2$, —CH(CH$_3$)—CH=CH, —CH=C(CH$_3$)$_2$, —C(CH$_3$)=CH—CH$_3$, —CH=CH—CH=CH$_2$, —C$_3$H$_6$—CH=CH$_2$, —C$_2$H$_4$—CH=CH—CH$_3$, —CH$_2$—CH=CH—C$_2$H$_5$, —CH=CH—C$_3$H$_7$, —CH$_2$—CH=CH—CH=CH$_2$, —CH=CH—CH=CH—CH$_3$, —CH=CH—CH$_2$—CH=CH$_2$, —C(CH$_3$)=CH—CH=CH$_2$, —CH=C(CH$_3$)—CH=CH$_2$, —CH=CH—C(CH$_3$)=CH$_2$, —C$_2$H$_4$—C(CH$_3$)=CH$_2$, —CH$_2$—CH(CH$_3$)—CH=CH$_2$, —CH(CH$_3$)—CH$_2$—CH=CH$_2$, —CH$_2$—CH=C(CH$_3$)$_2$, —CH$_2$—C(CH$_3$)=CH—CH$_3$, —CH(CH$_3$)—CH=CH—CH$_3$, —CH=CH—CH(CH$_3$)$_2$, —CH=C (CH₃)—C₂H₅, —C(CH₃)=CH—C₂H₅, —C(CH₃)=C(CH₃)₂, —C(CH₃)₂—CH=CH₂, —CH(CH₃)—C(CH₃)=CH₂, —C(CH₃)=CH—CH₂, —CH=C(CH₃)—CH=CH₂, —CH=CH—C(CH₃)=CH₂, —C₄H₈—CH=CH₂, —C₃H₆—CH=CH—CH₃, —C₂H₄—CH=CH—C₂H₅, —CH₂—CH=CH—C₃H₇, —CH=CH—C₄H₉, —C₃H₆—C(CH₃)=CH₂, —C₂H₄—CH(CH₃)—CH=CH₂, —CH₂—CH(CH₃)—CH₂—CH=CH₂, —C₂H₄—CH=C(CH₃)₂, —CH(CH₃)—C₂H₄—CH=CH₂, —C₂H₄—C(CH₃)=CH—CH₃, —CH₂—CH(CH₃)—CH=CH—CH₃, —CH(CH₃)—CH₂—CH=CH—CH₃, —CH₂—CH=CH—CH(CH₃)₂, —CH₂—CH=C(CH₃)—C₂H₅, —CH₂—C(CH₃)=CH—C₂H₅, —CH(CH₃)—CH=CH—C₂H₅, —CH=CH—CH₂—CH(CH₃)₂, —CH=CH—CH(CH₃)—C₂H₅, —CH=C(CH₃)—C₃H₇, —C(CH₃)=CH—C₃H₇, —CH₂—CH(CH₃)—C(CH₃)=CH₂, —C[C(CH₃)₃]=CH₂, —CH(CH₃)—CH₂—C(CH₃)=CH₂, —CH(CH₃)—CH(CH₃)—CH=CH₂, —CH=CH—C₂H₄—CH=CH₂, —CH₂—C(CH₃)₂—CH=CH₂, —C(CH₃)₂—CH₂—CH=CH₂, —CH₂—C(CH₃)=C(CH₃)₂, —CH(CH₃)—CH=C(CH₃)₂, —C(CH₃)₂—CH=CH—CH₃, —CH=CH—CH₂—CH=CH—CH₃, —CH(CH₃)—C(CH₃)=CH—CH₃, —C(CH₃)=CH—CH(CH₃)₂, —C(CH₃)=CH—CH(CH₃)₂, —C(CH₃)=C(CH₃)—C₂H₅, —CH=CH—C(CH₃)₃, —C(CH₃)₂—C(CH₃)=CH₂, —CH(C₂H₅)—C(CH₃)=CH₂, —C(CH₃)(C₂H₅)—CH=CH₂, —CH(CH₃)—C(C₂H₅)=CH₂, —CH₂—C(C₃H₇)=CH₂, —CH₂—C(C₂H₅)=CH—CH₃, —CH(C₂H₅)—CH=CH—CH₃, —C(C₄H₉)=CH₂, —C(C₃H₇)=CH—CH₃, —C(C₂H₅)=CH—C₂H₅, —C(C₂H₅)=C(CH₃)₂, —C[CH(CH₃)(C₂H₅)]=CH₂, —C[CH₂—CH(CH₃)₂]=CH₂, —C₂H₄—CH=CH—CH=CH₂, —CH₂—CH=CH—CH₂—CH=CH₂, —C₃H₆—C≡C—CH₃, —CH₂—CH=CH—CH=CH—CH₃, —CH=CH—CH=CH—C₂H₅, —CH₂—CH=CH—C(CH₃)=CH₂, —CH₂—CH=C(CH₃)—CH=CH₂, —CH₂—C(CH₃)=CH—CH=CH₂, —CH(CH₃)—CH₂—C≡CH, —CH(CH₃)—CH=CH—CH=CH₂, —CH=CH—CH₂—C(CH₃)=CH₂, —CH(CH₃)—C≡C—CH₃, —CH=CH—CH(CH₃)—CH=CH₂, —CH=C(CH₃)—CH₂—CH=CH₂, —C₂H₄—CH(CH₃)—C≡CH, —C(CH₃)₂—CH—CH=CH₂, —CH=CH—CH=C(CH₃)₂, —CH₂—CH(CH₃)—CH₂—C≡CH, —CH=CH—C(CH₃)=CH—CH₃, —CH=C(CH₃)—CH=CH—CH₃, —CH₂—CH(CH₃)—C≡CH, —CH=C(CH₃)—CH=CH—CH₃, —CH=C(CH₃)—C(CH₃)=CH₂, —C(CH₃)=CH—C(CH₃)=CH₂, —C(CH₃)=C(CH₃)—CH=CH₂, —CH=CH—CH=CH—CH=CH₂, —C≡CH, —C≡C—CH₃, —CH₂—C≡CH, —C₂H₄—C≡CH, —CH₂—C≡C—CH₃, —C≡C—C₂H₅, —C₃H₆—C≡CH, —C₂H₄—C≡C—CH₃, —CH₂—C≡C—C₂H₅, —C≡C—C₃H₇, —CH(CH₃)—C≡CH, —C₄H₈—C≡CH, —C₂H₄—C≡C—C₂H₅, —CH₂—C≡C—C₃H₇, —C≡C—C₄H₉, —C≡C—C(CH₃)₃, —CH(CH₃)—C₂H₄—C≡CH, —CH₂—CH(CH₃)—C≡C—CH₃, —CH(CH₃)—C≡C—C₂H₅, —CH₂—C≡C—CH(CH₃)₂, —C≡C—CH(CH₃)—C₂H₅, —CH₂—CH(CH₃)—C≡C—CH₃, —C(CH₃)₂—C≡C—CH₃, —CH(C₂H₅)—C≡CH, —CH₂—CH(C₂H₅)—C≡CH, —CH₂—C(CH₃)₂—C≡CH, —CH (CH₃)—CH(CH₃)—C≡CH, —CH(C₃H₇)—C≡CH, —C(CH₃)(C₂H₅)—C≡CH, —CH₂-Ph,

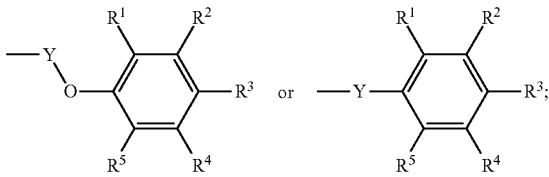

Y represents —CH₂—, —CH₂—CH₂—, —CH₂—CH₂—CH₂—, —CH=CH—, —CH=CH—CH₂—, —CH₂—CH=CH—, —CHCH₃—, —CHCH₃—CH₂—, —CH₂—CHCH₃—, —CH₂—CHCH₃—C₂, or —CH₂—O—CH₂—;

R^B represents

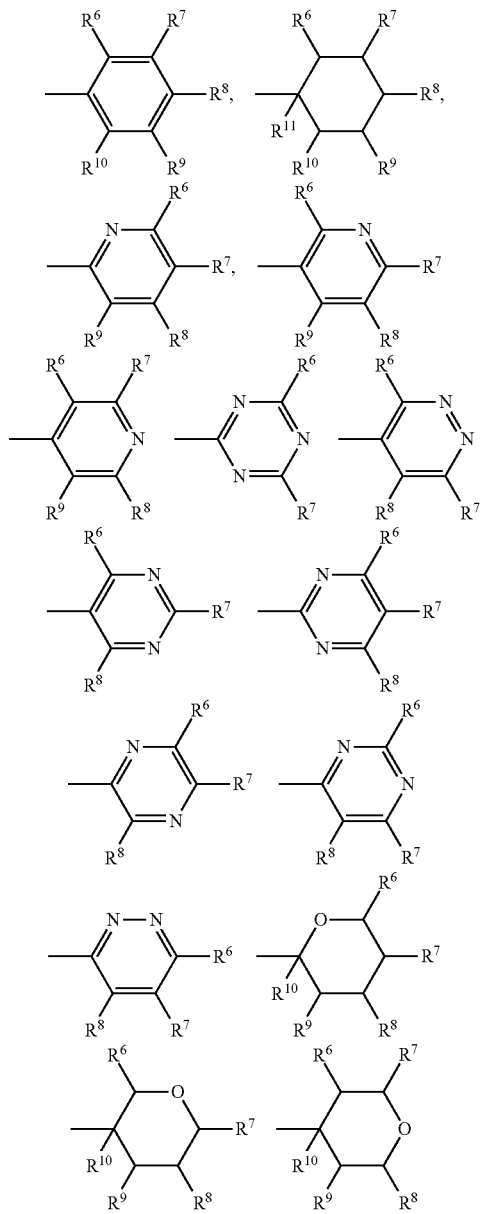

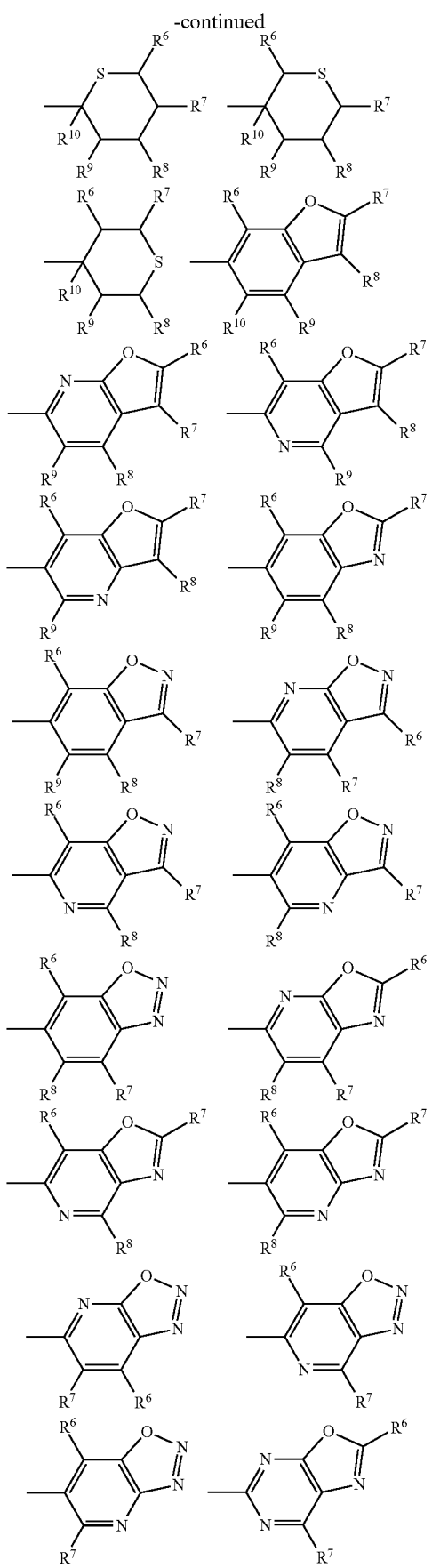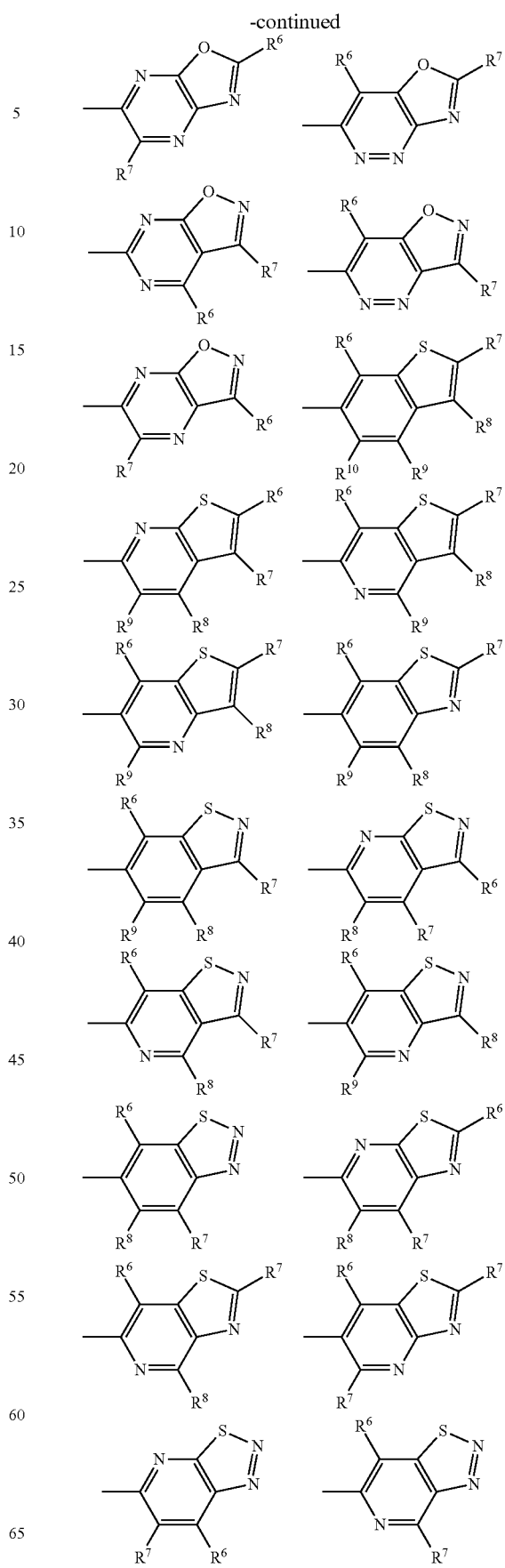

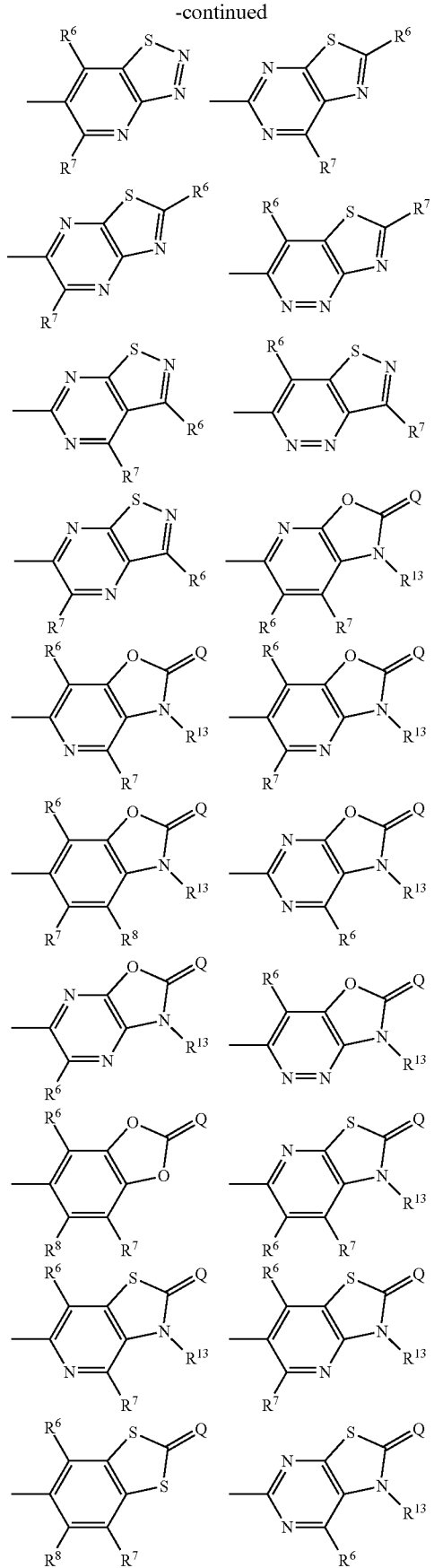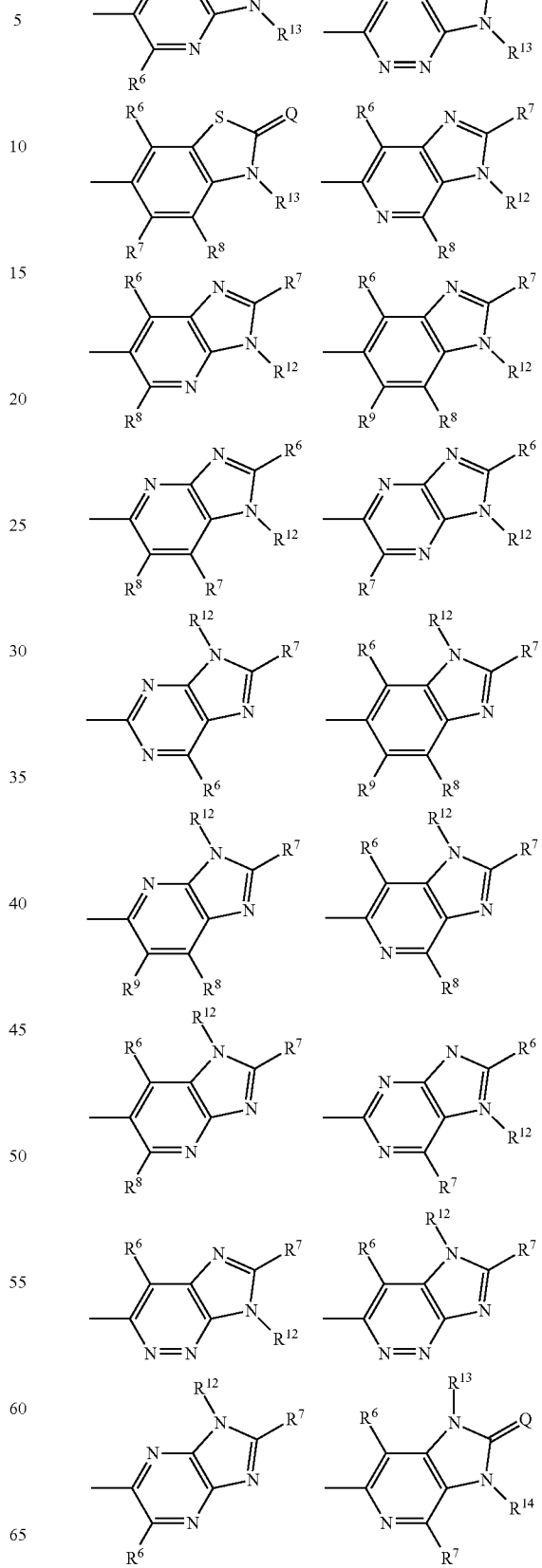

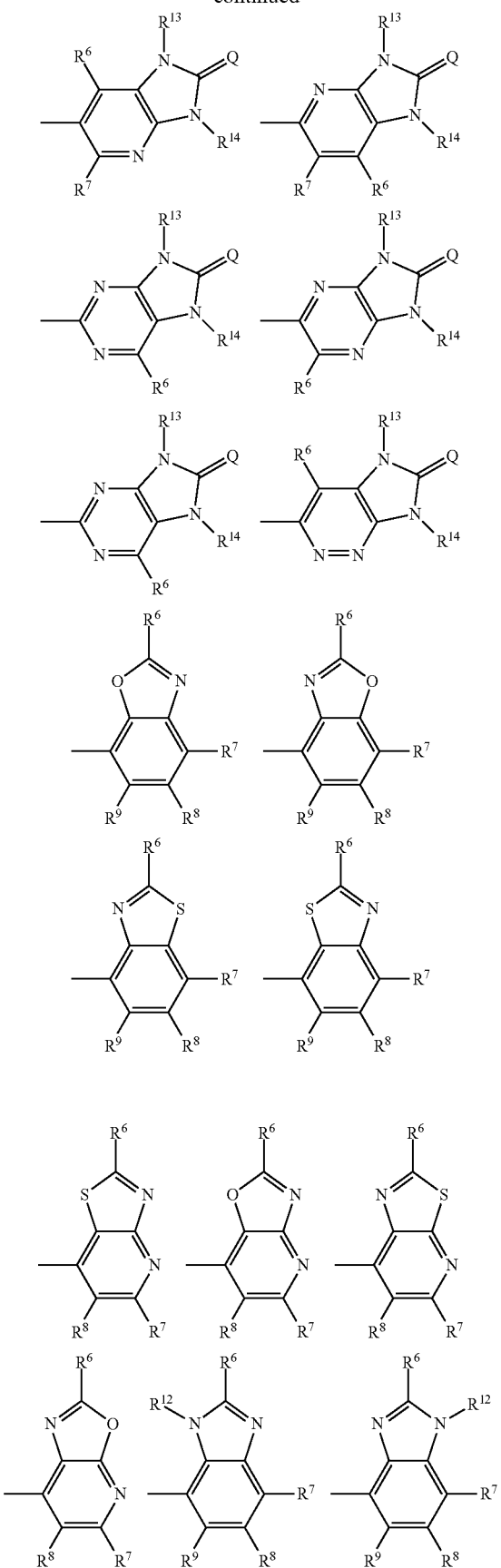
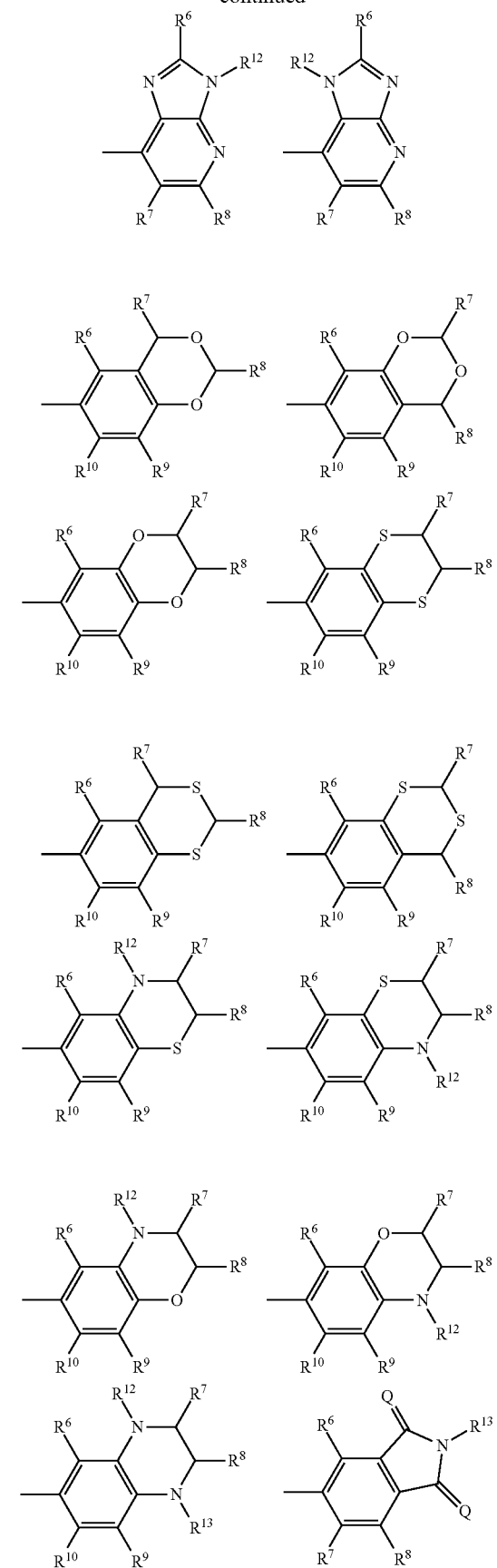

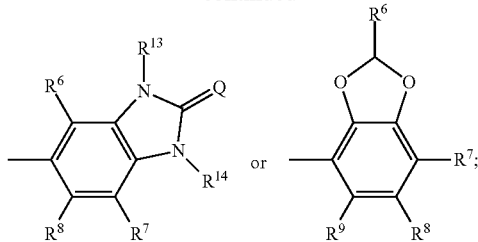

Q represents =O, =S, =N—R[12] or two hydrogen atoms forming a —CH$_2$— moiety together with the carbon atom to which Q is attached;

R[1]-R[11] represent independently of each other —H, —OH, —OCH$_3$, —OC$_2$H$_5$, —OC$_3$H$_7$, —O-cyclo-C$_3$H$_5$, —OCH(CH$_3$)$_2$, —OC(CH$_3$)$_3$, —OC$_4$H$_9$, —OCH$_2$—COOH, —OPh, —OCH$_2$-Ph, —OCPh$_3$, —CH$_2$—OCH$_3$, —CH$_2$—OH, —C$_2$H$_4$—OCH$_3$, —C$_3$H$_6$—OCH$_3$, —CH$_2$—OC$_2$H$_5$, —C$_2$H$_4$—OC$_2$H$_5$, —C$_3$H$_6$—OC$_2$H$_5$, —CH$_2$—OC$_3$H$_7$, —C$_2$H$_4$—OC$_3$H$_7$, —C$_3$H$_6$—OC$_3$H$_7$, —CH$_2$—O-cyclo-C$_3$H$_5$, —C$_2$H$_4$—O-cyclo-C$_3$H$_5$, —C$_3$H$_6$—O-cyclo-C$_3$H$_5$, —CH$_2$—OCH(CH$_3$)$_2$, —C$_2$H$_4$—OCH(CH$_3$)$_2$, —C$_3$H$_6$—OCH(CH$_3$)$_2$, —CH$_2$—OC(CH$_3$)$_3$, —C$_2$H$_4$—OC(CH$_3$)$_3$, —C$_3$H$_6$—OC(CH$_3$)$_3$, —CH$_2$—OC$_4$H$_9$, —C$_2$H$_4$—OC$_4$H$_9$, —C$_3$H$_6$—OC$_4$H$_9$, —CH$_2$—OPh, —C$_2$H$_4$—OPh, —C$_3$H$_6$—OPh, —CH$_2$—OCH$_2$-Ph, —C$_2$H$_4$—OCH$_2$-Ph, —C$_3$H$_6$—OCH$_2$-Ph, —SH, —SCH$_3$, —SC$_2$H$_5$, —SC$_3$H$_7$, —S-cyclo-C$_3$H$_5$, —SCH(CH$_3$)$_2$, —SC(CH$_3$)$_3$, —NO$_2$, —F, —Cl, —Br, —I, —P(O)(OH)$_2$, —P(O)(OCH$_3$)$_2$, —P(O)(OC$_2$H$_5$)$_2$, —P(O)(OCH(CH$_3$)$_2$)$_2$, —C(OH)[P(O)(OH)$_2$]$_2$, —Si(CH$_3$)$_2$(C(CH$_3$)$_3$), —Si(C$_2$H$_5$)$_3$, —Si(CH$_3$)$_3$, —N$_3$, —CN, —OCN, —NCO, —SCN, —NCS, —CHO, —COCH$_3$, —COC$_2$H$_5$, —COC$_3$H$_7$, —CO-cyclo-C$_3$H$_5$, —COCH(CH$_3$)$_2$, —COC(CH$_3$)$_3$, —COOH, —COCN, —COOCH$_3$, —COOC$_2$H$_5$, —COOC$_3$H$_7$, —COO-cyclo-C$_3$H$_5$, —COOCH(CH$_3$)$_2$, —COOC(CH$_3$)$_3$, —OOC—CH$_3$, —OOC—C$_2$H$_5$, —OOC—C$_3$H$_7$, —OOC-cyclo-C$_3$H$_5$, —OOC—CH(CH$_3$)$_2$, —OOC—C(CH$_3$)$_3$, —CONH$_2$, —CONHCH$_3$, —CONHC$_2$H$_5$, —CONHC$_3$H$_7$, —CONH-cyclo-C$_3$H$_5$, —CONH[CH(CH$_3$)$_2$], —CONH[C(CH$_3$)$_3$], —CON(CH$_3$)$_2$, —CON(C$_2$H$_5$)$_2$, —CON(C$_3$H$_7$)$_2$, —CON(cyclo-C$_3$H$_5$)$_2$, —CON[CH(CH$_3$)$_2$]$_2$, —CON[C(CH$_3$)$_3$]$_2$, —NHCOCH$_3$, —NHCOC$_2$H$_5$, —NHCOC$_3$H$_7$, —NHCO-cyclo-C$_3$H$_5$, —NHCO—CH(CH$_3$)$_2$, —NHCO—C(CH$_3$)$_3$, —NHCO—OCH$_3$, —NHCO—OC$_2$H$_5$, —NHCO—OC$_3$H$_7$, —NHCO—O-cyclo-C$_3$H$_5$, —NHCO—OCH(CH$_3$)$_2$, —NHCO—OC(CH$_3$)$_3$, —NH$_2$, —NHCH$_3$, —NHC$_2$H$_5$, —NHC$_3$H$_7$, —NH-cyclo-C$_3$H$_5$, —NHCH(CH$_3$)$_2$, —NHC(CH$_3$)$_3$, —N(CH$_3$)$_2$, —N(C$_2$H$_5$)$_2$, —N(C$_3$H$_7$)$_2$, —N(cyclo-C$_3$H$_5$)$_2$, —N[CH(CH$_3$)$_2$]$_2$, —N[C(CH$_3$)$_3$]$_2$, —SOCH$_3$, —SOC$_2$H$_5$, —SOC$_3$H$_7$, —SO-cyclo-C$_3$H$_5$, —SOCH(CH$_3$)$_2$, —SOC(CH$_3$)$_3$, —SO$_2$CH$_3$, —SO$_2$C$_2$H$_5$, —SO$_2$C$_3$H$_7$, —SO$_2$-cyclo-C$_3$H$_5$, —SO$_2$CH(CH$_3$)$_2$, —SO$_2$C(CH$_3$)$_3$, —SO$_3$H, —SO$_3$CH$_3$, —SO$_3$C$_2$H$_5$, —SO$_3$C$_3$H$_7$, —SO$_3$-cyclo-C$_3$H$_5$, —SO$_3$CH(CH$_3$)$_2$, —SO$_3$C(CH$_3$)$_3$, —SO$_2$NH$_2$, —SO$_2$NHCH$_3$, —SO$_2$NHC$_2$H$_5$, —SO$_2$NHC$_3$H$_7$, —SO$_2$NH-cyclo-C$_3$H$_5$, —SO$_2$NHCH(CH$_3$)$_2$, —SO$_2$NHC(CH$_3$)$_3$, —SO$_2$N(CH$_3$)$_2$, —SO$_2$N(C$_2$H$_5$)$_2$, —SO$_2$N(C$_3$H$_7$)$_2$, —SO$_2$N(cyclo-C$_3$H$_5$)$_2$, —SO$_2$N[CH(CH$_3$)$_2$]$_2$, —SO$_2$N[C(CH$_3$)$_3$]$_2$, —O—S(=O)CH$_3$, —O—S(=O)C$_2$H$_5$, —O—S(=O)C$_3$H$_7$, —O—S(=O)-cyclo-C$_3$H$_5$, —O—S(=O)CH(CH$_3$)$_2$, —O—S(=O)C(CH$_3$)$_3$, —S(=O)(=NH)CH$_3$, —S(=O)(=NH)C$_2$H$_5$, —S(=O)(=NH)C$_3$H$_7$, —S(=O)(=NH)-cyclo-C$_3$H$_5$, —S(=O)(=NH)CH(CH$_3$)$_2$, —S(=O)(=NH)C(CH$_3$)$_3$, —NH—SO$_2$—CH$_3$, —NH—SO$_2$—C$_2$H$_5$, —NH—SO$_2$—C$_3$H$_7$, —NH—SO$_2$-cyclo-C$_3$H$_5$, —NH—SO$_2$—CH(CH$_3$)$_2$, —NH—SO$_2$—C(CH$_3$)$_3$, —O—SO$_2$—CH$_3$, —O—SO$_2$—C$_2$H$_5$, —O—SO$_2$—C$_3$H$_7$, —O—SO$_2$-cyclo-C$_3$H$_5$, —O—SO$_2$—CH(CH$_3$)$_2$, —O—SO$_2$—C(CH$_3$)$_3$, —OCF$_3$, —CH$_2$—OCF$_3$, —C$_2$H$_4$—OCF$_3$, —C$_3$H$_6$—OCF$_3$, —OC$_2$F$_5$, —CH$_2$—OC$_2$F$_5$, —C$_2$H$_4$—OC$_2$F$_5$, —C$_3$H$_6$—OC$_2$F$_5$, —O—COOCH$_3$, —O—COOC$_2$H$_5$, —O—COOC$_3$H$_7$, —O—COO-cyclo-C$_3$H$_5$, —O—COOCH(CH$_3$)$_2$, —O—COOC(CH$_3$)$_3$, —NH—CO—NH$_2$, —NH—CO—NHCH$_3$, —NH—CO—NHC$_2$H$_5$, —NH—CS—N(C$_3$H$_7$)$_2$, —NH—CO—NHC$_3$H$_7$, —NH—CO—N(C$_3$H$_7$)$_2$, —NH—CO—NH[CH(CH$_3$)$_2$], —NH—CO—NH[C(CH$_3$)$_3$], —NH—CO—N(CH$_3$)$_2$, —NH—CO—N(C$_2$H$_5$)$_2$, —NH—CO—NH-cyclo-C$_3$H$_5$, —NH—CO—N(cyclo-C$_3$H$_5$)$_2$, —NH—CO—N[CH(CH$_3$)$_2$]$_2$, —NH—CS—N(C$_2$H$_5$)$_2$, —NH—CO—N[C(CH$_3$)$_3$]$_2$, —NH—CS—NH$_2$, —NH—CS—NHCH$_3$, —NH—CS—N(CH$_3$)$_2$, —NH—CS—NHC$_2$H$_5$, —NH—CS—NHC$_3$H$_7$, —NH—CS—NH-cyclo-C$_3$H$_5$, —NH—CS—NH[CH(CH$_3$)$_2$], —NH—CS—NH[C(CH$_3$)$_3$], —NH—CS—N(cyclo-C$_3$H$_5$)$_2$, —NH—CS—N[CH(CH$_3$)$_2$]$_2$, —NH—CS—N[C(CH$_3$)$_3$]$_2$, —NH—C(=NH)—NH$_2$, —NH—C(=NH)—NHCH$_3$, —NH—C(=NH)—NHC$_2$H$_5$, —NH—C(=NH)—NHC$_3$H$_7$, —O—CO—NH-cyclo-C$_3$H$_5$, —NH—C(=NH)—NH-cyclo-C$_3$H$_5$, —NH—C(=NH)—NH[CH(CH$_3$)$_2$], —O—CO—NH[CH(CH$_3$)$_2$], —NH—C(=NH)—NH[C(CH$_3$)$_3$], —NH—C(=NH)—N(CH$_3$)$_2$, —NH—C(=NH)—N(C$_2$H)$_2$, —NH—C(=NH)—N(C$_3$H$_7$)$_2$, —NH—C(=NH)—N(cyclo-C$_3$H$_5$)$_2$, —O—CO—NHC$_3$H$_7$, —NH—C(=NH)—N[CH(CH$_3$)$_2$]$_2$, —NH—C(=NH)—N[C(CH$_3$)$_3$]$_2$, —O—CO—NH$_2$, —O—CO—NHCH$_3$, —O—CO—NHC$_2$H$_5$, —O—CO—NH[C(CH$_3$)$_3$], —O—CO—N(CH$_3$)$_2$, —O—CO—N(C$_2$H$_5$)$_2$, —O—CO—N(C$_3$H$_7$)$_2$, —O—CO—N(cyclo-C$_3$H$_5$)$_2$, —O—CO—N[CH(CH$_3$)$_2$]$_2$, —O—CO—N[C(CH$_3$)$_3$]$_2$, —O—CO—OCH$_3$, —O—CO—OC$_2$H$_5$, —O—CO—OC$_3$H$_7$, —O—CO—O-cyclo-C$_3$H$_5$, —O—CO—OCH(CH$_3$)$_2$, —O—CO—OC(CH$_3$)$_3$, —CH$_2$F, —CHF$_2$, —CF$_3$, —CH$_2$Cl, —CH$_2$Br, —CH$_2$I, —CH$_2$—CH$_2$F, —CH$_2$—CHF$_2$, —CH$_2$—CF$_3$, —CH$_2$—CH$_2$Cl, —CH$_2$—CH$_2$Br, —CH$_2$—CH$_2$I, -cyclo-C$_3$H$_5$, -cyclo-C$_4$H$_7$, -cyclo-C$_5$H$_9$, -cyclo-C$_6$H$_{11}$, -cyclo-C$_7$H$_{13}$, -cyclo-C$_8$H$_{15}$, -Ph, —CH$_2$-Ph, —CH$_2$—CH$_2$-Ph, —CH=CH-Ph, —CPh$_3$, —CH$_3$, —C$_2$H$_5$, —C$_3$H$_7$, —CH(CH$_3$)$_2$, —C$_4$H$_9$, —CH$_2$—CH(CH$_3$)$_2$, —CH(CH$_3$)—C$_2$H$_5$, —C(CH$_3$)$_3$, —C$_5$H$_{11}$, —CH(CH$_3$)—C$_3$H$_7$, —CH$_2$—CH(CH$_3$)—C$_2$H$_5$, —CH(CH$_3$)—CH(CH$_3$)$_2$, —C(CH$_3$)$_2$—C$_2$H$_5$, —CH$_2$—C(CH$_3$)$_3$, —CH(C$_2$H$_5$)$_2$, —C$_2$H$_4$—CH(CH$_3$)$_2$, —C$_6$H$_{13}$, —C$_7$H$_{15}$, —C$_8$H$_{17}$, —C$_3$H$_6$—CH(CH$_3$)$_2$, —C$_2$H$_4$—CH(CH$_3$)—C$_2$H$_5$, —CH(CH$_3$)—C$_4$H$_9$, —CH$_2$—CH(CH$_3$)—C$_3$H$_7$, —CH(CH$_3$)—CH$_2$—CH(CH$_3$)$_2$, —CH(CH$_3$)—CH(CH$_3$)—C$_2$H$_5$, —CH$_2$—CH(CH$_3$)—CH(CH$_3$)$_2$, —CH$_2$—C(CH$_3$)$_2$—C$_2$H$_5$, —C(CH$_3$)$_2$—C$_3$H$_7$, —C(CH$_3$)$_2$—CH(CH$_3$)$_2$, —C$_2$H$_4$—C(CH$_3$)$_3$, —CH(CH$_3$)—C(CH$_3$)$_3$, —CH=CH$_2$, —CH$_2$—CH=CH$_2$, —C(CH$_3$)=CH$_2$, —CH=CH—CH$_3$, —C$_2$H$_4$—CH=CH$_2$, —CH$_2$—

—CH=CH—CH₃, —CH=CH—C₂H₅, —CH₂—C(CH₃)=CH₂, —CH(CH₃)—CH=CH, —CH=C(CH₃)₂, —C(CH₃)=CH—CH₃, —CH=CH—CH=CH₂, —C₃H₆—CH=CH₂, —C₂H₄—CH=CH—CH₃, —CH₂—CH=CH—C₂H₅, —CH=CH—C₃H₇, —CH₂—CH=CH—CH=CH₂, —CH=CH—CH=CH—CH₃, —CH=CH—CH₂—CH=CH₂, —C(CH₃)=CH—CH=CH₂, —CH=C(CH₃)—CH=CH₂, —CH=CH—C(CH₃)=CH₂, —C₂H₄—C(CH₃)=CH₂, —CH₂—CH(CH₃)—CH=CH₂, —CH(CH₃)—CH₂—CH=CH₂, —CH₂—CH=C(CH₃)₂, —CH₂—C(CH₃)=CH—CH₃, —CH(CH₃)—CH=CH—CH₃, —CH=CH—CH(CH₃)₂, —CH=C(CH₃)—C₂H₅, —C(CH₃)=CH—C₂H₅, —C(CH₃)=C(CH₃)₂, —C(CH₃)₂—CH=CH₂, —CH(CH₃)—C(CH₃)=CH₂, —C(CH₃)—CH=CH—CH₂, —CH=C(CH₃)—CH=CH₂, —CH=CH—C(CH₃)=CH₂, —C₄H₈—CH=CH₂, —C₃H₆—CH=CH—CH₃, —C₂H₄—CH=CH—C₂H₅, —CH₂—CH=CH—C₃H₇, —CH=CH—C₄H₉, —C₃H₆—C(CH₃)=CH₂, —C₂H₄—CH(CH₃)—CH=CH₂, —CH₂—CH(CH₃)—CH₂—CH=CH₂, —C₂H₄—CH=C(CH₃)₂, —CH(CH₃)—C₂H₄—CH=CH₂, —C₂H₄—CH=CH—CH₃, —CH₂—CH(CH₃)—CH=CH—CH₃, —CH(CH₃)—CH₂—CH=CH—CH₃, —CH₂—CH=CH—CH(CH₃)₂, —CH₂—CH=C(CH₃)—C₂H₅, —CH₂—C(CH₃)=CH—C₂H₅, —CH(CH₃)—CH=CH—C₂H₅, —CH=CH—CH₂—CH(CH₃)₂, —CH=CH—CH(CH₃)—C₂H₅, —CH=C(CH₃)—C₃H₇, —C(CH₃)=CH—C₃H₇, —CH₂—CH(CH₃)—C(CH₃)=CH₂, —C[C(CH₃)₃]=CH₂, —CH(CH₃)—CH₂—C(CH₃)=CH₂, —CH(CH₃)—CH(CH₃)—CH=CH₂, —CH₂—C(CH₃)₂—CH=CH₂, —C(CH₃)₂—CH₂—CH=CH₂, —CH₂—C(CH₃)=C(CH₃)₂, —CH(CH₃)—CH=C(CH₃)₂, —C(CH₃)₂—CH=CH—CH₃, —CH(CH₃)—C(CH₃)=CH—CH₃, —CH=C(CH₃)—CH(CH₃)₂, —C(CH₃)=CH—CH(CH₃)₂, —C(CH₃)=C(CH₃)—C₂H₅, —CH=CH—C(CH₃)₃, —C(CH₃)₂—C(CH₃)=CH₂, —CH(C₂H₅)—C(CH₃)=CH₂, —C(CH₃)(C₂H₅)—CH=CH₂, —CH(CH₃)—C(C₂H₅)=CH₂, —CH₂—C(C₃H₇)=CH₂, —CH₂—C(C₂H₅)=CH—CH₃, —CH(C₂H₅)—CH=CH—CH₃, —C(C₄H₉)=CH₂, —C(C₃H₇)=CH—CH₃, —C(C₂H₅)=CH—C₂H₅, —C(C₂H₅)=C(CH₃)₂, —C[CH(CH₃)(C₂H₅)]=CH₂, —C[CH₂—CH(CH₃)₂]=CH₂, —C₃H₆—C≡C—CH₃, —CH(CH₃)—CH₂—C≡CH, —CH(CH₃)—C≡C—CH₃, —C₂H₄—CH(CH₃)—C≡CH, —CH₂—CH(CH₃)—CH₂—C≡CH, —CH₂—CH(CH₃)—C≡CH, —C≡CH, —C≡C—CH₃, —CH₂—C≡CH, —C₂H₄—C≡CH, —CH₂—C≡C—CH₃, —C≡C—C₂H₅, —C₃H₆—C≡CH, —C₂H₄—C≡C—CH₃, —CH₂—C≡C—C₂H₅, —C≡C—C₃H₇, —CH(CH₃)—C≡CH, —C₄H₈—C≡CH, —C₂H₄—C≡C—C₂H₅, —CH₂—C≡C—C₃H₇, —C≡C—C₄H9, —C≡C—C(CH₃)₃, —CH(CH₃)—C₂H₄—C≡CH, —CH₂—CH(CH₃)—C≡C—CH₃, —CH(CH₃)—CH₂—C≡C—CH₃, —CH(CH₃)—C≡C—C₂H₅, —CH₂—C≡C—CH(CH₃)₂, —C≡C—CH(CH₃)—C₂H₅, —CH₂—C≡C—CH₂—CH(CH₃)₂, —CH(C₂H₅)—C≡C—CH₃, —C(CH₃)₂—C≡C—CH₃, —CH(C₂H₅)—CH₂—C≡CH, —CH₂—CH(C₂H₅)—C≡CH, —C(CH₃)₂—CH₂—C≡CH, —CH₂—C(CH₃)₂—C≡CH, —CH(C₃H₇)—C≡CH, —C(CH₃)(C₂H₅)—C≡CH or —CH₂—CH(C≡CH)₂;

R¹²-R¹⁴ represent independently of each other —H, —CH₂F, —CHF₂, —CH₂—OCH₃, —CH₂—OH, —C₂H₄—OCH₃, —C₃H₆—OCH₃, —CH₂—OC₂H₅, —C₂H₄—OC₂H₅, —C₃H₆—OC₂H₅, —CH₂—OC₃H₇, —C₂H₄—OC₃H₇, —C₃H₆—OC₃H₇, —CH₂—O-cyclo-C₃H₅, —C₂H₄—O-cyclo-C₃H₅, —C₃H₆—O-cyclo-C₃H₅, —CH₂—OCH(CH₃)₂, —C₂H₄—OCH(CH₃)₂, —C₃H₆—OCH(CH₃)₂, —CH₂—OC(CH₃)₃, —C₂H₄—OC(CH₃)₃, —C₃H₆—OC(CH₃)₃, —CH₂—OC₄H₉, —C₂H₄—OC₄H₉, —C₃H₆—OC₄H₉, —CH₂—OPh, —C₂H₄—OPh, —C₃H₆—OPh, —CH₂—OCH₂-Ph, —C₂H₄—OCH₂-Ph, —C₃H₆—OCH₂-Ph, —CF₃, —CH₂Cl, —CH₂Br, —CH₂I, —CH₂—CH₂F, —CH₂—CHF₂, —CH₂—CF₃, —CH₂—CH₂Cl, —CH₂—CH₂Br, —CH₂—CH₂I, -cyclo-C₃H₅, -cyclo-C₄H₇, -cyclo-C₅H₉, -cyclo-C₆H₁₁, -cyclo-C₇H₁₃, -cyclo-C₈H₁₅, -Ph, —CH₂-Ph, —CH₂—CH₂-Ph, —CH=CH-Ph, —CPh₃, —CH₃, —C₂H₅, —C₃H₇, —CH(CH₃)₂, —C₄H₉, —CH₂—CH(CH₃)₂, —CH(CH₃)—C₂H₅, —C(CH₃)₃, —C₅H₁₁, —CH(CH₃)—C₃H₇, —CH₂—CH(CH₃)—C₂H₅, —CH(CH₃)—CH(CH₃)₂, —C(CH₃)₂—C₂H₅, —CH₂—C(CH₃)₃, —CH(C₂H₅)₂, —C₂H₄—CH(CH₃)₂, —C₆H₁₃, —C₇H₁₅, —C₈H₁₇, —C₃H₆—CH(CH₃)₂, —C₂H₄—CH(CH₃)—C₂H₅, —CH(CH₃)—C₄H₉, —CH₂—CH(CH₃)—C₃H₇, —CH(CH₃)—CH₂—CH(CH₃)₂, —CH(CH₃)—CH(CH₃)—C₂H₅, —CH₂—CH(CH₃)—CH(CH₃)₂, —CH₂—C(CH₃)₂—C₂H₅, —C(CH₃)₂—C₃H₇, —C(CH₃)₂—CH(CH₃)₂, —C₂H₄—C(CH₃)₃, —CH(CH₃)—C(CH₃)₃, —CH=CH₂, —CH₂—CH=CH₂, —C(CH₃)=CH₂, —CH=CH—CH₃, —C₂H₄—CH=CH₂, —CH₂—CH=CH—CH₃, —CH=CH—C₂H₅, —CH₂—C(CH₃)=CH₂, —CH(CH₃)—CH=CH, —CH=C(CH₃)₂, —C(CH₃)=CH—CH₃, —CH=CH—CH=CH₂, —C₃H₆—CH=CH₂, —C₂H₄—CH=CH—CH₃, —CH₂—CH=CH—C₂H₅, —CH=CH—C₃H₇, —CH₂—CH=CH—CH=CH₂, —CH=CH—CH=CH—CH₃, —CH=CH—CH₂—CH=CH₂, —C(CH₃)=CH—CH=CH₂, —CH=C(CH₃)—CH=CH₂, —CH=CH—C(CH₃)=CH₂, —C₂H₄—C(CH₃)=CH₂, —CH₂—CH(CH₃)—CH=CH₂, —CH(CH₃)—CH₂—CH=CH₂, —CH₂—CH=C(CH₃)₂, —CH₂—C(CH₃)=CH—CH₃, —CH(CH₃)—CH=CH—CH₃, —CH=CH—CH(CH₃)₂, —CH=C(CH₃)—C₂H₅, —C(CH₃)=CH—C₂H₅, —C(CH₃)=C(CH₃)₂, —C(CH₃)₂—CH=CH₂, —CH(CH₃)—C(CH₃)=CH₂, —CH=C(CH₃)—CH=CH₂, —CH=CH—C(CH₃)=CH₂, —C₄H₈—CH=CH₂, —C₃H₆—CH=CH—CH₃, —C₂H₄—CH=CH—C₂H₅, —CH₂—CH=CH—C₃H₇, —CH=CH—C₄H₉, —C₃H₆—C(CH₃)=CH₂, —C₂H₄—CH(CH₃)—CH=CH₂, —CH₂—CH(CH₃)—CH₂—CH=CH₂, —C₂H₄—CH=C(CH₃)₂, —CH(CH₃)—C₂H₄—CH=CH₂, —C₂H₄—C(CH₃)=CH—CH₃, —CH₂—CH(CH₃)—CH=CH—CH₃, —CH(CH₃)—CH₂—CH=CH—CH₃, —CH₂—CH=CH—CH(CH₃)₂, —CH₂—CH=C(CH₃)—C₂H₅, —CH₂—C(CH₃)=CH—C₂H₅, —CH(CH₃)—CH=CH—C₂H₅, —CH=CH—CH₂—CH(CH₃)₂, —CH=CH—CH(CH₃)—C₂H₅, —CH=C(CH₃)—C₃H₇, —C(CH₃)=CH—C₃H₇, —CH₂—CH(CH₃)—C(CH₃)=CH₂, —C[C(CH₃)₃]=CH₂, —CH(CH₃)—CH₂—C(CH₃)=CH₂, —CH(CH₃)—CH(CH₃)—CH=CH₂, —CH₂—C(CH₃)₂—CH=CH₂, —C(CH₃)₂—CH₂—CH=CH₂, —CH₂—C(CH₃)=C(CH₃)₂, —CH(CH₃)—CH=C(CH₃)₂, —C(CH₃)₂—

CH=CH—CH₃, —CH(CH₃)—C(CH₃)=CH—CH₃, —CH=C(CH₃)—CH(CH₃)₂, —C(CH₃)=CH—CH(CH₃)₂, —C(CH₃)=C(CH₃)—C₂H₅, —CH=CH—C(CH₃)₃, —C(CH₃)₂—C(CH₃)=CH₂, —CH(C₂H₅)—C(CH₃)=CH₂, —C(CH₃)(C₂H₅)—CH=CH₂, —CH(CH₃)—C(C₂H₅)=CH₂, —CH₂—C(C₃H₇)=CH₂, —CH₂—C(C₂H₅)=CH—CH₃, —CH(C₂H₅)—CH=CH—CH₃, —C(C₄H₉)=CH₂, —C(C₃H₇)=CH—CH₃, —C(C₂H₅)=CH—C₂H₅, —C(C₂H₅)=C(CH₃)₂, —C[CH(CH₃)(C₂H₅)]=CH₂, —C[CH₂—CH(CH₃)₂]=CH₂, —C₃H₆—C≡C—CH₃, —CH(CH₃)—CH₂—C≡CH, —CH(CH₃)—C≡C—CH₃, —C₂H₄—CH(CH₃)—C≡CH, —CH₂—CH(CH₃)—CH₂—C≡CH, —CH₂—CH(CH₃)—C≡CH, —C≡CH, —C≡C—CH₃, —CH₂—C≡CH, —C₂H₄—C≡CH, —CH₂—C≡C—CH₃, —C≡C—C₂H₅, —C₃H₆—C≡CH, —C₂H₄—C≡C—CH₃, —CH₂—C≡C—C₂H₅, —C≡C—C₃H₇, —CH(CH₃)—C≡CH, —C₄H₈—C≡CH, —C₂H₄—C≡C—C₂H₅, —CH₂—C≡C—C₃H₇, —C≡C—C₄H₉, —C≡C—C(CH₃)₃, —CH(CH₃)—C₂H₄—C≡CH, —CH₂—CH(CH₃)—C≡C—CH₃, —CH(CH₃)—CH₂—C≡C—CH₃, —CH(CH₃)—C≡C—C₂H₅, —CH₂—C≡C—CH(CH₃)₂, —C≡C—CH(CH₃)—C₂H₅, —C≡C—CH₂—CH(CH₃)₂, —CH(C₂H₅)—C≡C—CH₃, —C(CH₃)₂—C≡C—CH₃, —CH(C₂H₅)—CH₂—C≡CH, —CH₂—CH(C₂H₅)—C≡CH, —C(CH₃)₂—CH₂—C≡CH, —CH₂—C(CH₃)₂—C≡CH, —CH(CH₃)—CH(CH₃)—C≡CH, —CH(C₃H₇)—C≡CH, —C(CH₃)(C₂H₅)—C≡CH, or —CH₂—CH(C≡CH)₂;

or enantiomers, stereoisomeric forms, mixtures of enantiomers, anomers, diastereomers, mixtures of diastereomers, tautomers, hydrates, solvates and racemates thereof and pharmaceutically acceptable salts thereof.

2. The compound according to claim 1 selected from the group consisting of
- 10-(benzo[d]thiazol-6-ylsulfonyl)-3-(2-(3,4-dimethoxyphenoxy)ethyl)-3,10-diazabicyclo[4.3.1]decan-2-one;
- 6-(3-(2-(3,4-dimethoxyphenoxy)ethyl)-2-oxo-3,10-diazabicyclo[4.3.1]decan-10-ylsulfonyl)benzo[d]thiazol-2(3H)-one;
- 6-(2-oxo-3,10-diazabicyclo[4.3.1]decan-10-ylsulfonyl)benzo[d]thiazol-2(3H)-one
- 10-(3,5-dichloro-4-hydroxyphenylsulfonyl)-3-(2-(3,4-dimethoxyphenoxy)ethyl)-3,10-diazabicyclo[4.3.1]decan-2-one;

and (1S,5S,6R)-10-(3,5-dichlorophenylsulfonyl)-3-(2-(3,4-dimethoxyphenoxy)ethyl)-5-vinyl-3,10-diazabicyclo[4.3.1]decan-2-one.

3. A pharmaceutical composition comprising at least one compound according to claim 1 together with at least one pharmaceutically acceptable carrier, solvent or excipient.

4. The pharmaceutical composition according to claim 3 further comprising at least one active agent selected from the group consisting of an anti-depressant and other psychotropic drugs.

5. The pharmaceutical composition according to claim 4, wherein the anti-depressant is selected from amitriptyline, amioxide clomipramine, doxepine, duloxetine, imipramine trimipramine, mirtazapine, reboxetine, citaloprame, fluoxetine, moclobemide and sertraline.

6. A method for inhibiting a FK506-binding protein comprising contacting the FK506-binding protein with an effective amount of a compound of claim 1, wherein the FK506-binding protein is selected from the group consisting of FK506-binding protein 12, FK506-binding protein 51 and FK506-binding protein 52.

7. A method for treating a condition comprising administering an effective amount of a compound of claim 1, wherein the condition is selected from an affective disorder, an anxiety disorder, prostate cancer, malignant melanoma, a metabolic disorder and glucocorticoid hyposensitivity syndrome.

8. The method according to claim 7, wherein the condition is an affective disorder.

9. The method according to claim 8, wherein the affective disorder is selected from the group consisting of: depression, bipolar disorder, mania, substance induced mood disorder and seasonal affective disorder (SAD).

10. The method of claim 7, wherein the condition is an anxiety disorder.

11. The method according to claim 10, wherein the anxiety disorder is selected from the group comprising or consisting of generalized anxiety disorder, panic disorder, panic disorder with agoraphobia, phobias, obsessive-compulsive disorder, post-traumatic stress disorder, separation anxiety and childhood anxiety disorders.

12. The method of claim 7, wherein the condition is prostate cancer.

13. The method of claim 7, wherein the condition is malignant melanoma.

14. The method of claim 7, wherein the condition is a metabolic disorder.

15. The method of claim 7, wherein the condition is glucocorticoid hyposensitivity syndrome.

* * * * *